(12) United States Patent
Tomkinson et al.

(10) Patent No.: US 9,132,120 B1
(45) Date of Patent: Sep. 15, 2015

(54) TARGETING ABNORMAL DNA REPAIR IN THERAPY-RESISTANT BREAST AND PANCREATIC CANCERS

(71) Applicants: STC.UNM, Albuquerque, NM (US); University of Maryland, Baltimore, Baltimore, MD (US)

(72) Inventors: Alan Edward Tomkinson, Albuquerque, NM (US); Feyruz Rassool, Baltimore, MD (US)

(73) Assignees: STC.UNM, Albuquerque, NM (US); UNIVERSITY OF MARYLAND, BALTIMORE, Baltimore, MD (US)

( * ) Notice: Subject to any disclaimer, the term of this patent is extended or adjusted under 35 U.S.C. 154(b) by 145 days.

(21) Appl. No.: 13/783,785

(22) Filed: Mar. 4, 2013

Related U.S. Application Data

(60) Provisional application No. 61/619,379, filed on Apr. 2, 2012.

(51) Int. Cl.
*A61K 31/4184* (2006.01)
*C40B 40/06* (2006.01)
*A61K 31/165* (2006.01)

(52) U.S. Cl.
CPC ........... *A61K 31/4184* (2013.01); *A61K 31/165* (2013.01)

(58) Field of Classification Search
CPC ............................ A61K 31/4184; C40B 40/06
USPC .............................................. 514/394; 506/16
See application file for complete search history.

(56) References Cited

U.S. PATENT DOCUMENTS

| 8,445,537 B2 | 5/2013 | Tomkinson et al. |
| 2010/0099683 A1 | 4/2010 | Tomkinson et al. |
| 2014/0113891 A1 | 4/2014 | Tomkinson et al. |

OTHER PUBLICATIONS

Jordan VC, Brodie AMH. Development and evolution of therapies targeted to the estrogen receptor for the treatment and prevention of breast cancer. Steroids, 2007;72:7-25.
Brodie A, Njar V, Macedo LF, Vasaitis TS, Sabnis G. The Coffey Lecture: Steroidogenic enzyme inhibitors and hormone dependent cancer. Urologic Oncology: Seminars and Original Investigations, 2009;27:53-63.
Macedo LF, Sabnis G, Brodie A. Aromatase Inhibitors and Breast Cancer. Steroid Enzymes and Cancer, 2009;1155:162-173.
Venkitaraman AR. Cancer Susceptibility and the Functions of BRCA1 and BRCA2. Cell, 2002;108:171-182.
Marshall M, Soloman S. Hereditary Breast-Ovarian Cancer: Clinical Findings and Medical Management. Plastic Surgical Nursing, 2007;27(3):124-127.
McCabe N, Turner NC, Lord CJ, et al. Deficiency in the Repair of DNA Damage by Homologous Recombinations and Sensitivity to Poly(ADP-Ribose) Polymerase Inhibition. Cancer Res, 2006;66(16):8109-8115.
Bryant HE, Schultz N, Thomas HD, Parker KM, Flower D, Lopez E, Kyle S, Meuth M, Curtin NJ, Helieday T. Specific killing of BRCA2-deficient tumours with inhibitors of poly(ADP-Ribose) polymerase. Nature, 2005;434:913-917.
Farmer H, McCabe N, Lord CJ, et al. Targeting the DNA repair defect in BRCA mutant cells as a therapeutic strategy. Nature, 2005;434:917-920.
Nussenzweig A, Nussenzweig MC. A Backup DNA Repair Pathway Moves to the Forefront. Cell, 2007;131:223-225.
Chen X, Zhong S, Zhu X, Dziegielewska B, Ellenberger T, Wilson GM, Mackerell AD, Tomkinson AE. Rational Design of Human DNA Ligase Inhibitors that Target Cellular DNA Replication and Repair. Cancer Res, 2008;68(9):3169-3177.
Sallmyr A, Tomkinson AE, Rassool FV. Up-regulation of WRN and DNA ligase IIIalpha in chronic myeloid leukemia: consequences for the repair of DNA double-strand breaks. Blood, 2008;112(4):1413-1423.
Fan J, Small D, Rassool F. Cells expressing FLT3/ITD mutations exhibit elevated repair errors generated through alternative NHEJ pathways: implications for genomic instability and therapy. Blood, 2010;116(24):5298-5305.
Wang H, Rosidi B, Perrault R, Wang M, Zhang L, Windhofer F, Iliakis G. DNA Ligase III as a Candidate Component of Backup Pathways of Nonhomologous End Joining. Cancer Res, 2005;65(10):4020-4030.
Wang H, Perrault AR, Takeda Y, Qin W, Wang H, Iliakis G. Biochemical evidence for Ku-independent backup pathways of NHEJ. Nucleic Acids Research, 2003;31(18):5377-5388.
Audebert M, Salles B, Calsou P. Involvement of Poly(ADP-ribose) Polymerase-1 and XRCC1/DNA Ligase III in an Alternative Route for DNA Double-strand Breaks Rejoining. J Biol Chem, 2004;279(53):56117-55126.
Long BJ, Jelovac D, Handratta V, Thiantanawat A, MacPherson N, Ragaz J, Goloubeva OG, Brodie AM. Therapeutic Strategies Using the Aromatase Inhibitor Letrozole and Tamoxifen in a Breast Cancer Model. J Natl Cancer Institute, 2004;96(6):456-465.

(Continued)

*Primary Examiner* — Raymond Henley, III
(74) *Attorney, Agent, or Firm* — Henry D. Coleman; R. Neil Sudol

(57) ABSTRACT

In one embodiment, the invention provides a method of treating a subject suffering from a breast cancer tumor which is non-responsive or intrinsically resistant to anti-estrogen therapy comprising administering a therapeutically effective amount of an inhibitor of alternative (ALT) non-homologous end joining (NHEJ) factor to the subject.

In another embodiment the invention provides a method of treating a subject who suffers from a pancreatic cancer which is non-responsive to chemotherapy and/or radiation comprising co-administering a therapeutically effective amount of PARP1 inhibitor and a DNA ligase IIIα inhibitor to the subject. Related diagnostic methods, nucleic acid arrays, devices and kits are also provided.

28 Claims, 10 Drawing Sheets

(56) References Cited

OTHER PUBLICATIONS

De Smith AJ, Tsalenko A, Sampas N, et al. Array CGH analysis of copy number variation identifies 1284 new genes variant in healthy white males: implications for association studies of complex diseases. Human Molecular Genetics, 2007;16(23):2783-2794.

Chou TC, Talalay P. Quantitative analysis of dose-effect relationships: the combined effects of multiple drugs or enzyme inhibitors. Adv Enzyme Regul 1984;22:27-55.

Chou TC. The median effect principle and the combination index for quantitation of synergism and antagonism. San Diego: Academic Press; 1991.

Lord CJ, Ashworth A. Targeted therapy for cancer using PARP inhibitors. Curr Opin Pharmacol 2008;8:363-369.

Wang H, Rosidi B, Perrault R, Wang M, Zhang L, Windhofer F, et al. DNA ligase III as a candidate component of backup pathways of nonhomologous end joining. Cancer Res 2005;65:4020-4030. 742.

Lobrich M, Shibata A, Beucher A, Fisher A, Ensminger M, Goodarzi AA, et al. gammaH2AX foci analysis for monitoring DNA double-strand break repair: strengths, limitations and optimization. Cell Cycle 2010;9:662-669.

Kunz C, Focke F, Saito Y, Schuermann D, Lettieri T, Selfridge J, et al. Base excision by thymine DNA glycosylase mediates DNA-directed cytotoxicity of 5-fluorouracil. PLoS Biol 2009;7:e91.

Corneo B, Wendland RL, Deriano L, Cui X, Klein IA, Wong SY, et al. Rag mutations reveal robust alternative end joining. Nature 2007; 449: 483-486.

Yan CT, Boboila C, Souza EK, Franco S, Hickernell TR, Murphy M, et al. IgH class switching and translocations use a robust non-classical end-joining pathway. Nature 2007;449:478-482.

Fattah F, Lee EH, Weisensel N, Wang Y, Lichter N, Hendrickson EA. Ku regulates the non-homologous end joining pathway choice of DNA double-strand break repair in human somatic cells. PLoS Genet 2010;6:e1000855.

Simsek D, Jasin M. Alternative end-joining is suppressed by the canonical NHEJ component Xrcc4-ligase IV during chromosomal translocation formation. Nat Struct Mol Biol 2010;17:410-416.

Sekiguchi J, Ferguson DO, Chen HT, Yang EM, Earle J, Frank K, et al. Genetic interactions between ATM and the nonhomologous end-joining factors in genomic stability and development. Proc Natl Acad Sci U S A 2001;98:3243-3248.

Medunjanin S, Weinert S, Schmeisser A, Mayer D, Braun-Dullaeus RC. Interaction of the double-strand break repair kinase DNA-PK and estrogen receptor-alpha. Mol Biol Cell 2010;21:1620-1628.

Medunjanin S, Weinert S, Poitz D, Schmeisser A, Strasser RH, Braun-Dullaeus RC. Transcriptional activation of DNA-dependent protein kinase catalytic subunit gene expression by oestrogen receptor-alpha. EMBO Rep 2010;11:208-213.

Nolens G, Pignon JC, Koopmansch B, Elmoualij B, Zorzi W, DePauw E, et al. Ku proteins interact with activator protein-2 transcription factors and contribute to ERBB2 overexpression in breast cancer cell lines. Breast Cancer Res 2009;11:R83.

Cheang MC, Chia SK, Voduc D, Gao D, Leung S, Snider J, et al. Ki67 index, HER2 status, and prognosis of patients with luminal B breast cancer. J Natl Cancer Inst 2009;101:736-750.

A

Substrate

| MCF10A CTRL | | Deletion size (bp) |
|---|---|---|
| -30                                     0 | 1                                    +30 | |
| CTAGAGGATCCCCGGGTACCGAGCTCGAATT | GTAATCATGGTCATAGCTGTTTCCTGTGTG | |
| GATCTCCTAGGGGCCCATGGCTCGAG | CTTAACATTAGTACCAGTATCGACAAAGGACACAC | |
| CTAGAGGATCCCCGGGTACCGAGCTCGAATT | GTAATCATGGTCATAGCTGTTTCCTGTGTG | 0 |
| CTAGAGGATCCCCGGGTACCGAGCTCGAAT | GTAATCATGGTCATAGCTGTTTCCTGTGTG | 1 |
| CTAGAGGATCCCCGGGTACCGAGCTCG | GTAATCATGGTCATAGCTGTTTCCTGTGTG | 4 |
| CTAGAGGATCCCCGGGTACCGAGCTC | TAATCATGGTCATAGCTGTTTCCTGTGTG | 6 |
| CTAGAGGATCCCCGGGTACCGAGCTCGAA | TGGTCATAGCTGTTTCCTGTGTG | 9 |
| CTAGAGGATCCCCGGGTACCGAG | AATCATGGTCATAGCTGTTTCCTGTGTG | 10 |
| CTAGAGGATCCCCGGGTAC | ATCATGGTCATAGCTGTTTCCTGTGTG | 15 |
| CTAGAGGATCCCCGGGTAC | TCATGGTCATAGCTGTTTCCTGTGTG | 16 |
| CTAGAGGATCCCCGGGTAC | GTCATAGCTGTTTCCTGTGTG | 21 |
| CTAGAGGATCCCCGGGTAC | TCATAGCTGTTTCCTGTGTG | 22 |
| CTAGAGGATC | CTGTTTCCTGTGTG | 37 |
| TTGCATGCTGCAGG-37 | TCCTGTGTG | 57 |
| CCAACGTTGCATGCC-41 | TG | 69 |
| CCAACGTTGCATGCC-41 | +31 AAATTGTTATCCGCT | 71 |
| ACGCCAGGGTTTTCC-89 | +71 GGAAGCATAAAGTGT | 158 |
| CCAGCTGGCGAAAGG-135 | +93 GGGGTGCCTAATGAG | 225 |

| MCF10A L67+ABT | | Deletion size (bp) |
|---|---|---|
| -30                                     0 | 1                                    +30 | |
| CTAGAGGATCCCCGGGTACCGAGCTCGAATT | GTAATCATGGTCATAGCTGTTTCCTGTGTG | |
| GATCTCCTAGGGGCCCATGGCTCGAG | CTTAACATTAGTACCAGTATCGACAAAGGACACAC | |
| CTAGAGGATCCCCGGGTACCGAGCTCG | GTAATCATGGTCATAGCTGTTTCCTGTGTG | 4 |
| CTAGAGGATCCCCGGGTACCGAGCTCG | TAATCATGGTCATAGCTGTTTCCTGTGTG | 5 |
| CTAGAGGATCCCCGGGTACCGAGCTC | TAATCATGGTCATAGCTGTTTCCTGTGTG | 6 |
| CTAGAGGATCCCCGGGTACCGAGCTCGAA | TGGTCATAGCTGTTTCCTGTGTG | 9 |
| CTAGAGGATCCCCGGGTAC | ATCATGGTCATAGCTGTTTCCTGTGTG | 15 |
| CTAGAGGATCCCCGGGTACC | ATGGTCATAGCTGTTTCCTGTGTG | 17 |
| CTAGAGGATCCCCGGGTAC | ATGGTCATAGCTGTTTCCTGTGTG | 18 |
| CTAGAGGATCCCCGGGTAC | GTCATAGCTGTTTCCTGTGTG | 21 |
| CTAGAGGATCCCCGGGT | CATAGCTGTTTCCTGTGTG | 25 |
| CTAGAGGATCCCCGG | CATAGCTGTTTCCTGTGTG | 26 |
| ACGTTGCATGCCTGC-40 | GTG | 67 |
| ACGCCAGGGTTTTCC-89 | +71 GGAAGCATAAAGTGT | 158 |

| | MCF7 CTRL | | Deletion size (bp) |
|---|---|---|---|
| -30 | 0    1 | +30 | |
| CTAGAGGATCCCCGGGTACCGAGCTCGAATT | | GTAATCATGGTCATAGCTGTTTCCTGTGTG | |
| GATCTCCTAGGGGCCCATGGCTCGAG | | CTTAACATTAGTACCAGTATCGACAAAGGACACAC | |
| CTAGAGGATCCCCGGGTACCGAGCTCGAATT | | GTAATCATGGTCATAGCTGTTTCCTGTGTG | 0 |
| CTAGAGGATCCCCGGGTACCGAGCTCG | | GTAATCATGGTCATAGCTGTTTCCTGTGTG | 4 |
| CTAGAGGATCCCCGGGTACCGAGCTC | | TAATCATGGTCATAGCTGTTTCCTGTGTG | 6 |
| CTAGAGGATCCCCGGGTAC | | ATCATGGTCATAGCTGTTTCCTGTGTG | 15 |
| CTAGAGGATCCCCGGGTAC | | GTCATAGCTGTTTCCTGTGTG | 21 |
| CTAGAGGATCCCCGGGT | | CATAGCTGTTTCCTGTGTG | 25 |
| CTAGAGGATCCCCGGG | | CATAGCTGTTTCCTGTGTG | 26 |
| GCATGCCTGCAGGTC-35 | | CTGTGTG | 57 |
| ACGTTGCATGCCTGC-40 | | GTG | 67 |
| CTA | | +47 ACAATTCCACACAAC | 73 |
| CTA | | +86 AAAGCCTGGGGTGCC | 111 |
| ACGCCAGGGTTTTCC-89 | | +89 CGGAAGCATAAAGT | 156 |
| AGTTGGGTAACGCCA-98 | | +70 CGGAAGCATAAAGTG | 166 |
| AGTTGGGTAACGCCA-98 | | +111 GCTAACTCACATTAA | 206 |
| AGTTGGGTAACGCCA-98 | | +170 TGCCAGCTGCATTAA | 266 |
| AGTTGGGTAACGCCA-98 | | +186 GAATCGGCCAACGCG | 282 |
| CCATTCAGGCTGCGC-194 | | +190 CGGCCAACGCGCGGG | 382 |

| | MCF7 L67+ABT | | Deletion size (bp) |
|---|---|---|---|
| -30 | 0    1 | +30 | |
| CTAGAGGATCCCCGGGTACCGAGCTCGAATT | | GTAATCATGGTCATAGCTGTTTCCTGTGTG | |
| GATCTCCTAGGGGCCCATGGCTCGAG | | CTTAACATTAGTACCAGTATCGACAAAGGACACAC | |
| CTAGAGGATCCCCGGGTACCGAGCTCGAATT | | GTAATCATGGTCATAGCTGTTTCCTGTGTG | 0 |
| CTAGAGGATCCCCGGGTACCGAGCTC | | TAATCATGGTCATAGCTGTTTCCTGTGTG | 6 |
| CTAGAGGATCCCCGGGTAC | | ATCATGGTCATAGCTGTTTCCTGTGTG | 15 |
| CTAGAGGATCCCCGGGTAC | | GTCATAGCTGTTTCCTGTGTG | 21 |
| CTAGAGGATCCCCGGGT | | CATAGCTGTTTCCTGTGTG | 25 |
| GCATGCCTGCAGGTC-35 | | TGTGTG | 58 |
| CTA | | +35 TGTTATCCGCTCACA | 61 |
| CCAACGTTGCATGCC-43 | | TG | 71 |
| CTA | | +47 ACAATTCCACACAAC | 73 |
| ACGCCAGGGTTTTCC-89 | | +71 GGAAGCATAAAGTGT | 158 |

Substrate

Substrate

TAM1 CTRL

| -30 | 0 | 1 | +30 | Deletion size |
|---|---|---|---|---|
| CTAGAGGATCCCCGGGTACCGAGCTCGAATT | | GTAATCATGGTCATAGCTGTTTCCTGTGTG | | (bp) |
| GATCTCCTAGGGGCCCATGGCTCGAG | | CTTAACATTAGTACCAGTATCGACAAAGGACACAC | | |
| CTAGAGGATCCCCGGGTACCGAGCTCGAATT | | GTAATCATGGTCATAGCTGTTTCCTGTGTG | | 0 |
| CTAGAGGATCCCCGGGTACCGAGCTCG | | GTAATCATGGTCATAGCTGTTTCCTGTGTG | | 4 |
| CTAGAGGATCCCCGGGTAC | | AATCATGGTCATAGCTGTTTCCTGTGTG | | 14 |
| CTAGAGGATCCCCGGGTAC | | ATCATGGTCATAGCTGTTTCCTGTGTG | | 15 |
| CTAGAGGATCCCCGGG | | CATAGCTGTTTCCTGTGTG | | 26 |
| CTAGAGGATCCCCGGG | | TAGCTGTTTCCTGTGTG | | 28 |
| GCATGCCTGCAGGTC -35 | | CTGTGTG | | 57 |
| ACGTTGCATGCCTGC -40 | | G | | 69 |
| CCAACGTTGCATGCC -43 | | TG | | 71 |
| CTA | | +47 ACAATTCCACACAAC | | 73 |
| CTA | | +60 CATACGAGCCGGAAG | | 87 |
| CTA | | +86 AAAGCCTGGGGTGCC | | 111 |
| CTA | | +93 GGGGTGCCTAATGAG | | 118 |
| CTA | | +96 GTGCCTAATGAGTGA | | 121 |
| CATGCCTGCAGGTCG -34 | | +123 TAATTGCGTTGCGCT | | 155 |
| CGATTAAGTTGGGTA -104 | | +87 AAGCCTGGGGTGCCT | | 139 |
| TACCGCATCAGGCG -216 | | +75 GCATAAAGTGTAAAG | | 289 |
| TACCGCATCAGGCG -216 | | +77 ATAAAGTGTAAAGCC | | 291 |
| ATGTGCTGCAAGGCG -117 | | +215 TTGCGTATTGGGCGC | | 330 |
| ATGTGCTGCAAGGCG -117 | | +217 GCGTATTGGGCGCTC | | 333 |
| CATTCAGGCTGCGCA -193 | | +224 GGGCGCTCTTCCGCT | | 415 |
| GCATCAGGCGCCATT -211 | | +272 CGGCTGCGGCGAGCG | | 482 |

TAM1 L67+ABT

| -30 | 0 | 1 | +30 | Deletion size |
|---|---|---|---|---|
| CTAGAGGATCCCCGGGTACCGAGCTCGAATT | | GTAATCATGGTCATAGCTGTTTCCTGTGTG | | (bp) |
| GATCTCCTAGGGGCCCATGGCTCGAG | | CTTAACATTAGTACCAGTATCGACAAAGGACACAC | | |
| CTAGAGGATCCCCGGGTACCGAGCTCGAATT | | GTAATCATGGTCATAGCTGTTTCCTGTGTG | | 0 |
| CTAGAGGATCCCCGGGTACCGAGCTCG | | GTAATCATGGTCATAGCTGTTTCCTGTGTG | | 4 |
| CTAGAGGATCCCCGGGTACCGAGCTC | | TAATCATGGTCATAGCTGTTTCCTGTGTG | | 6 |
| CTAGAGGATCCCCGGGTAC | | AATCATGGTCATAGCTGTTTCCTGTGTG | | 14 |
| CTAGAGGATCCCCGGGTAC | | ATCATGGTCATAGCTGTTTCCTGTGTG | | 15 |
| CTAGAGGATCCCCGGGTAC | | GTCATAGCTGTTTCCTGTGTG | | 21 |
| CTAGAGGATCCCCGGG | | TAGCTGTTTCCTGTGTG | | 28 |
| CTAGAGGATCCCCGG | | TAGCTGTTTCCTGTGTG | | 29 |
| CTA | | +35 TGTTATCCGCTCACA | | 61 |
| CCAACGTTGCATGCC -43 | | TG | | 71 |
| CATGCCTGCAGGTCG -34 | | +123 TAATTGCGTTGCGCT | | 155 |
| AGTTGGGTAACGCCA -98 | | +170 TGCCAGCTGCATTAA | | 266 |

FIGURE 8C

SEQUENCE LISTING

```
<160> NUMBER OF SEQ ID NOS: 202

<210> SEQ ID NO 1
<211> LENGTH: 31
<212> TYPE: DNA
<213> ORGANISM: Artificial Sequence
<220> FEATURE:
<223> OTHER INFORMATION: Sequencing of DSB repair junction in MCF10A
      with CTRL

<400> SEQUENCE: 1
ctagaggatc cccgggtacc gagctcgaat t                                      31

<210> SEQ ID NO 2
<211> LENGTH: 30
<212> TYPE: DNA
<213> ORGANISM: Artificial Sequence
<220> FEATURE:
<223> OTHER INFORMATION: Sequencing of DSB repair junction in MCF10A
      with CTRL

<400> SEQUENCE: 2
gtaatcatgg tcatagctgt ttcctgtgtg                                        30

<210> SEQ ID NO 3
<211> LENGTH: 26
<212> TYPE: DNA
<213> ORGANISM: Artificial Sequence
<220> FEATURE:
<223> OTHER INFORMATION: Sequencing of DSB repair junction in MCF10A
      with CTRL

<400> SEQUENCE: 3
gatctcctag gggcccatgg ctcgag                                            26
```

<210> SEQ ID NO 4
<211> LENGTH: 35
<212> TYPE: DNA
<213> ORGANISM: Artificial Sequence
<220> FEATURE:
<223> OTHER INFORMATION: Sequencing of DSB repair junction in MCF10A
      with CTRL

<400> SEQUENCE: 4
cttaacatta gtaccagtat cgacaaagga cacac                              35

<210> SEQ ID NO 5
<211> LENGTH: 31
<212> TYPE: DNA
<213> ORGANISM: Artificial Sequence
<220> FEATURE:
<223> OTHER INFORMATION: Sequencing of DSB repair junction in MCF10A
      with CTRL

<400> SEQUENCE: 5
ctagaggatc cccgggtacc gagctcgaat t                                  31

<210> SEQ ID NO 6
<211> LENGTH: 30
<212> TYPE: DNA
<213> ORGANISM: Artificial Sequence
<220> FEATURE:
<223> OTHER INFORMATION: Sequencing of DSB repair junction in MCF10A
      with CTRL

<400> SEQUENCE: 6
gtaatcatgg tcatagctgt ttcctgtgtg                                    30

<210> SEQ ID NO 7
<211> LENGTH: 30
<212> TYPE: DNA
<213> ORGANISM: Artificial Sequence
<220> FEATURE:
<223> OTHER INFORMATION: Sequencing of DSB repair junction in MCF10A
      with CTRL

<400> SEQUENCE: 7
ctagaggatc cccgggtacc gagctcgaat                                    30

<210> SEQ ID NO 8
<211> LENGTH: 30
<212> TYPE: DNA
<213> ORGANISM: Artificial Sequence
<220> FEATURE:
<223> OTHER INFORMATION: Sequencing of DSB repair junction in MCF10A
      with CTRL

<400> SEQUENCE: 8
gtaatcatgg tcatagctgt ttcctgtgtg                                    30

<210> SEQ ID NO 9
<211> LENGTH: 27
<212> TYPE: DNA
<213> ORGANISM: Artificial Sequence
<220> FEATURE:
<223> OTHER INFORMATION: Sequencing of DSB repair junction in MCF10A
      with CTRL

<400> SEQUENCE: 9
ctagaggatc cccgggtacc gagctcg                                       27

```
<210> SEQ ID NO 10
<211> LENGTH: 30
<212> TYPE: DNA
<213> ORGANISM: Artificial Sequence
<220> FEATURE:
<223> OTHER INFORMATION: Sequencing of DSB repair junction in MCF10A
      with CTRL

<400> SEQUENCE: 10
gtaatcatgg tcatagctgt ttcctgtgtg                                       30

<210> SEQ ID NO 11
<211> LENGTH: 26
<212> TYPE: DNA
<213> ORGANISM: Artificial Sequence
<220> FEATURE:
<223> OTHER INFORMATION: Sequencing of DSB repair junction in MCF10A
      with CTRL

<400> SEQUENCE: 11
ctagaggatc cccgggtacc gagctc                                           26

<210> SEQ ID NO 12
<211> LENGTH: 29
<212> TYPE: DNA
<213> ORGANISM: Artificial Sequence
<220> FEATURE:
<223> OTHER INFORMATION: Sequencing of DSB repair junction in MCF10A
      with CTRL

<400> SEQUENCE: 12
taatcatggt catagctgtt tcctgtgtg                                        29

<210> SEQ ID NO 13
<211> LENGTH: 29
<212> TYPE: DNA
<213> ORGANISM: Artificial Sequence
<220> FEATURE:
<223> OTHER INFORMATION: Sequencing of DSB repair junction in MCF10A
      with CTRL

<400> SEQUENCE: 13
ctagaggatc cccgggtacc gagctcgaa                                        29

<210> SEQ ID NO 14
<211> LENGTH: 23
<212> TYPE: DNA
<213> ORGANISM: Artificial Sequence
<220> FEATURE:
<223> OTHER INFORMATION: Sequencing of DSB repair junction in MCF10A
      with CTRL

<400> SEQUENCE: 14
tggtcatagc tgtttcctgt gtg                                              23

<210> SEQ ID NO 15
<211> LENGTH: 23
<212> TYPE: DNA
<213> ORGANISM: Artificial Sequence
<220> FEATURE:
<223> OTHER INFORMATION: Sequencing of DSB repair junction in MCF10A
      with CTRL

<400> SEQUENCE: 15
ctagaggatc cccgggtacc gag                                              23
```

```
<210> SEQ ID NO 16
<211> LENGTH: 28
<212> TYPE: DNA
<213> ORGANISM: Artificial Sequence
<220> FEATURE:
<223> OTHER INFORMATION: Sequencing of DSB repair junction in MCF10A
      with CTRL

<400> SEQUENCE: 16
aatcatggtc atagctgttt cctgtgtg                                      28

<210> SEQ ID NO 17
<211> LENGTH: 19
<212> TYPE: DNA
<213> ORGANISM: Artificial Sequence
<220> FEATURE:
<223> OTHER INFORMATION: Sequencing of DSB repair junction in MCF10A
      with CTRL

<400> SEQUENCE: 17
ctagaggatc cccgggtac                                                19

<210> SEQ ID NO 18
<211> LENGTH: 27
<212> TYPE: DNA
<213> ORGANISM: Artificial Sequence
<220> FEATURE:
<223> OTHER INFORMATION: Sequencing of DSB repair junction in MCF10A
      with CTRL

<400> SEQUENCE: 18
atcatggtca tagctgtttc ctgtgtg                                       27

<210> SEQ ID NO 19
<211> LENGTH: 19
<212> TYPE: DNA
<213> ORGANISM: Artificial Sequence
<220> FEATURE:
<223> OTHER INFORMATION: Sequencing of DSB repair junction in MCF10A
      with CTRL

<400> SEQUENCE: 19
ctagaggatc cccgggtac                                                19

<210> SEQ ID NO 20
<211> LENGTH: 26
<212> TYPE: DNA
<213> ORGANISM: Artificial Sequence
<220> FEATURE:
<223> OTHER INFORMATION: Sequencing of DSB repair junction in MCF10A
      with CTRL

<400> SEQUENCE: 20
tcatggtcat agctgtttcc tgtgtg                                        26

<210> SEQ ID NO 21
<211> LENGTH: 19
<212> TYPE: DNA
<213> ORGANISM: Artificial Sequence
<220> FEATURE:
<223> OTHER INFORMATION: Sequencing of DSB repair junction in MCF10A
      with CTRL

<400> SEQUENCE: 21
ctagaggatc cccgggtac                                                19

<210> SEQ ID NO 22
```

```
<211> LENGTH: 21
<212> TYPE: DNA
<213> ORGANISM: Artificial Sequence
<220> FEATURE:
<223> OTHER INFORMATION: Sequencing of DSB repair junction in MCF10A
      with CTRL

<400> SEQUENCE: 22
gtcatagctg tttcctgtgt g                                              21

<210> SEQ ID NO 23
<211> LENGTH: 19
<212> TYPE: DNA
<213> ORGANISM: Artificial Sequence
<220> FEATURE:
<223> OTHER INFORMATION: Sequencing of DSB repair junction in MCF10A
      with CTRL

<400> SEQUENCE: 23
ctagaggatc cccgggtac                                                 19

<210> SEQ ID NO 24
<211> LENGTH: 20
<212> TYPE: DNA
<213> ORGANISM: Artificial Sequence
<220> FEATURE:
<223> OTHER INFORMATION: Sequencing of DSB repair junction in MCF10A
      with CTRL

<400> SEQUENCE: 24
tcatagctgt ttcctgtgtg                                                20

<210> SEQ ID NO 25
<211> LENGTH: 10
<212> TYPE: DNA
<213> ORGANISM: Artificial Sequence
<220> FEATURE:
<223> OTHER INFORMATION: Sequencing of DSB repair junction in MCF10A
      with CTRL

<400> SEQUENCE: 25
ctagaggatc                                                           10

<210> SEQ ID NO 26
<211> LENGTH: 14
<212> TYPE: DNA
<213> ORGANISM: Artificial Sequence
<220> FEATURE:
<223> OTHER INFORMATION: Sequencing of DSB repair junction in MCF10A
      with CTRL

<400> SEQUENCE: 26
ctgtttcctg tgtg                                                      14

<210> SEQ ID NO 27
<211> LENGTH: 15
<212> TYPE: DNA
<213> ORGANISM: Artificial Sequence
<220> FEATURE:
<223> OTHER INFORMATION: Sequencing of DSB repair junction in MCF10A
      with CTRL

<400> SEQUENCE: 27
ttgcatgcct gcagg                                                     15

<210> SEQ ID NO 28
<211> LENGTH: 9
```

-continued

```
<212> TYPE: DNA
<213> ORGANISM: Artificial Sequence
<220> FEATURE:
<223> OTHER INFORMATION: Sequencing of DSB repair junction in MCF10A
      with CTRL

<400> SEQUENCE: 28 tcctgtgtg                                                              9

<210> SEQ ID NO 29
<211> LENGTH: 15
<212> TYPE: DNA
<213> ORGANISM: Artificial Sequence
<220> FEATURE:
<223> OTHER INFORMATION: Sequencing of DSB repair junction in MCF10A
      with CTRL

<400> SEQUENCE: 29
ccaacgttgc atgcc                                                      15

<210> SEQ ID NO 30
<211> LENGTH: 2
<212> TYPE: DNA
<213> ORGANISM: Artificial Sequence
<220> FEATURE:
<223> OTHER INFORMATION: Sequencing of DSB repair junction in MCF10A
      with CTRL

<400> SEQUENCE: 30 tg                                                                     2

<210> SEQ ID NO 31
<211> LENGTH: 15
<212> TYPE: DNA
<213> ORGANISM: Artificial Sequence
<220> FEATURE:
<223> OTHER INFORMATION: Sequencing of DSB repair junction in MCF10A
      with CTRL

<400> SEQUENCE: 31
ccaacgttgc atgcc                                                      15

<210> SEQ ID NO 32
<211> LENGTH: 15
<212> TYPE: DNA
<213> ORGANISM: Artificial Sequence
<220> FEATURE:
<223> OTHER INFORMATION: Sequencing of DSB repair junction in MCF10A
      with CTRL

<400> SEQUENCE: 32
aaattgttat ccgct                                                      15

<210> SEQ ID NO 33
<211> LENGTH: 15
<212> TYPE: DNA
<213> ORGANISM: Artificial Sequence
<220> FEATURE:
<223> OTHER INFORMATION: Sequencing of DSB repair junction in MCF10A
      with CTRL

<400> SEQUENCE: 33
acgccagggt tttcc                                                      15

<210> SEQ ID NO 34
<211> LENGTH: 15
<212> TYPE: DNA
```

```
<213> ORGANISM: Artificial Sequence
<220> FEATURE:
<223> OTHER INFORMATION: Sequencing of DSB repair junction in MCF10A
      with CTRL

<400> SEQUENCE: 34
ggaagcataa agtgt                                                        15

<210> SEQ ID NO 35
<211> LENGTH: 15
<212> TYPE: DNA
<213> ORGANISM: Artificial Sequence
<220> FEATURE:
<223> OTHER INFORMATION: Sequencing of DSB repair junction in MCF10A
      with CTRL

<400> SEQUENCE: 35
ccagctggcg aaagg                                                        15

<210> SEQ ID NO 36
<211> LENGTH: 15
<212> TYPE: DNA
<213> ORGANISM: Artificial Sequence
<220> FEATURE:
<223> OTHER INFORMATION: Sequencing of DSB repair junction in MCF10A
      with CTRL

<400> SEQUENCE: 36
ggggtgccta atgag                                                        15

<210> SEQ ID NO 37
<211> LENGTH: 31
<212> TYPE: DNA
<213> ORGANISM: Artificial Sequence
<220> FEATURE:
<223> OTHER INFORMATION: Sequencing of DSB repair junction in MCF10A
      with L67+ABT888

<400> SEQUENCE: 37
ctagaggatc cccgggtacc gagctcgaat t                                      31

<210> SEQ ID NO 38
<211> LENGTH: 30
<212> TYPE: DNA
<213> ORGANISM: Artificial Sequence
<220> FEATURE:
<223> OTHER INFORMATION: Sequencing of DSB repair junction in MCF10A
      with L67+ABT888

<400> SEQUENCE: 38
gtaatcatgg tcatagctgt ttcctgtgtg                                        30

<210> SEQ ID NO 39
<211> LENGTH: 26
<212> TYPE: DNA
<213> ORGANISM: Artificial Sequence
<220> FEATURE:
<223> OTHER INFORMATION: Sequencing of DSB repair junction in MCF10A
      with L67+ABT888

<400> SEQUENCE: 39
gatctcctag gggcccatgg ctcgag                                            26

<210> SEQ ID NO 40
<211> LENGTH: 35
<212> TYPE: DNA
<213> ORGANISM: Artificial Sequence
```

```
<220> FEATURE:
<223> OTHER INFORMATION: Sequencing of DSB repair junction in MCF10A
      with L67+ABT888

<400> SEQUENCE: 40
cttaacatta gtaccagtat cgacaaagga cacac                              35

<210> SEQ ID NO 41
<211> LENGTH: 27
<212> TYPE: DNA
<213> ORGANISM: Artificial Sequence
<220> FEATURE:
<223> OTHER INFORMATION: Sequencing of DSB repair junction in MCF10A
      with L67+ABT888

<400> SEQUENCE: 41
ctagaggatc cccgggtacc gagctcg                                       27

<210> SEQ ID NO 42
<211> LENGTH: 30
<212> TYPE: DNA
<213> ORGANISM: Artificial Sequence
<220> FEATURE:
<223> OTHER INFORMATION: Sequencing of DSB repair junction in MCF10A
      with L67+ABT888

<400> SEQUENCE: 42
gtaatcatgg tcatagctgt ttcctgtgtg                                    30

<210> SEQ ID NO 43
<211> LENGTH: 27
<212> TYPE: DNA
<213> ORGANISM: Artificial Sequence
<220> FEATURE:
<223> OTHER INFORMATION: Sequencing of DSB repair junction in MCF10A
      with L67+ABT888

<400> SEQUENCE: 43
ctagaggatc cccgggtacc gagctcg                                       27

<210> SEQ ID NO 44
<211> LENGTH: 29
<212> TYPE: DNA
<213> ORGANISM: Artificial Sequence
<220> FEATURE:
<223> OTHER INFORMATION: Sequencing of DSB repair junction in MCF10A
      with L67+ABT888

<400> SEQUENCE: 44
taatcatggt catagctgtt tcctgtgtg                                     29

<210> SEQ ID NO 45
<211> LENGTH: 26
<212> TYPE: DNA
<213> ORGANISM: Artificial Sequence
<220> FEATURE:
<223> OTHER INFORMATION: Sequencing of DSB repair junction in MCF10A
      with L67+ABT888

<400> SEQUENCE: 45
ctagaggatc cccgggtacc gagctc                                        26

<210> SEQ ID NO 46
<211> LENGTH: 29
<212> TYPE: DNA
<213> ORGANISM: Artificial Sequence
<220> FEATURE:
```

<223> OTHER INFORMATION: Sequencing of DSB repair junction in MCF10A
      with L67+ABT888

<400> SEQUENCE: 46
taatcatggt catagctgtt tcctgtgtg                                     29

<210> SEQ ID NO 47
<211> LENGTH: 29
<212> TYPE: DNA
<213> ORGANISM: Artificial Sequence
<220> FEATURE:
<223> OTHER INFORMATION: Sequencing of DSB repair junction in MCF10A
      with L67+ABT888

<400> SEQUENCE: 47
ctagaggatc cccgggtacc gagctcgaa                                     29

<210> SEQ ID NO 48
<211> LENGTH: 23
<212> TYPE: DNA
<213> ORGANISM: Artificial Sequence
<220> FEATURE:
<223> OTHER INFORMATION: Sequencing of DSB repair junction in MCF10A
      with L67+ABT888

<400> SEQUENCE: 48
tggtcatagc tgtttcctgt gtg                                           23

<210> SEQ ID NO 49
<211> LENGTH: 19
<212> TYPE: DNA
<213> ORGANISM: Artificial Sequence
<220> FEATURE:
<223> OTHER INFORMATION: Sequencing of DSB repair junction in MCF10A
      with L67+ABT888

<400> SEQUENCE: 49
ctagaggatc cccgggtac                                                19

<210> SEQ ID NO 50
<211> LENGTH: 27
<212> TYPE: DNA
<213> ORGANISM: Artificial Sequence
<220> FEATURE:
<223> OTHER INFORMATION: Sequencing of DSB repair junction in MCF10A
      with L67+ABT888

<400> SEQUENCE: 50
atcatggtca tagctgtttc ctgtgtg                                       27

<210> SEQ ID NO 51
<211> LENGTH: 20
<212> TYPE: DNA
<213> ORGANISM: Artificial Sequence
<220> FEATURE:
<223> OTHER INFORMATION: Sequencing of DSB repair junction in MCF10A
      with L67+ABT888

<400> SEQUENCE: 51
ctagaggatc cccgggtacc                                               20

<210> SEQ ID NO 52
<211> LENGTH: 24
<212> TYPE: DNA
<213> ORGANISM: Artificial Sequence
<220> FEATURE:
<223> OTHER INFORMATION: Sequencing of DSB repair junction in MCF10A with L67+ABT888

<400> SEQUENCE: 52
atggtcatag ctgtttcctg tgtg                                              24

<210> SEQ ID NO 53
<211> LENGTH: 19
<212> TYPE: DNA
<213> ORGANISM: Artificial Sequence
<220> FEATURE:
<223> OTHER INFORMATION: Sequencing of DSB repair junction in MCF10A
      with L67+ABT888

<400> SEQUENCE: 53
ctagaggatc cccgggtac                                                    19

<210> SEQ ID NO 54
<211> LENGTH: 24
<212> TYPE: DNA
<213> ORGANISM: Artificial Sequence
<220> FEATURE:
<223> OTHER INFORMATION: Sequencing of DSB repair junction in MCF10A
      with L67+ABT888

<400> SEQUENCE: 54
atggtcatag ctgtttcctg tgtg                                              24

<210> SEQ ID NO 55
<211> LENGTH: 19
<212> TYPE: DNA
<213> ORGANISM: Artificial Sequence
<220> FEATURE:
<223> OTHER INFORMATION: Sequencing of DSB repair junction in MCF10A
      with L67+ABT888

<400> SEQUENCE: 55
ctagaggatc cccgggtac                                                    19

<210> SEQ ID NO 56
<211> LENGTH: 21
<212> TYPE: DNA
<213> ORGANISM: Artificial Sequence
<220> FEATURE:
<223> OTHER INFORMATION: Sequencing of DSB repair junction in MCF10A
      with L67+ABT888

<400> SEQUENCE: 56
gtcatagctg tttcctgtgt g                                                 21

<210> SEQ ID NO 57
<211> LENGTH: 17
<212> TYPE: DNA
<213> ORGANISM: Artificial Sequence
<220> FEATURE:
<223> OTHER INFORMATION: Sequencing of DSB repair junction in MCF10A
      with L67+ABT888

<400> SEQUENCE: 57
ctagaggatc cccgggt                                                      17

<210> SEQ ID NO 58
<211> LENGTH: 19
<212> TYPE: DNA
<213> ORGANISM: Artificial Sequence
<220> FEATURE:
<223> OTHER INFORMATION: Sequencing of DSB repair junction in MCF10A
      with L67+ABT888

-continued

<400> SEQUENCE: 58
catagctgtt tcctgtgtg					19

<210> SEQ ID NO 59
<211> LENGTH: 15
<212> TYPE: DNA
<213> ORGANISM: Artificial Sequence
<220> FEATURE:
<223> OTHER INFORMATION: Sequencing of DSB repair junction in MCF10A
      with L67+ABT888

<400> SEQUENCE: 59
ctagaggatc cccgg					15

<210> SEQ ID NO 60
<211> LENGTH: 19
<212> TYPE: DNA
<213> ORGANISM: Artificial Sequence
<220> FEATURE:
<223> OTHER INFORMATION: Sequencing of DSB repair junction in MCF10A
      with L67+ABT888

<400> SEQUENCE: 60
catagctgtt tcctgtgtg					19

<210> SEQ ID NO 61
<211> LENGTH: 15
<212> TYPE: DNA
<213> ORGANISM: Artificial Sequence
<220> FEATURE:
<223> OTHER INFORMATION: Sequencing of DSB repair junction in MCF10A
      with L67+ABT888

<400> SEQUENCE: 61
acgttgcatg cctgc					15

<210> SEQ ID NO 62
<211> LENGTH: 3
<212> TYPE: DNA
<213> ORGANISM: Artificial Sequence
<220> FEATURE:
<223> OTHER INFORMATION: Sequencing of DSB repair junction in MCF10A
      with L67+ABT888

<400> SEQUENCE: 62 gtg					3

<210> SEQ ID NO 63
<211> LENGTH: 15
<212> TYPE: DNA
<213> ORGANISM: Artificial Sequence
<220> FEATURE:
<223> OTHER INFORMATION: Sequencing of DSB repair junction in MCF10A
      with L67+ABT888

<400> SEQUENCE: 63
acgccagggt tttcc					15

<210> SEQ ID NO 64
<211> LENGTH: 15
<212> TYPE: DNA
<213> ORGANISM: Artificial Sequence
<220> FEATURE:
<223> OTHER INFORMATION: Sequencing of DSB repair junction in MCF10A
      with L67+ABT888

```
<400> SEQUENCE: 64
ggaagcataa agtgt                                                    15

<210> SEQ ID NO 65
<211> LENGTH: 31
<212> TYPE: DNA
<213> ORGANISM: Artificial Sequence
<220> FEATURE:
<223> OTHER INFORMATION: Sequencing of DSB repair junction in MCF7 with
      CTRL

<400> SEQUENCE: 65
ctagaggatc cccgggtacc gagctcgaat t                                  31

<210> SEQ ID NO 66
<211> LENGTH: 30
<212> TYPE: DNA
<213> ORGANISM: Artificial Sequence
<220> FEATURE:
<223> OTHER INFORMATION: Sequencing of DSB repair junction in MCF7 with
      CTRL

<400> SEQUENCE: 66
gtaatcatgg tcatagctgt ttcctgtgtg                                    30

<210> SEQ ID NO 67
<211> LENGTH: 26
<212> TYPE: DNA
<213> ORGANISM: Artificial Sequence
<220> FEATURE:
<223> OTHER INFORMATION: Sequencing of DSB repair junction in MCF7 with
      CTRL

<400> SEQUENCE: 67
gatctcctag gggcccatgg ctcgag                                        26

<210> SEQ ID NO 68
<211> LENGTH: 35
<212> TYPE: DNA
<213> ORGANISM: Artificial Sequence
<220> FEATURE:
<223> OTHER INFORMATION: Sequencing of DSB repair junction in MCF7 with
      CTRL

<400> SEQUENCE: 68
cttaacatta gtaccagtat cgacaaagga cacac                              35

<210> SEQ ID NO 69
<211> LENGTH: 31
<212> TYPE: DNA
<213> ORGANISM: Artificial Sequence
<220> FEATURE:
<223> OTHER INFORMATION: Sequencing of DSB repair junction in MCF7 with
      CTRL

<400> SEQUENCE: 69
ctagaggatc cccgggtacc gagctcgaat t                                  31

<210> SEQ ID NO 70
<211> LENGTH: 30
<212> TYPE: DNA
<213> ORGANISM: Artificial Sequence
<220> FEATURE:
<223> OTHER INFORMATION: Sequencing of DSB repair junction in MCF7 with
      CTRL

<400> SEQUENCE: 70
```
gtaatcatgg tcatagctgt ttcctgtgtg                                    30

<210> SEQ ID NO 71
<211> LENGTH: 27
<212> TYPE: DNA
<213> ORGANISM: Artificial Sequence
<220> FEATURE:
<223> OTHER INFORMATION: Sequencing of DSB repair junction in MCF7 with
      CTRL

<400> SEQUENCE: 71
ctagaggatc cccgggtacc gagctcg                                       27

<210> SEQ ID NO 72
<211> LENGTH: 30
<212> TYPE: DNA
<213> ORGANISM: Artificial Sequence
<220> FEATURE:
<223> OTHER INFORMATION: Sequencing of DSB repair junction in MCF7 with
      CTRL

<400> SEQUENCE: 72
gtaatcatgg tcatagctgt ttcctgtgtg                                    30

<210> SEQ ID NO 73
<211> LENGTH: 26
<212> TYPE: DNA
<213> ORGANISM: Artificial Sequence
<220> FEATURE:
<223> OTHER INFORMATION: Sequencing of DSB repair junction in MCF7 with
      CTRL

<400> SEQUENCE: 73
ctagaggatc cccgggtacc gagctc                                        26

<210> SEQ ID NO 74
<211> LENGTH: 29
<212> TYPE: DNA
<213> ORGANISM: Artificial Sequence
<220> FEATURE:
<223> OTHER INFORMATION: Sequencing of DSB repair junction in MCF7 with
      CTRL

<400> SEQUENCE: 74
taatcatggt catagctgtt tcctgtgtg                                     29

<210> SEQ ID NO 75
<211> LENGTH: 19
<212> TYPE: DNA
<213> ORGANISM: Artificial Sequence
<220> FEATURE:
<223> OTHER INFORMATION: Sequencing of DSB repair junction in MCF7 with
      CTRL

<400> SEQUENCE: 75
ctagaggatc cccgggtac                                                19

<210> SEQ ID NO 76
<211> LENGTH: 27
<212> TYPE: DNA
<213> ORGANISM: Artificial Sequence
<220> FEATURE:
<223> OTHER INFORMATION: Sequencing of DSB repair junction in MCF7 with
      CTRL

<400> SEQUENCE: 76
atcatggtca tagctgtttc ctgtgtg    27

<210> SEQ ID NO 77
<211> LENGTH: 19
<212> TYPE: DNA
<213> ORGANISM: Artificial Sequence
<220> FEATURE:
<223> OTHER INFORMATION: Sequencing of DSB repair junction in MCF7 with
      CTRL

<400> SEQUENCE: 77
ctagaggatc cccgggtac    19

<210> SEQ ID NO 78
<211> LENGTH: 21
<212> TYPE: DNA
<213> ORGANISM: Artificial Sequence
<220> FEATURE:
<223> OTHER INFORMATION: Sequencing of DSB repair junction in MCF7 with
      CTRL

<400> SEQUENCE: 78
gtcatagctg tttcctgtgt g    21

<210> SEQ ID NO 79
<211> LENGTH: 17
<212> TYPE: DNA
<213> ORGANISM: Artificial Sequence
<220> FEATURE:
<223> OTHER INFORMATION: Sequencing of DSB repair junction in MCF7 with
      CTRL

<400> SEQUENCE: 79
ctagaggatc cccgggt    17

<210> SEQ ID NO 80
<211> LENGTH: 19
<212> TYPE: DNA
<213> ORGANISM: Artificial Sequence
<220> FEATURE:
<223> OTHER INFORMATION: Sequencing of DSB repair junction in MCF7 with
      CTRL

<400> SEQUENCE: 80
catagctgtt tcctgtgtg    19

<210> SEQ ID NO 81
<211> LENGTH: 16
<212> TYPE: DNA
<213> ORGANISM: Artificial Sequence
<220> FEATURE:
<223> OTHER INFORMATION: Sequencing of DSB repair junction in MCF7 with
      CTRL

<400> SEQUENCE: 81
ctagaggatc cccggg    16

<210> SEQ ID NO 82
<211> LENGTH: 19
<212> TYPE: DNA
<213> ORGANISM: Artificial Sequence
<220> FEATURE:
<223> OTHER INFORMATION: Sequencing of DSB repair junction in MCF7 with
      CTRL

<400> SEQUENCE: 82
catagctgtt tcctgtgtg    19

<210> SEQ ID NO 83
<211> LENGTH: 15
<212> TYPE: DNA
<213> ORGANISM: Artificial Sequence
<220> FEATURE:
<223> OTHER INFORMATION: Sequencing of DSB repair junction in MCF7 with
      CTRL

<400> SEQUENCE: 83
gcatgcctgc aggtc                                                        15

<210> SEQ ID NO 84
<211> LENGTH: 7
<212> TYPE: DNA
<213> ORGANISM: Artificial Sequence
<220> FEATURE:
<223> OTHER INFORMATION: Sequencing of DSB repair junction in MCF7 with
      CTRL

<400> SEQUENCE: 84 ctgtgtg                                                                  7

<210> SEQ ID NO 85
<211> LENGTH: 15
<212> TYPE: DNA
<213> ORGANISM: Artificial Sequence
<220> FEATURE:
<223> OTHER INFORMATION: Sequencing of DSB repair junction in MCF7 with
      CTRL

<400> SEQUENCE: 85
acgttgcatg cctgc                                                        15

<210> SEQ ID NO 86
<211> LENGTH: 3
<212> TYPE: DNA
<213> ORGANISM: Artificial Sequence
<220> FEATURE:
<223> OTHER INFORMATION: Sequencing of DSB repair junction in MCF7 with
      CTRL

<400> SEQUENCE: 86 gtg                                                                      3

<210> SEQ ID NO 87
<211> LENGTH: 3
<212> TYPE: DNA
<213> ORGANISM: Artificial Sequence
<220> FEATURE:
<223> OTHER INFORMATION: Sequencing of DSB repair junction in MCF7 with
      CTRL

<400> SEQUENCE: 87 cta                                                                      3

<210> SEQ ID NO 88
<211> LENGTH: 15
<212> TYPE: DNA
<213> ORGANISM: Artificial Sequence
<220> FEATURE:
<223> OTHER INFORMATION: Sequencing of DSB repair junction in MCF7 with
      CTRL

<400> SEQUENCE: 88
acaattccac acaac                                                        15

<210> SEQ ID NO 89
<211> LENGTH: 3
<212> TYPE: DNA
<213> ORGANISM: Artificial Sequence
<220> FEATURE:
<223> OTHER INFORMATION: Sequencing of DSB repair junction in MCF7 with
      CTRL

<400> SEQUENCE: 89 cta                                                                       3

<210> SEQ ID NO 90
<211> LENGTH: 15
<212> TYPE: DNA
<213> ORGANISM: Artificial Sequence
<220> FEATURE:
<223> OTHER INFORMATION: Sequencing of DSB repair junction in MCF7 with
      CTRL

<400> SEQUENCE: 90
aaagcctggg gtgcc                                                         15

<210> SEQ ID NO 91
<211> LENGTH: 15
<212> TYPE: DNA
<213> ORGANISM: Artificial Sequence
<220> FEATURE:
<223> OTHER INFORMATION: Sequencing of DSB repair junction in MCF7 with
      CTRL

<400> SEQUENCE: 91
acgccagggt tttcc                                                         15

<210> SEQ ID NO 92
<211> LENGTH: 15
<212> TYPE: DNA
<213> ORGANISM: Artificial Sequence
<220> FEATURE:
<223> OTHER INFORMATION: Sequencing of DSB repair junction in MCF7 with
      CTRL

<400> SEQUENCE: 92
ccggaagcat aaagt                                                         15

<210> SEQ ID NO 93
<211> LENGTH: 15
<212> TYPE: DNA
<213> ORGANISM: Artificial Sequence
<220> FEATURE:
<223> OTHER INFORMATION: Sequencing of DSB repair junction in MCF7 with
      CTRL

<400> SEQUENCE: 93
agttgggtaa cgcca                                                         15

<210> SEQ ID NO 94
<211> LENGTH: 15
<212> TYPE: DNA
<213> ORGANISM: Artificial Sequence
<220> FEATURE:
<223> OTHER INFORMATION: Sequencing of DSB repair junction in MCF7 with
      CTRL

<400> SEQUENCE: 94
cggaagcata aagtg                                                         15

```
<210> SEQ ID NO 95
<211> LENGTH: 15
<212> TYPE: DNA
<213> ORGANISM: Artificial Sequence
<220> FEATURE:
<223> OTHER INFORMATION: Sequencing of DSB repair junction in MCF7 with
      CTRL

<400> SEQUENCE: 95
agttgggtaa cgcca                                                    15

<210> SEQ ID NO 96
<211> LENGTH: 15
<212> TYPE: DNA
<213> ORGANISM: Artificial Sequence
<220> FEATURE:
<223> OTHER INFORMATION: Sequencing of DSB repair junction in MCF7 with
      CTRL

<400> SEQUENCE: 96
gctaactcac attaa                                                    15

<210> SEQ ID NO 97
<211> LENGTH: 15
<212> TYPE: DNA
<213> ORGANISM: Artificial Sequence
<220> FEATURE:
<223> OTHER INFORMATION: Sequencing of DSB repair junction in MCF7 with
      CTRL

<400> SEQUENCE: 97
agttgggtaa cgcca                                                    15

<210> SEQ ID NO 98
<211> LENGTH: 15
<212> TYPE: DNA
<213> ORGANISM: Artificial Sequence
<220> FEATURE:
<223> OTHER INFORMATION: Sequencing of DSB repair junction in MCF7 with
      CTRL

<400> SEQUENCE: 98
tgccagctgc attaa                                                    15

<210> SEQ ID NO 99
<211> LENGTH: 15
<212> TYPE: DNA
<213> ORGANISM: Artificial Sequence
<220> FEATURE:
<223> OTHER INFORMATION: Sequencing of DSB repair junction in MCF7 with
      CTRL

<400> SEQUENCE: 99
agttgggtaa cgcca                                                    15

<210> SEQ ID NO 100
<211> LENGTH: 15
<212> TYPE: DNA
<213> ORGANISM: Artificial Sequence
<220> FEATURE:
<223> OTHER INFORMATION: Sequencing of DSB repair junction in MCF7 with
      CTRL

<400> SEQUENCE: 100
gaatcggcca acgcg                                                    15

<210> SEQ ID NO 101
```

```
<211> LENGTH: 15
<212> TYPE: DNA
<213> ORGANISM: Artificial Sequence
<220> FEATURE:
<223> OTHER INFORMATION: Sequencing of DSB repair junction in MCF7 with
      CTRL

<400> SEQUENCE: 101
ccattcaggc tgcgc                                                        15

<210> SEQ ID NO 102
<211> LENGTH: 15
<212> TYPE: DNA
<213> ORGANISM: Artificial Sequence
<220> FEATURE:
<223> OTHER INFORMATION: Sequencing of DSB repair junction in MCF7 with
      CTRL

<400> SEQUENCE: 102
cggccaacgc gcggg                                                        15

<210> SEQ ID NO 103
<211> LENGTH: 31
<212> TYPE: DNA
<213> ORGANISM: Artificial Sequence
<220> FEATURE:
<223> OTHER INFORMATION: Sequencing of DSB repair junction in MCF7 with
      L67+ABT888

<400> SEQUENCE: 103
ctagaggatc cccgggtacc gagctcgaat t                                      31

<210> SEQ ID NO 104
<211> LENGTH: 30
<212> TYPE: DNA
<213> ORGANISM: Artificial Sequence
<220> FEATURE:
<223> OTHER INFORMATION: Sequencing of DSB repair junction in MCF7 with
      L67+ABT888

<400> SEQUENCE: 104
gtaatcatgg tcatagctgt ttcctgtgtg                                        30

<210> SEQ ID NO 105
<211> LENGTH: 26
<212> TYPE: DNA
<213> ORGANISM: Artificial Sequence
<220> FEATURE:
<223> OTHER INFORMATION: Sequencing of DSB repair junction in MCF7 with
      L67+ABT888

<400> SEQUENCE: 105
gatctcctag gggcccatgg ctcgag                                            26

<210> SEQ ID NO 106
<211> LENGTH: 35
<212> TYPE: DNA
<213> ORGANISM: Artificial Sequence
<220> FEATURE:
<223> OTHER INFORMATION: Sequencing of DSB repair junction in MCF7 with
      L67+ABT888

<400> SEQUENCE: 106
cttaacatta gtaccagtat cgacaaagga cacac                                  35

<210> SEQ ID NO 107
<211> LENGTH: 31
```

```
<212> TYPE: DNA
<213> ORGANISM: Artificial Sequence
<220> FEATURE:
<223> OTHER INFORMATION: Sequencing of DSB repair junction in MCF7 with
      L67+ABT888

<400> SEQUENCE: 107
ctagaggatc cccgggtacc gagctcgaat t                                       31

<210> SEQ ID NO 108
<211> LENGTH: 30
<212> TYPE: DNA
<213> ORGANISM: Artificial Sequence
<220> FEATURE:
<223> OTHER INFORMATION: Sequencing of DSB repair junction in MCF7 with
      L67+ABT888

<400> SEQUENCE: 108
gtaatcatgg tcatagctgt ttcctgtgtg                                         30

<210> SEQ ID NO 109
<211> LENGTH: 27
<212> TYPE: DNA
<213> ORGANISM: Artificial Sequence
<220> FEATURE:
<223> OTHER INFORMATION: Sequencing of DSB repair junction in MCF7 with
      L67+ABT888

<400> SEQUENCE: 109
ctagaggatc cccgggtacc gagctcg                                            27

<210> SEQ ID NO 110
<211> LENGTH: 29
<212> TYPE: DNA
<213> ORGANISM: Artificial Sequence
<220> FEATURE:
<223> OTHER INFORMATION: Sequencing of DSB repair junction in MCF7 with
      L67+ABT888

<400> SEQUENCE: 110
taatcatggt catagctgtt tcctgtgtg                                          29

<210> SEQ ID NO 111
<211> LENGTH: 19
<212> TYPE: DNA
<213> ORGANISM: Artificial Sequence
<220> FEATURE:
<223> OTHER INFORMATION: Sequencing of DSB repair junction in MCF7 with
      L67+ABT888

<400> SEQUENCE: 111
ctagaggatc cccgggtac                                                     19

<210> SEQ ID NO 112
<211> LENGTH: 27
<212> TYPE: DNA
<213> ORGANISM: Artificial Sequence
<220> FEATURE:
<223> OTHER INFORMATION: Sequencing of DSB repair junction in MCF7 with
      L67+ABT888

<400> SEQUENCE: 112
atcatggtca tagctgtttc ctgtgtg                                            27

<210> SEQ ID NO 113
<211> LENGTH: 19
<212> TYPE: DNA
```

<213> ORGANISM: Artificial Sequence
<220> FEATURE:
<223> OTHER INFORMATION: Sequencing of DSB repair junction in MCF7 with
      L67+ABT888

<400> SEQUENCE: 113
ctagaggatc cccgggtac                                                    19

<210> SEQ ID NO 114
<211> LENGTH: 21
<212> TYPE: DNA
<213> ORGANISM: Artificial Sequence
<220> FEATURE:
<223> OTHER INFORMATION: Sequencing of DSB repair junction in MCF7 with
      L67+ABT888

<400> SEQUENCE: 114
gtcatagctg tttcctgtgt g                                                 21

<210> SEQ ID NO 115
<211> LENGTH: 17
<212> TYPE: DNA
<213> ORGANISM: Artificial Sequence
<220> FEATURE:
<223> OTHER INFORMATION: Sequencing of DSB repair junction in MCF7 with
      L67+ABT888

<400> SEQUENCE: 115
ctagaggatc cccgggt                                                      17

<210> SEQ ID NO 116
<211> LENGTH: 19
<212> TYPE: DNA
<213> ORGANISM: Artificial Sequence
<220> FEATURE:
<223> OTHER INFORMATION: Sequencing of DSB repair junction in MCF7 with
      L67+ABT888

<400> SEQUENCE: 116
catagctgtt tcctgtgtg                                                    19

<210> SEQ ID NO 117
<211> LENGTH: 15
<212> TYPE: DNA
<213> ORGANISM: Artificial Sequence
<220> FEATURE:
<223> OTHER INFORMATION: Sequencing of DSB repair junction in MCF7 with
      L67+ABT888

<400> SEQUENCE: 117
gcatgcctgc aggtc                                                        15

<210> SEQ ID NO 118
<211> LENGTH: 6
<212> TYPE: DNA
<213> ORGANISM: Artificial Sequence
<220> FEATURE:
<223> OTHER INFORMATION: Sequencing of DSB repair junction in MCF7 with
      L67+ABT888

<400> SEQUENCE: 118 tgtgtg                                                                   6

<210> SEQ ID NO 119
<211> LENGTH: 3
<212> TYPE: DNA
<213> ORGANISM: Artificial Sequence

```
<220> FEATURE:
<223> OTHER INFORMATION: Sequencing of DSB repair junction in MCF7 with
      L67+ABT888

<400> SEQUENCE: 119 cta                                                                        3

<210> SEQ ID NO 120
<211> LENGTH: 15
<212> TYPE: DNA
<213> ORGANISM: Artificial Sequence
<220> FEATURE:
<223> OTHER INFORMATION: Sequencing of DSB repair junction in MCF7 with
      L67+ABT888

<400> SEQUENCE: 120
tgttatccgc tcaca                                                          15

<210> SEQ ID NO 121
<211> LENGTH: 15
<212> TYPE: DNA
<213> ORGANISM: Artificial Sequence
<220> FEATURE:
<223> OTHER INFORMATION: Sequencing of DSB repair junction in MCF7 with
      L67+ABT888

<400> SEQUENCE: 121
ccaacgttgc atgcc                                                          15

<210> SEQ ID NO 122
<211> LENGTH: 2
<212> TYPE: DNA
<213> ORGANISM: Artificial Sequence
<220> FEATURE:
<223> OTHER INFORMATION: Sequencing of DSB repair junction in MCF7 with
      L67+ABT888

<400> SEQUENCE: 122 tg                                                                         2

<210> SEQ ID NO 123
<211> LENGTH: 3
<212> TYPE: DNA
<213> ORGANISM: Artificial Sequence
<220> FEATURE:
<223> OTHER INFORMATION: Sequencing of DSB repair junction in MCF7 with
      L67+ABT888

<400> SEQUENCE: 123 cta                                                                        3

<210> SEQ ID NO 124
<211> LENGTH: 15
<212> TYPE: DNA
<213> ORGANISM: Artificial Sequence
<220> FEATURE:
<223> OTHER INFORMATION: Sequencing of DSB repair junction in MCF7 with
      L67+ABT888

<400> SEQUENCE: 124
acaattccac acaac                                                          15

<210> SEQ ID NO 125
<211> LENGTH: 15
<212> TYPE: DNA
<213> ORGANISM: Artificial Sequence
<220> FEATURE:
```

```
<223> OTHER INFORMATION: Sequencing of DSB repair junction in MCF7 with
      L67+ABT888

<400> SEQUENCE: 125
acgccagggt tttcc                                                          15

<210> SEQ ID NO 126
<211> LENGTH: 15
<212> TYPE: DNA
<213> ORGANISM: Artificial Sequence
<220> FEATURE:
<223> OTHER INFORMATION: Sequencing of DSB repair junction in MCF7 with
      L67+ABT888

<400> SEQUENCE: 126
ggaagcataa agtgt                                                          15

<210> SEQ ID NO 127
<211> LENGTH: 31
<212> TYPE: DNA
<213> ORGANISM: Artificial Sequence
<220> FEATURE:
<223> OTHER INFORMATION: Sequencing of DSB repair junction in TAM1 with
      CTRL

<400> SEQUENCE: 127
ctagaggatc cccgggtacc gagctcgaat t                                        31

<210> SEQ ID NO 128
<211> LENGTH: 30
<212> TYPE: DNA
<213> ORGANISM: Artificial Sequence
<220> FEATURE:
<223> OTHER INFORMATION: Sequencing of DSB repair junction in TAM1 with
      CTRL

<400> SEQUENCE: 128
gtaatcatgg tcatagctgt ttcctgtgtg                                          30

<210> SEQ ID NO 129
<211> LENGTH: 26
<212> TYPE: DNA
<213> ORGANISM: Artificial Sequence
<220> FEATURE:
<223> OTHER INFORMATION: Sequencing of DSB repair junction in TAM1 with
      CTRL

<400> SEQUENCE: 129
gatctcctag gggcccatgg ctcgag                                              26

<210> SEQ ID NO 130
<211> LENGTH: 35
<212> TYPE: DNA
<213> ORGANISM: Artificial Sequence
<220> FEATURE:
<223> OTHER INFORMATION: Sequencing of DSB repair junction in TAM1 with
      CTRL

<400> SEQUENCE: 130
cttaacatta gtaccagtat cgacaaagga cacac                                    35

<210> SEQ ID NO 131
<211> LENGTH: 31
<212> TYPE: DNA
<213> ORGANISM: Artificial Sequence
<220> FEATURE:
<223> OTHER INFORMATION: Sequencing of DSB repair junction in TAM1 with
```

CTRL

<400> SEQUENCE: 131
ctagaggatc cccgggtacc gagctcgaat t                                    31

<210> SEQ ID NO 132
<211> LENGTH: 30
<212> TYPE: DNA
<213> ORGANISM: Artificial Sequence
<220> FEATURE:
<223> OTHER INFORMATION: Sequencing of DSB repair junction in TAM1 with
      CTRL

<400> SEQUENCE: 132
gtaatcatgg tcatagctgt ttcctgtgtg                                      30

<210> SEQ ID NO 133
<211> LENGTH: 27
<212> TYPE: DNA
<213> ORGANISM: Artificial Sequence
<220> FEATURE:
<223> OTHER INFORMATION: Sequencing of DSB repair junction in TAM1 with
      CTRL

<400> SEQUENCE: 133
ctagaggatc cccgggtacc gagctcg                                         27

<210> SEQ ID NO 134
<211> LENGTH: 30
<212> TYPE: DNA
<213> ORGANISM: Artificial Sequence
<220> FEATURE:
<223> OTHER INFORMATION: Sequencing of DSB repair junction in TAM1 with
      CTRL

<400> SEQUENCE: 134
gtaatcatgg tcatagctgt ttcctgtgtg                                      30

<210> SEQ ID NO 135
<211> LENGTH: 19
<212> TYPE: DNA
<213> ORGANISM: Artificial Sequence
<220> FEATURE:
<223> OTHER INFORMATION: Sequencing of DSB repair junction in TAM1 with
      CTRL

<400> SEQUENCE: 135
ctagaggatc cccgggtac                                                  19

<210> SEQ ID NO 136
<211> LENGTH: 28
<212> TYPE: DNA
<213> ORGANISM: Artificial Sequence
<220> FEATURE:
<223> OTHER INFORMATION: Sequencing of DSB repair junction in TAM1 with
      CTRL

<400> SEQUENCE: 136
aatcatggtc atagctgttt cctgtgtg                                        28

<210> SEQ ID NO 137
<211> LENGTH: 19
<212> TYPE: DNA
<213> ORGANISM: Artificial Sequence
<220> FEATURE:
<223> OTHER INFORMATION: Sequencing of DSB repair junction in TAM1 with
      CTRL

<400> SEQUENCE: 137
ctagaggatc cccgggtac                                                    19

<210> SEQ ID NO 138
<211> LENGTH: 27
<212> TYPE: DNA
<213> ORGANISM: Artificial Sequence
<220> FEATURE:
<223> OTHER INFORMATION: Sequencing of DSB repair junction in TAM1 with
      CTRL

<400> SEQUENCE: 138
atcatggtca tagctgtttc ctgtgtg                                            27

<210> SEQ ID NO 139
<211> LENGTH: 16
<212> TYPE: DNA
<213> ORGANISM: Artificial Sequence
<220> FEATURE:
<223> OTHER INFORMATION: Sequencing of DSB repair junction in TAM1 with
      CTRL

<400> SEQUENCE: 139
ctagaggatc cccggg                                                       16

<210> SEQ ID NO 140
<211> LENGTH: 19
<212> TYPE: DNA
<213> ORGANISM: Artificial Sequence
<220> FEATURE:
<223> OTHER INFORMATION: Sequencing of DSB repair junction in TAM1 with
      CTRL

<400> SEQUENCE: 140
catagctgtt tcctgtgtg                                                    19

<210> SEQ ID NO 141
<211> LENGTH: 16
<212> TYPE: DNA
<213> ORGANISM: Artificial Sequence
<220> FEATURE:
<223> OTHER INFORMATION: Sequencing of DSB repair junction in TAM1 with
      CTRL

<400> SEQUENCE: 141
ctagaggatc cccggg                                                       16

<210> SEQ ID NO 142
<211> LENGTH: 17
<212> TYPE: DNA
<213> ORGANISM: Artificial Sequence
<220> FEATURE:
<223> OTHER INFORMATION: Sequencing of DSB repair junction in TAM1 with
      CTRL

<400> SEQUENCE: 142
tagctgtttc ctgtgtg                                                      17

<210> SEQ ID NO 143
<211> LENGTH: 15
<212> TYPE: DNA
<213> ORGANISM: Artificial Sequence
<220> FEATURE:
<223> OTHER INFORMATION: Sequencing of DSB repair junction in TAM1 with
      CTRL

```
<400> SEQUENCE: 143
gcatgcctgc aggtc                                                        15

<210> SEQ ID NO 144
<211> LENGTH: 7
<212> TYPE: DNA
<213> ORGANISM: Artificial Sequence
<220> FEATURE:
<223> OTHER INFORMATION: Sequencing of DSB repair junction in TAM1 with
      CTRL

<400> SEQUENCE: 144 ctgtgtg                                                                  7

<210> SEQ ID NO 145
<211> LENGTH: 15
<212> TYPE: DNA
<213> ORGANISM: Artificial Sequence
<220> FEATURE:
<223> OTHER INFORMATION: Sequencing of DSB repair junction in TAM1 with
      CTRL

<400> SEQUENCE: 145
acgttgcatg cctgc                                                        15

<210> SEQ ID NO 146
<211> LENGTH: 1
<212> TYPE: DNA
<213> ORGANISM: Artificial Sequence
<220> FEATURE:
<223> OTHER INFORMATION: Sequencing of DSB repair junction in TAM1 with
      CTRL

<400> SEQUENCE: 146 g                                                                        1

<210> SEQ ID NO 147
<211> LENGTH: 15
<212> TYPE: DNA
<213> ORGANISM: Artificial Sequence
<220> FEATURE:
<223> OTHER INFORMATION: Sequencing of DSB repair junction in TAM1 with
      CTRL

<400> SEQUENCE: 147
ccaacgttgc atgcc                                                        15

<210> SEQ ID NO 148
<211> LENGTH: 2
<212> TYPE: DNA
<213> ORGANISM: Artificial Sequence
<220> FEATURE:
<223> OTHER INFORMATION: Sequencing of DSB repair junction in TAM1 with
      CTRL

<400> SEQUENCE: 148 tg                                                                       2

<210> SEQ ID NO 149
<211> LENGTH: 3
<212> TYPE: DNA
<213> ORGANISM: Artificial Sequence
<220> FEATURE:
<223> OTHER INFORMATION: Sequencing of DSB repair junction in TAM1 with
      CTRL

<400> SEQUENCE: 149
```

-continued cta                                                                3

<210> SEQ ID NO 150
<211> LENGTH: 15
<212> TYPE: DNA
<213> ORGANISM: Artificial Sequence
<220> FEATURE:
<223> OTHER INFORMATION: Sequencing of DSB repair junction in TAM1 with
      CTRL

<400> SEQUENCE: 150
acaattccac acaac                                                   15

<210> SEQ ID NO 151
<211> LENGTH: 3
<212> TYPE: DNA
<213> ORGANISM: Artificial Sequence
<220> FEATURE:
<223> OTHER INFORMATION: Sequencing of DSB repair junction in TAM1 with
      CTRL

<400> SEQUENCE: 151 cta                                                                3

<210> SEQ ID NO 152
<211> LENGTH: 15
<212> TYPE: DNA
<213> ORGANISM: Artificial Sequence
<220> FEATURE:
<223> OTHER INFORMATION: Sequencing of DSB repair junction in TAM1 with
      CTRL

<400> SEQUENCE: 152
catacgagcc ggaag                                                   15

<210> SEQ ID NO 153
<211> LENGTH: 3
<212> TYPE: DNA
<213> ORGANISM: Artificial Sequence
<220> FEATURE:
<223> OTHER INFORMATION: Sequencing of DSB repair junction in TAM1 with
      CTRL

<400> SEQUENCE: 153 cta                                                                3

<210> SEQ ID NO 154
<211> LENGTH: 15
<212> TYPE: DNA
<213> ORGANISM: Artificial Sequence
<220> FEATURE:
<223> OTHER INFORMATION: Sequencing of DSB repair junction in TAM1 with
      CTRL

<400> SEQUENCE: 154
aaagcctggg gtgcc                                                   15

<210> SEQ ID NO 155
<211> LENGTH: 3
<212> TYPE: DNA
<213> ORGANISM: Artificial Sequence
<220> FEATURE:
<223> OTHER INFORMATION: Sequencing of DSB repair junction in TAM1 with
      CTRL

<400> SEQUENCE: 155

```
cta                                                                    3
```

<210> SEQ ID NO 156
<211> LENGTH: 15
<212> TYPE: DNA
<213> ORGANISM: Artificial Sequence
<220> FEATURE:
<223> OTHER INFORMATION: Sequencing of DSB repair junction in TAM1 with
      CTRL

<400> SEQUENCE: 156

```
ggggtgccta atgag                                                      15
```

<210> SEQ ID NO 157
<211> LENGTH: 3
<212> TYPE: DNA
<213> ORGANISM: Artificial Sequence
<220> FEATURE:
<223> OTHER INFORMATION: Sequencing of DSB repair junction in TAM1 with
      CTRL

<400> SEQUENCE: 157

```
cta                                                                    3
```

<210> SEQ ID NO 158
<211> LENGTH: 15
<212> TYPE: DNA
<213> ORGANISM: Artificial Sequence
<220> FEATURE:
<223> OTHER INFORMATION: Sequencing of DSB repair junction in TAM1 with
      CTRL

<400> SEQUENCE: 158

```
gtgcctaatg agtga                                                      15
```

<210> SEQ ID NO 159
<211> LENGTH: 15
<212> TYPE: DNA
<213> ORGANISM: Artificial Sequence
<220> FEATURE:
<223> OTHER INFORMATION: Sequencing of DSB repair junction in TAM1 with
      CTRL

<400> SEQUENCE: 159

```
catgcctgca ggtcg                                                      15
```

<210> SEQ ID NO 160
<211> LENGTH: 15
<212> TYPE: DNA
<213> ORGANISM: Artificial Sequence
<220> FEATURE:
<223> OTHER INFORMATION: Sequencing of DSB repair junction in TAM1 with
      CTRL

<400> SEQUENCE: 160

```
taattgcgtt gcgct                                                      15
```

<210> SEQ ID NO 161
<211> LENGTH: 15
<212> TYPE: DNA
<213> ORGANISM: Artificial Sequence
<220> FEATURE:
<223> OTHER INFORMATION: Sequencing of DSB repair junction in TAM1 with
      CTRL

<400> SEQUENCE: 161

```
cgattaagtt gggta                                                      15
```

<210> SEQ ID NO 162
<211> LENGTH: 15
<212> TYPE: DNA
<213> ORGANISM: Artificial Sequence
<220> FEATURE:
<223> OTHER INFORMATION: Sequencing of DSB repair junction in TAM1 with
      CTRL

<400> SEQUENCE: 162
aagcctgggg tgcct                                                    15

<210> SEQ ID NO 163
<211> LENGTH: 14
<212> TYPE: DNA
<213> ORGANISM: Artificial Sequence
<220> FEATURE:
<223> OTHER INFORMATION: Sequencing of DSB repair junction in TAM1 with
      CTRL

<400> SEQUENCE: 163
taccgcatca ggcg                                                     14

<210> SEQ ID NO 164
<211> LENGTH: 15
<212> TYPE: DNA
<213> ORGANISM: Artificial Sequence
<220> FEATURE:
<223> OTHER INFORMATION: Sequencing of DSB repair junction in TAM1 with
      CTRL

<400> SEQUENCE: 164
gcataaagtg taaag                                                    15

<210> SEQ ID NO 165
<211> LENGTH: 14
<212> TYPE: DNA
<213> ORGANISM: Artificial Sequence
<220> FEATURE:
<223> OTHER INFORMATION: Sequencing of DSB repair junction in TAM1 with
      CTRL

<400> SEQUENCE: 165
taccgcatca ggcg                                                     14

<210> SEQ ID NO 166
<211> LENGTH: 15
<212> TYPE: DNA
<213> ORGANISM: Artificial Sequence
<220> FEATURE:
<223> OTHER INFORMATION: Sequencing of DSB repair junction in TAM1 with
      CTRL

<400> SEQUENCE: 166
ataaagtgta aagcc                                                    15

<210> SEQ ID NO 167
<211> LENGTH: 15
<212> TYPE: DNA
<213> ORGANISM: Artificial Sequence
<220> FEATURE:
<223> OTHER INFORMATION: Sequencing of DSB repair junction in TAM1 with
      CTRL

<400> SEQUENCE: 167
atgtgctgca aggcg                                                    15

```
<210> SEQ ID NO 168
<211> LENGTH: 15
<212> TYPE: DNA
<213> ORGANISM: Artificial Sequence
<220> FEATURE:
<223> OTHER INFORMATION: Sequencing of DSB repair junction in TAM1 with
      CTRL

<400> SEQUENCE: 168
ttgcgtattg ggcgc                                                          15

<210> SEQ ID NO 169
<211> LENGTH: 15
<212> TYPE: DNA
<213> ORGANISM: Artificial Sequence
<220> FEATURE:
<223> OTHER INFORMATION: Sequencing of DSB repair junction in TAM1 with
      CTRL

<400> SEQUENCE: 169
atgtgctgca aggcg                                                          15

<210> SEQ ID NO 170
<211> LENGTH: 15
<212> TYPE: DNA
<213> ORGANISM: Artificial Sequence
<220> FEATURE:
<223> OTHER INFORMATION: Sequencing of DSB repair junction in TAM1 with
      CTRL

<400> SEQUENCE: 170
gcgtattggg cgctc                                                          15

<210> SEQ ID NO 171
<211> LENGTH: 15
<212> TYPE: DNA
<213> ORGANISM: Artificial Sequence
<220> FEATURE:
<223> OTHER INFORMATION: Sequencing of DSB repair junction in TAM1 with
      CTRL

<400> SEQUENCE: 171
cattcaggct gcgca                                                          15

<210> SEQ ID NO 172
<211> LENGTH: 15
<212> TYPE: DNA
<213> ORGANISM: Artificial Sequence
<220> FEATURE:
<223> OTHER INFORMATION: Sequencing of DSB repair junction in TAM1 with
      CTRL

<400> SEQUENCE: 172
gggcgctctt ccgct                                                          15

<210> SEQ ID NO 173
<211> LENGTH: 15
<212> TYPE: DNA
<213> ORGANISM: Artificial Sequence
<220> FEATURE:
<223> OTHER INFORMATION: Sequencing of DSB repair junction in TAM1 with
      CTRL

<400> SEQUENCE: 173
gcatcaggcg ccatt                                                          15
```

<210> SEQ ID NO 174
<211> LENGTH: 15
<212> TYPE: DNA
<213> ORGANISM: Artificial Sequence
<220> FEATURE:
<223> OTHER INFORMATION: Sequencing of DSB repair junction in TAM1 with
      CTRL

<400> SEQUENCE: 174
cggctgcggc gagcg                                                          15

<210> SEQ ID NO 175
<211> LENGTH: 31
<212> TYPE: DNA
<213> ORGANISM: Artificial Sequence
<220> FEATURE:
<223> OTHER INFORMATION: Sequencing of DSB repair junction in TAM1 with
      L67+ABT888

<400> SEQUENCE: 175
ctagaggatc cccgggtacc gagctcgaat t                                        31

<210> SEQ ID NO 176
<211> LENGTH: 30
<212> TYPE: DNA
<213> ORGANISM: Artificial Sequence
<220> FEATURE:
<223> OTHER INFORMATION: Sequencing of DSB repair junction in TAM1 with
      L67+ABT888

<400> SEQUENCE: 176
gtaatcatgg tcatagctgt ttcctgtgtg                                          30

<210> SEQ ID NO 177
<211> LENGTH: 26
<212> TYPE: DNA
<213> ORGANISM: Artificial Sequence
<220> FEATURE:
<223> OTHER INFORMATION: Sequencing of DSB repair junction in TAM1 with
      L67+ABT888

<400> SEQUENCE: 177
gatctcctag gggcccatgg ctcgag                                              26

<210> SEQ ID NO 178
<211> LENGTH: 35
<212> TYPE: DNA
<213> ORGANISM: Artificial Sequence
<220> FEATURE:
<223> OTHER INFORMATION: Sequencing of DSB repair junction in TAM1 with
      L67+ABT888

<400> SEQUENCE: 178
cttaacatta gtaccagtat cgacaaagga cacac                                    35

<210> SEQ ID NO 179
<211> LENGTH: 31
<212> TYPE: DNA
<213> ORGANISM: Artificial Sequence
<220> FEATURE:
<223> OTHER INFORMATION: Sequencing of DSB repair junction in TAM1 with
      L67+ABT888

<400> SEQUENCE: 179
ctagaggatc cccgggtacc gagctcgaat t                                        31

<210> SEQ ID NO 180

<211> LENGTH: 30
<212> TYPE: DNA
<213> ORGANISM: Artificial Sequence
<220> FEATURE:
<223> OTHER INFORMATION: Sequencing of DSB repair junction in TAM1 with
      L67+ABT888

<400> SEQUENCE: 180
gtaatcatgg tcatagctgt ttcctgtgtg                                    30

<210> SEQ ID NO 181
<211> LENGTH: 27
<212> TYPE: DNA
<213> ORGANISM: Artificial Sequence
<220> FEATURE:
<223> OTHER INFORMATION: Sequencing of DSB repair junction in TAM1 with
      L67+ABT888

<400> SEQUENCE: 181
ctagaggatc cccgggtacc gagctcg                                       27

<210> SEQ ID NO 182
<211> LENGTH: 30
<212> TYPE: DNA
<213> ORGANISM: Artificial Sequence
<220> FEATURE:
<223> OTHER INFORMATION: Sequencing of DSB repair junction in TAM1 with
      L67+ABT888

<400> SEQUENCE: 182
gtaatcatgg tcatagctgt ttcctgtgtg                                    30

<210> SEQ ID NO 183
<211> LENGTH: 26
<212> TYPE: DNA
<213> ORGANISM: Artificial Sequence
<220> FEATURE:
<223> OTHER INFORMATION: Sequencing of DSB repair junction in TAM1 with
      L67+ABT888

<400> SEQUENCE: 183
ctagaggatc cccgggtacc gagctc                                        26

<210> SEQ ID NO 184
<211> LENGTH: 29
<212> TYPE: DNA
<213> ORGANISM: Artificial Sequence
<220> FEATURE:
<223> OTHER INFORMATION: Sequencing of DSB repair junction in TAM1 with
      L67+ABT888

<400> SEQUENCE: 184
taatcatggt catagctgtt tcctgtgtg                                     29

<210> SEQ ID NO 185
<211> LENGTH: 19
<212> TYPE: DNA
<213> ORGANISM: Artificial Sequence
<220> FEATURE:
<223> OTHER INFORMATION: Sequencing of DSB repair junction in TAM1 with
      L67+ABT888

<400> SEQUENCE: 185
ctagaggatc cccgggtac                                                19

<210> SEQ ID NO 186
<211> LENGTH: 28

<212> TYPE: DNA
<213> ORGANISM: Artificial Sequence
<220> FEATURE:
<223> OTHER INFORMATION: Sequencing of DSB repair junction in TAM1 with
      L67+ABT888

<400> SEQUENCE: 186
aatcatggtc atagctgttt cctgtgtg                                          28

<210> SEQ ID NO 187
<211> LENGTH: 19
<212> TYPE: DNA
<213> ORGANISM: Artificial Sequence
<220> FEATURE:
<223> OTHER INFORMATION: Sequencing of DSB repair junction in TAM1 with
      L67+ABT888

<400> SEQUENCE: 187
ctagaggatc cccgggtac                                                    19

<210> SEQ ID NO 188
<211> LENGTH: 27
<212> TYPE: DNA
<213> ORGANISM: Artificial Sequence
<220> FEATURE:
<223> OTHER INFORMATION: Sequencing of DSB repair junction in TAM1 with
      L67+ABT888

<400> SEQUENCE: 188
atcatggtca tagctgtttc ctgtgtg                                           27

<210> SEQ ID NO 189
<211> LENGTH: 19
<212> TYPE: DNA
<213> ORGANISM: Artificial Sequence
<220> FEATURE:
<223> OTHER INFORMATION: Sequencing of DSB repair junction in TAM1 with
      L67+ABT888

<400> SEQUENCE: 189
ctagaggatc cccgggtac                                                    19

<210> SEQ ID NO 190
<211> LENGTH: 21
<212> TYPE: DNA
<213> ORGANISM: Artificial Sequence
<220> FEATURE:
<223> OTHER INFORMATION: Sequencing of DSB repair junction in TAM1 with
      L67+ABT888

<400> SEQUENCE: 190
gtcatagctg tttcctgtgt g                                                 21

<210> SEQ ID NO 191
<211> LENGTH: 16
<212> TYPE: DNA
<213> ORGANISM: Artificial Sequence
<220> FEATURE:
<223> OTHER INFORMATION: Sequencing of DSB repair junction in TAM1 with
      L67+ABT888

<400> SEQUENCE: 191
ctagaggatc cccggg                                                       16

<210> SEQ ID NO 192
<211> LENGTH: 17
<212> TYPE: DNA

<213> ORGANISM: Artificial Sequence
<220> FEATURE:
<223> OTHER INFORMATION: Sequencing of DSB repair junction in TAM1 with
      L67+ABT888

<400> SEQUENCE: 192
tagctgtttc ctgtgtg                                                  17

<210> SEQ ID NO 193
<211> LENGTH: 15
<212> TYPE: DNA
<213> ORGANISM: Artificial Sequence
<220> FEATURE:
<223> OTHER INFORMATION: Sequencing of DSB repair junction in TAM1 with
      L67+ABT888

<400> SEQUENCE: 193
ctagaggatc cccgg                                                    15

<210> SEQ ID NO 194
<211> LENGTH: 17
<212> TYPE: DNA
<213> ORGANISM: Artificial Sequence
<220> FEATURE:
<223> OTHER INFORMATION: Sequencing of DSB repair junction in TAM1 with
      L67+ABT888

<400> SEQUENCE: 194
tagctgtttc ctgtgtg                                                  17

<210> SEQ ID NO 195
<211> LENGTH: 3
<212> TYPE: DNA
<213> ORGANISM: Artificial Sequence
<220> FEATURE:
<223> OTHER INFORMATION: Sequencing of DSB repair junction in TAM1 with
      L67+ABT888

<400> SEQUENCE: 195 cta                                                                  3

<210> SEQ ID NO 196
<211> LENGTH: 15
<212> TYPE: DNA
<213> ORGANISM: Artificial Sequence
<220> FEATURE:
<223> OTHER INFORMATION: Sequencing of DSB repair junction in TAM1 with
      L67+ABT888

<400> SEQUENCE: 196
tgttatccgc tcaca                                                    15

<210> SEQ ID NO 197
<211> LENGTH: 15
<212> TYPE: DNA
<213> ORGANISM: Artificial Sequence
<220> FEATURE:
<223> OTHER INFORMATION: Sequencing of DSB repair junction in TAM1 with
      L67+ABT888

<400> SEQUENCE: 197
ccaacgttgc atgcc                                                    15

<210> SEQ ID NO 198
<211> LENGTH: 2
<212> TYPE: DNA
<213> ORGANISM: Artificial Sequence

```
<220> FEATURE:
<223> OTHER INFORMATION: Sequencing of DSB repair junction in TAM1 with
      L67+ABT888

<400> SEQUENCE: 198 tg                                                                          2

<210> SEQ ID NO 199
<211> LENGTH: 15
<212> TYPE: DNA
<213> ORGANISM: Artificial Sequence
<220> FEATURE:
<223> OTHER INFORMATION: Sequencing of DSB repair junction in TAM1 with
      L67+ABT888

<400> SEQUENCE: 199
catgcctgca ggtcg                                                           15

<210> SEQ ID NO 200
<211> LENGTH: 15
<212> TYPE: DNA
<213> ORGANISM: Artificial Sequence
<220> FEATURE:
<223> OTHER INFORMATION: Sequencing of DSB repair junction in TAM1 with
      L67+ABT888

<400> SEQUENCE: 200
taattgcgtt gcgct                                                           15

<210> SEQ ID NO 201
<211> LENGTH: 15
<212> TYPE: DNA
<213> ORGANISM: Artificial Sequence
<220> FEATURE:
<223> OTHER INFORMATION: Sequencing of DSB repair junction in TAM1 with
      L67+ABT888

<400> SEQUENCE: 201
agttgggtaa cgcca                                                           15

<210> SEQ ID NO 202
<211> LENGTH: 15
<212> TYPE: DNA
<213> ORGANISM: Artificial Sequence
<220> FEATURE:
<223> OTHER INFORMATION: Sequencing of DSB repair junction in TAM1 with
      L67+ABT888

<400> SEQUENCE: 202
tgccagctgc attaa                                                           15
```

TARGETING ABNORMAL DNA REPAIR IN THERAPY-RESISTANT BREAST AND PANCREATIC CANCERS

CLAIM OF PRIORITY

This application claims the benefit of priority of U.S. provisional application Ser. No. 61/619,379, filed Apr. 2, 2012 entitled "Targeting Abnormal DNA Repair in Therapy-Resistant Breast Cancers, the entire contents of said application being incorporated by reference in its entirety herein.

STATEMENT REGARDING FEDERAL FUNDING

This invention was made with the support of National Institutes of Health (NIH) Grant Numbers GM057479, GM047251, ES012512, and CA092584. The U.S. government has certain rights in this invention.

BACKGROUND OF THE INVENTION

The majority of breast cancers occur in postmenopausal women with 75% of these tumors being estrogen dependent as defined by estrogen receptor (ER) a positivity (1). Tamoxifen, an anti-estrogen, has been the mainstay of treatment for hormone-dependent breast cancers. However, recent clinical trials have shown that inhibitors of aromatase, which catalyzes the rate-limiting step of estrogen biosynthesis, may be more effective than tamoxifen in treating hormone-dependent breast cancers in postmenopausal women (2). Unfortunately, resistance to both these endocrine therapies is inevitable in metastatic breast cancer (3). Thus, there is a compelling need to develop more effective therapies for breast cancer patients with acquired anti-estrogen resistance in addition to those with intrinsic resistance to anti-estrogen and anti-HER2 therapies.

Genomic instability, including chromosomal abnormalities, is a characteristic of both hereditary and sporadic breast cancers (4). The tumors in inherited breast cancer that result from loss of either BRCA1 or BRCA2 function have a defect in the recombinational repair of replication-associated double-strand break (DSB) (5). This specific DNA repair defect in BRCA tumors not only underlies the numerous chromosomal rearrangements in these cells but also results in their hypersensitivity to inhibitors of poly (ADP-ribose) polymerases (PARP) that generate replication-associated DSBs by inhibiting the repair of DNA single-strand breaks (SSB; refs. 4, 6). On the basis of these preclinical studies, potent and specific inhibitors of PARP were developed and are currently being evaluated in clinical trials as therapeutic agents for inherited forms of breast and ovarian cancer (7, 8).

The promising initial results with PARP inhibitors have stimulated interest in DNA repair proteins as therapeutics targets and the characterization of DNA repair defects in sporadic cancers. Recent studies have begun to characterize an alternative (ALT) nonhomologous end joining (NHEJ) pathway that repairs DSBs and is much more error prone than the major DNA-PK-dependent NHEJ pathway (9). Although ALT NHEJ is a relatively minor pathway in normal cells, there is emerging evidence that this pathway is upregulated, whereas the DNA-PK-dependent pathway is downregulated in a significant fraction of cancers (10-12). While genomic instability generated by ALT NHEJ may drive disease progression, ALT NHEJ appears to function as a cancer cell-specific therapeutic target because cells with increased ALT NHEJ are more dependent upon this pathway for survival and are more sensitive to inhibitors that target the ALT NHEJ pathway.

A significant fraction of cell lines established from leukemias and solid tumors have elevated levels of ALT NHEJ proteins and ALT NHEJ activity. These include cell lines from chronic and acute myeloid leukemias and from breast, head and neck, lung and colon cancers, and in clinical samples from patients with chronic myeloid leukemia and breast cancer. Notably, ALT NHEJ activity is elevated in forms of breast cancer and leukemia that are resistant to frontline therapies and these cells are hypersensitive to combination of PARP and DNA ligase inhibitors. Together these studies suggest that a significant fraction of patients will be candidates for treatment with therapies that target ALT NHEJ. This will include patients with disease that is resistant to effective frontline therapies, such as anti-estrogens in breast cancer and patients with disease for which there is no effective therapy, such as pancreatic adenocarcinoma and small cell lung cancer. In the absence of a targeted therapy, patients with these diseases are often treated with combinations of cytotoxic chemotherapeutics that have severe side-effects. For example, (Lowery, et al., "Genomics and pharmacogenomics of pancreatic adenocarcinoma", *Pharmacogenomics,* 2012 February; 12(1):1-9,) the combination of several cytotoxic agents; infusional 5-FU, irinotecan and oxaliplatin, known as FOLFIRINOX, has improved survival in patients with an excellent functional status and stage IV disease by 4.3 months compared with gemcitabine alone but did result in a significant increase in toxicities, in particular gastrointestinal and hematologic. Cancers such as pancreatic cancer and small cell lung cancer without a targeted and/or effective therapy were the subject of the Recalcitrant Cancer Act that was recently passed by Congress. Given the therapeutic and toxicity limitations of existing treatments, there is a need for therapies that are effective in treating patients who suffer from pancreatic cancer (including, but not limited to, pancreatic adenocarcinoma, islet cell carcinoma, and neuroendocrine tumors) and other cancers for which there is no targeted and/or effective therapy.

SUMMARY OF THE INVENTION

We have examined the ALT NHEJ pathway in breast and pancreatic cancers and have discovered novel therapies, diagnostic methods, nucleic acid arrays, devices and kits that implicate that pathway.

Notably, the steady-state levels of PARP1 and DNA ligase IIIα, both of which participate in ALT NHEJ (11, 13-15), are significantly increased in breast cancer cell lines with acquired resistance to anti-estrogen therapies and in ER/PR− breast cancer cell lines. These cell lines also have reduced steady-state levels of DNA ligase IV, a component of the DNA-PK-dependent pathway. Notably, cells with this DNA repair abnormality were hypersensitive to a PARP inhibitor in combination with an inhibitor of DNA ligase III, providing evidence that the ALT NHEJ pathway is a novel therapeutic target in breast cancers that have either failed or are intrinsically resistant to anti-estrogen therapies. Furthermore, because similar changes in expression of DSB repair proteins were also observed in biopsies from ER/PR-tumors, our studies show that altered expression levels of NHEJ proteins serve as biomarkers to identify breast cancer patients whose disease is likely to respond to DNA repair inhibitors that target ALT NHEJ.

As explained in detail hereinafter, we have applied our findings regarding the ALT NHEJ pathway in breast and pancreatic cancers to identify novel therapeutic and diagnostic methods, systems, kits and devices that enable the treatment and diagnosis e.g. of a subject who suffers from an anti-estrogen-resistant breast cancer or a subject whose pancreatic adenocarcinoma is non-responsive to chemotherapy and/or radiation.

In one embodiment, the invention provides a method of treating a subject suffering from a breast cancer tumor which is non-responsive or intrinsically resistant to anti-estrogen therapy comprising administering a therapeutically effective amount of an inhibitor of alternative (ALT) non-homologous end joining (NHEJ) factor to the subject. Inhibitors of alternative (ALT) non-homologous end joining (NHEJ) factor include (but are nor limited to) the ALT NHEJ factor inhibitors described in U.S. Patent Application Document No. 20100099683 (Ser. No. 12/576,410), entitled "Compounds that Inhibit Human DNA Ligases and Methods of Treating Cancer".

In preferred embodiments, the inhibitor of ALT NHEJ factors can be a Poly [ADP-Ribose] Polymerase 1 (PARP1) or a DNA ligase IIIα inhibitor. In other preferred embodiments, the subject suffering from a breast cancer tumor which is non-responsive or intrinsically resistant to anti-estrogen therapy is treated with a combination of a PARP1 inhibitor and a DNA ligase IIIα inhibitor. In other embodiments, the subject's breast cancer tumor also under-expresses DNA-PK-dependent NHEJ factors such as Ku70 and DNA Ligase IV. In still other embodiments, the subject's breast cancer tumor is also resistant to anti-HER2 therapies.

In a particularly preferred embodiment, at least one cytotoxic DNA ligase III inhibitor selected from the group consisting of L67, L-67-5 and L67-6 (described in Table 9 of U.S. Patent Application Document No. 20100099683) (see also reference (10) cited herein) and the PARP1 inhibitor ABT888 are co-administered to a subject suffering from a breast cancer tumor which is non-responsive or intrinsically resistant to anti-estrogen therapy.

In another embodiment, the invention provides a method of treating a subject suffering from an anti-estrogen-naive breast cancer tumor whose cells over-express one or more ALT NHEJ factors (e.g. PARP1 and DNA ligase IIIα) comprising co-administering a therapeutically effective amount of PARP1 inhibitor and a DNA ligase IIIα inhibitor to the subject.

In the various embodiments described herein, a therapeutically effective amount of PARP1 inhibitor and/or a DNA ligase IIIα inhibitor can be administered or co-administered to a subject in the form of a pharmaceutical dosage form comprising the therapeutically effective amount of PARP1 inhibitor and a DNA ligase IIIα inhibitor and, optionally, one or more excipients.

In still another embodiment, the invention provides a method of treating a subject suffering from an anti-estrogen-naive breast cancer tumor whose cells over-express one or more ALT NHEJ factors (e.g. PARP1 and DNA ligase IIIα) and under-express one or more DNA-PK-dependent NHEJ factors (e.g. Ku70 and DNA Ligase IV) comprising co-administering a therapeutically effective amount of PARP1 inhibitor and a DNA ligase IIIα inhibitor to the subject.

In still another embodiment, the invention provides a method of treating a subject suffering from an anti-estrogen-naive breast cancer tumor whose cells, based on an evaluation of clinical factors (e.g. mammogram, breast MRI, ultrasound, age, fractures, bone mineral density screening, Chronic Disease Scores, and co-morbidities) are considered likely to over-express one or more ALT NHEJ factors (e.g. PARP1 and DNA ligase IIIα) comprising co-administering a therapeutically effective amount of PARP1 inhibitor and a DNA ligase IIIα inhibitor to the subject.

In still another embodiment, the invention provides a method of treating a subject suffering from an anti-estrogen-naive breast cancer tumor whose cells, based on an evaluation of clinical factors (e.g. mammogram, breast MRI, ultrasound, age, fractures, bone mineral density screening, Chronic Disease Scores, and co-morbidities) are considered likely to over-express one or more ALT NHEJ factors (e.g. PARP1 and DNA ligase IIIα) and to under-express one or more DNA-PK-dependent NHEJ factors (e.g. Ku70 and DNA Ligase IV) comprising co-administering a therapeutically effective amount of PARP1 inhibitor and a DNA ligase IIIα inhibitor to the subject.

In still another embodiment, the invention provides a method of treating a subject suffering from a treatment-naive breast cancer tumor whose cells over-express one or more ALT NHEJ factors (e.g. PARP1 and DNA ligase IIIα) comprising co-administering a therapeutically effective amount of PARP1 inhibitor and a DNA ligase IIIα inhibitor to the subject.

In still another embodiment, the invention provides a method of treating a subject suffering from a treatment-naive breast cancer tumor whose cells over-express one or more ALT NHEJ factors (e.g. PARP1 and DNA ligase IIIα) and under-express one or more DNA-PK-dependent NHEJ factors (e.g. Ku70 and DNA Ligase IV) comprising co-administering a therapeutically effective amount of PARP1 inhibitor and a DNA ligase IIIα inhibitor to the subject.

In still another embodiment, the invention provides a method of treating a subject suffering from a treatment-naive breast cancer tumor whose cells, based on an evaluation of clinical factors (e.g. mammogram, breast MRI, ultrasound, age, fractures, bone mineral density screening, Chronic Disease Scores, and co-morbidities) are considered likely to over-express one or more ALT NHEJ factors (e.g. PARP1 and DNA ligase IIIα) comprising co-administering a therapeutically effective amount of PARP1 inhibitor and a DNA ligase IIIα inhibitor to the subject.

In still another embodiment, the invention provides a method of treating a subject suffering from a treatment-naive breast cancer tumor whose cells, based on an evaluation of clinical factors (e.g. mammogram, breast MRI, ultrasound, age, fractures, bone mineral density screening, Chronic Disease Scores, and co-morbidities) are considered likely to over-express one or more ALT NHEJ factors (e.g. PARP1 and DNA ligase IIIα) and to under-express one or more DNA-PK-dependent NHEJ factors (e.g. Ku70 and DNA Ligase IV) comprising co-administering a therapeutically effective amount of PARP1 inhibitor and a DNA ligase IIIα inhibitor to the subject.

Methods for identifying solid tumors suitable for treatment using inhibitors of alternative (ALT) non-homologous end joining (NHEJ) factors are also provided. Expression levels of ALT NHEJ factors are determined in tumor cells. Cells expressing elevated levels of the ALT NHEJ factors are identified, based on a comparison to normal, non-tumor cells of the same type of tissue, as cells from tumors suitable for treatments as described above. The inhibitors of ALT NHEJ factors can be Poly [ADP-Ribose] Polymerase 1 (PARP1) and DNA ligase IIIα inhibitors. The aforementioned diagnostic method can also comprise determining the expression levels in said cells of DNA protein kinase (PK)-dependent nonhomologous end joining (NHEJ) factors and identifying cells expressing reduced levels of said DNA-PK-dependent NHEJ factors, compared to normal, non-tumor cells of the same type of tissue, in addition to expressing elevated levels of said ALT NHEJ factors, compared to normal, non-tumor cells of the same type of tissue, as cells from tumors suitable for treatment. The DNA-PK-dependent NHEJ factors can be Ku70, Ku80, XRCC4 and DNA Ligase IV.

Elevated levels of an ALT NHEJ factor in anti-estrogen resistant breast cancer or a pancreatic cancer which is non-responsive to chemotherapy and/or radiation can be an increase of between about 5-10%, or about 10-15%, or about 15-20%, or about 20-25%, or about 25-30%, or about 30-35%, or about 35-40%, or about 40-45%, or about 45-50%, or about 50-55%, or about 55-60%, or about 60-65%, or about 65-70%, or about 70-75%, or about 75-80%, or about 80-85%, or about 85-90%, or about 90-95%, or about 95-100%, or about 100-110%, or about 110-120%, or about 120-130%, or about 130-140%, or about 140-150%, or about 150-160%, or about 160-170%, or about 170-180%, or about 180-190%, or about 190-200%, or about 200-210%, or about 210-220%, or about 220-230%, or about 230-240%, or about 240-250%, or about 250-260%, or about 260-270%, or about 270-280%, or about 280-290%, or about 290-300%, or preferably between about 1.5-fold and about 3-fold normal level. In certain embodiments, the elevated level of an ALT NHEJ factor is greater than about 3-fold normal level. In other embodiments, the elevated level of an ALT NHEJ factor is between about 2-fold and about 3-fold normal level. In still other embodiments, the reduced level of a DNA-PK-dependent NHEJ factor is about 50% less than its normal level.

Determination of expression levels can be done by measuring RNA transcript levels, or by histochemical methods using antibodies that bind to the factors, or any other methods known to the art. The tumor cells can be from biopsy of a tumor or can be tissue cultured tumor cells. The normal cells can be from tissues of patients not having solid tumors, or can be cultured normal cells from such tissues.

For example, in one embodiment, the invention provides a method of classifying a subject's breast cancer tumor as being either responsive or non-responsive to anti-estrogen mono or co-therapy, the method comprising:
(a) determining the ALT NHEJ factor expression level (e.g. by measuring RNA transcript levels) in a breast cancer tumor sample obtained from the subject; and
(b) comparing the expression level to a reference expression pattern profile;
wherein a determination that the sample's ALT NHEJ factor expression level exceeds its corresponding expression reference value indicates that the subject's breast cancer tumor is not responsive to anti-estrogen mono or co-therapy.

In another embodiment, the invention provides a method of classifying a subject's breast cancer tumor as being either responsive or non-responsive to anti-estrogen mono or co-therapy, the method comprising:
(a) determining the ALT NHEJ factor expression level and the DNA-PK-dependent NHEJ factor expression level in a breast cancer tumor sample obtained from the subject; and
(b) comparing the ALT NHEJ factor and DNA-PK-dependent NHEJ factor expression levels to a reference expression pattern profile;
wherein a determination that (1) the sample's ALT NHEJ factor expression level exceeds its corresponding expression reference value, and (2) the sample's DNA-PK-dependent NHEJ factor expression level is less than corresponding expression reference value indicates that the subject's breast cancer tumor is not responsive to anti-estrogen mono or co-therapy.

In still another embodiment, the invention provides a method of classifying a subject's breast cancer tumor as being either responsive or non-responsive to anti-estrogen mono or co-therapy, the method comprising:
(a) determining the expression level (e.g. by measuring RNA transcript levels) of DNA-PK-dependent NHEJ proteins Ku70 and DNA ligase IV in a breast cancer tumor sample obtained from the subject; and
(b) comparing the expression level to a reference expression pattern profile; wherein a determination that the sample's expression level of DNA-PK-dependent NHEJ proteins Ku70 and DNA ligase IV is less than its corresponding expression reference value indicates that the subject's breast cancer tumor is not responsive to anti-estrogen mono or co-therapy.

In the diagnostic methods described above, the subject's breast cancer tumor can be a breast cancer tumor which is non-responsive or intrinsically resistant to anti-estrogen therapy. Alternatively, the subject's breast cancer tumor can be a treatment-naive (e.g. anti-estrogen naïve) breast cancer tumor.

In another embodiment the invention provides a nucleic acid array for expression-based classification of a breast cancer tumor as being either responsive or non-responsive to anti-estrogen mono or co-therapy, the array comprising at least 10 and up to about 250 or more probes immobilized on a solid support, each of the probes:
(a) having a length of between about 25 to about 50 or more nucleotides; and
(b) being derived from sequences corresponding to, or complementary to, transcripts or partial transcripts of each member of one or more prognostic gene sets comprised of genes encoding PARP1 or DNA ligase IIIα.

In still another embodiment the invention provides a nucleic acid array for expression-based classification of a breast cancer tumor as being either responsive or non-responsive to anti-estrogen mono or co-therapy, the array comprising at least 20 and up to about 250 or more probes immobilized on a solid support, each of the probes:
(a) having a length of between about 25 to about 50 or more nucleotides; and
(b) being derived from sequences corresponding to, or complementary to, transcripts or partial transcripts of each member of one or more prognostic gene sets comprised of genes encoding PARP1, PARP2, PARP3, DNA ligase IIIα, XRCC1, Ku70, Ku80, XRCC4 and DNA ligase IV.

Genes encoding PARP1 include NCBI Gene 142 and compliments or variants thereof. Genes encoding PARP2 include NCBI gene 10038 and compliments or variants thereof. Genes encoding PARP3 include NCBI gene 10039 and compliments or variants thereof. Genes encoding DNA ligase IIIα include NCBI Gene 3980 and compliments or variants thereof. Genes encoding XRCC1 include NCBI gene 7515 and compliments or variants thereof.

Genes encoding Ku70 include NCBI gene 2547 and compliments or variants thereof. Genes encoding Ku80 include NCBI gene 2547 and compliments or variants thereof. Genes encoding DNA ligase IV include NCBI gene 3981 and compliments or variants thereof. Genes encoding XRCC4 include NCBI gene 7518 and compliments or variants thereof. Useful sequence data for human PARP1 protein and human PARP1 mRNA is described in U.S. Patent Document No. 20120277110 (Ser. No. 13/386,474), entitled "PARP and Adjuvant Cisplatin-Based Chemotherapy in Non-Small-Cell Lung Cancer", which is hereby incorporated by reference in its entirety.

The nucleic acid array described above is used to determine an expression pattern profile for transcripts or partial transcripts of each member of the one or more prognostic gene sets. The transcripts or partial transcripts are derived from a sample taken from a subject suffering from a breast cancer tumor and the expression pattern profile is compared to a reference expression pattern profile. A determination that the sample's expression levels of PARP1 and/or DNA ligase IIIα is equal to or exceeds its corresponding gene expression reference value, and that the sample's expression levels of Ku70 and/or DNA ligase IV is equal to or less than its corresponding gene expression reference value, indicates that the subject's breast cancer tumor is non-responsive to anti-estrogen mono or co-therapy.

In certain embodiments, the probe sequences hybridize under stringent or non-stringent conditions to mRNA corresponding to each member of one or more prognostic gene sets. In other embodiments, the probe sequences hybridize under stringent or non-stringent conditions to cDNA corresponding to each member of one or more of the prognostic gene sets.

In another embodiment, the invention provides a method of classifying a subject's breast cancer tumor as being either responsive or non-responsive to anti-estrogen mono or co-therapy, the method comprising:
(a) determining the expression level in a sample obtained from the subject of transcripts or partial transcripts of each member of one or more of prognostic gene sets described above, thereby deriving an expression pattern profile; and
(b) comparing the expression pattern profile to a reference expression pattern profile; wherein a determination that the sample's expression levels of at least one member of the gene sets is equal to or exceeds its corresponding gene expression reference value indicates that the subject's breast cancer tumor is non-responsive to anti-estrogen mono or co-therapy.

In certain embodiments, derivation of the expression pattern profile and comparison of the expression pattern profile to the reference expression pattern profile involves application of an algorithm to expression level values of the transcripts or partial transcripts of each member of one or more prognostic gene sets. Typically, a comparison of the expression pattern profile to a reference expression pattern profile which shows an increased level of expression of the transcripts or partial transcripts of each member of one or more of the prognostic gene sets indicates that the subject's breast cancer tumor is non-responsive to anti-estrogen mono or co-therapy.

In certain embodiments, the step of determining the expression level of the transcripts or partial transcripts of each member of one or more prognostic gene sets involves preparation from the sample of mRNA corresponding to each member of one or more prognostic gene sets. In other embodiments, the mRNA is copied by reverse transcriptase to generate cDNA, which is amplified by quantitative PCR. The step of determining the expression level of the transcripts or partial transcripts of each member of one or more prognostic gene sets can also involve preparation from the sample of polypeptides encoded by each member of one or more of the prognostic gene sets. Polypeptide expression levels can be determined by antibody detection or other techniques that are well-known to those of ordinary skill in the art.

In another embodiment, the invention provides a system for expression-based classification of a breast cancer tumor as being either responsive or non-responsive to anti-estrogen mono or co-therapy, the system comprising polynucleotide sequences corresponding to, or complementary to, transcripts or partial transcripts of each member of one or more prognostic gene sets described above. The polynucleotide sequences used in these systems can also hybridize under stringent or non-stringent conditions to mRNA transcripts or mRNA partial transcripts of each member of one or more of the prognostic gene sets. Or the polynucleotide sequences can hybridize under stringent or non-stringent conditions to cDNA transcripts or cDNA partial transcripts of each member of one or more prognostic gene sets.

In still another embodiment, the invention provides a computer-readable medium comprising one or more digitally-encoded expression pattern profiles representative of the level of expression of transcripts or partial transcripts of each member of one or more of the prognostic gene sets described above. Each of the one or more expression pattern profiles is associated with a value that is correlated with a reference expression pattern profile to yield a predictor of whether a breast cancer tumor is responsive or non-responsive to anti-estrogen mono or co-therapy.

In still another embodiment, the invention provides a method of determining whether a subject's breast cancer tumor is responsive or non-responsive to anti-estrogen mono or co-therapy, the method comprising:
(a) assaying a sample obtained from the subject to determine the expression level of transcripts or partial transcripts of each member of one or more prognostic gene sets described above, thereby deriving an expression pattern profile; and
(b) comparing the expression pattern profile to a reference expression pattern profile.
wherein a comparison of the expression pattern profile to a reference expression pattern profile which shows an increased level of expression of the transcripts or partial transcripts of each member of one or more prognostic gene sets indicates that the subject's breast cancer tumor is non-responsive to anti-estrogen mono or co-therapy.

In certain embodiments, assaying of the sample comprises gene expression by an array. Assaying of the sample can also comprise preparing mRNA from the sample; the mRNA can be copied by reverse transcription PCR (RT-PCR) to produce cDNA and then amplified by quantitative PCR.

One or more of the steps of the methods described herein can be performed in silica. Representative, non-limiting samples include samples of breast tissue or peripheral blood.

In still another embodiment, the invention provides a kit for characterizing the expression level of transcripts or partial transcripts of each member of one or more of the prognostic gene sets described above, the kit comprising:
(a) each member of one or more of the prognostic gene sets or a complement thereto; and/or
(b) mRNA forms of each member of one or more of the prognostic gene sets or a complement thereto; and/or
(c) polypeptides encoded by each member of one or more of the prognostic gene sets or a complement thereto; and optionally
(d) instructions for correlating the expression level of (i) each member of one or more of the prognostic gene sets or a complement thereto, and/or
(ii) mRNA forms of each member of one or more of the prognostic gene sets or a complement thereto, and/or (iii) polypeptides encoded by each member of one or more of the prognostic gene sets or a complement thereto with the effectiveness of anti-estrogen mono or co-therapy in treating a breast cancer tumor.

In still another embodiment, the invention provides a device for determining whether a breast cancer tumor is responsive to anti-estrogen mono or co-therapy, the device comprising:
(a) means for measuring the expression level of transcripts or partial transcripts of each member of one or more of the prognostic gene sets described above;

(b) means for correlating the expression level with a classification of breast cancer tumor status; and
(c) means for outputting the breast cancer tumor status;
wherein the device optionally utilizes an algorithm to characterize the expression level.

Preferably, the reference expression pattern profile is determined by application of an algorithm to control sample expression level values of transcripts or partial transcripts of each member of one or more of the prognostic gene sets. Details regarding non-limiting useful algorithms are provided hereinafter.

In another embodiment, the invention provides a method of treating a subject who suffers from a pancreatic cancer (e.g. pancreas adenocarcinoma) which is non-responsive to chemotherapy and/or radiation comprising co-administering a therapeutically effective amount of PARP1 inhibitor and a DNA ligase IIIα inhibitor to the subject. In certain aspects of this embodiment, the PARP1 inhibitor and a DNA ligase IIIα inhibitor are co-administered to the subject and the subject cannot tolerate either chemotherapy or radiation. In a preferred aspect of this embodiment, the DNA ligase III inhibitor L67 and the PARP inhibitor ABT888 are co-administered to the subject.

In still another embodiment, the invention provides a method of treating a subject suffering from a chemotherapy and/or radiation-naive pancreatic cancer (e.g. pancreas adenocarcinoma) whose cells over-express one or more ALT NHEJ factors, including PARP1 and DNA ligase IIIα comprising co-administering a therapeutically effective amount of PARP1 inhibitor and a DNA ligase IIIα inhibitor to the subject.

In still another embodiment, the invention provides a method of treating a subject suffering from a chemotherapy and/or radiation-naive pancreatic cancer (e.g. pancreas adenocarcinoma) whose cells over-express one or more ALT NHEJ factors and under-express one or more DNA-PK-dependent NHEJ factors comprising co-administering a therapeutically effective amount of PARP1 inhibitor and a DNA ligase IIIα inhibitor to the subject. The ALT NHEJ factors include, but are not limited to, PARP1 and DNA ligase IIIα and the DNA-PK-dependent NHEJ factors include, but are not limited to, Ku70 and DNA Ligase IV.

In still another embodiment, the invention provides a method of treating a subject suffering from a chemotherapy and/or radiation-naive pancreatic cancer (e.g. pancreas adenocarcinoma) whose cells, based on an evaluation of clinical factors selected from the group consisting of age, tumor size, abdominal pain, weight loss, jaundice, insulin and/or lipid imbalances and co-morbidities, are considered likely to over-express one or more ALT NHEJ factors, including, but not limited to, PARP1 and DNA ligase IIIα.

In still another embodiment, the invention provides a method of treating a subject suffering from a chemotherapy and/or radiation-naive pancreatic cancer (e.g. pancreas adenocarcinoma) whose cells, based on an evaluation of clinical factors selected from the group consisting of age, tumor size, abdominal pain, weight loss, jaundice, insulin and/or lipid imbalances and co-morbidities, are considered likely to over-express one or more ALT NHEJ factors (including, but not limited to, PARP1) and to under-express one or more DNA-PK-dependent NHEJ factors (including, but not limited to, Ku70 and DNA Ligase IV) comprising co-administering a therapeutically effective amount of PARP1 inhibitor and a DNA ligase IIIα inhibitor to the subject.

In still another embodiment, the invention provides a method of treating a subject suffering from a treatment-naive pancreatic cancer (e.g. pancreas adenocarcinoma) whose cells over-express one or more ALT NHEJ factors, including PARP1 and DNA ligase IIIα comprising co-administering a therapeutically effective amount of PARP1 inhibitor and a DNA ligase IIIα inhibitor to the subject.

In still another embodiment, the invention provides a method of treating a subject suffering from a treatment-naive pancreatic cancer (e.g. pancreas adenocarcinoma) whose cells over-express one or more ALT NHEJ factors (including, but not limited to, PARP1) and under-express one or more DNA-PK-dependent NHEJ factors (including, but not limited to, Ku70 and DNA Ligase IV) comprising co-administering a therapeutically effective amount of PARP1 inhibitor and a DNA ligase IIIα inhibitor to the subject.

In still another embodiment, the invention provides a method of treating a subject suffering from a treatment-naive pancreatic cancer (e.g. pancreas adenocarcinoma) whose cells, based on an evaluation of clinical factors selected from the group consisting of age, tumor size, abdominal pain, weight loss, jaundice, insulin and/or lipid imbalances and co-morbidities, are considered likely to over-express one or more ALT NHEJ factors (including, but not limited to, PARP1) and to under-express one or more DNA-PK-dependent NHEJ factors (including, but not limited to, Ku70 and DNA Ligase IV) comprising co-administering a therapeutically effective amount of PARP1 inhibitor and a DNA ligase IIIα inhibitor to the subject.

In still another embodiment, the invention provides a method of classifying a subject's pancreatic cancer (e.g. pancreas adenocarcinoma) as either responsive or non-responsive to chemotherapy and/or radiation, the method comprising:
(a) determining the ALT NHEJ factor expression level (e.g. by measuring RNA transcript levels) in a pancreas adenocarcinoma sample obtained from the subject; and
(b) comparing the expression level to a reference expression pattern profile;
wherein a determination that the sample's ALT NHEJ factor expression level exceeds its corresponding expression reference value indicates that the subject's pancreatic cancer (e.g. pancreas adenocarcinoma) is not responsive to chemotherapy and/or radiation.

In still another embodiment, the invention provides a method of classifying a subject's pancreatic cancer (e.g. pancreas adenocarcinoma) as being either responsive or non-responsive to chemotherapy and/or radiation, the method comprising:
(a) determining the ALT NHEJ factor expression level and the DNA-PK-dependent NHEJ factor expression level in a pancreas adenocarcinoma sample obtained from the subject; and
(b) comparing the ALT NHEJ factor and DNA-PK-dependent NHEJ factor expression levels to a reference expression pattern profile;
wherein a determination that (1) the sample's ALT NHEJ factor expression level exceeds its corresponding expression reference value, and (2) the sample's DNA-PK-dependent NHEJ factor expression level is less than corresponding expression reference value indicates that the subject's pancreatic cancer (e.g. pancreas adenocarcinoma) is not responsive to chemotherapy and/or radiation.

In still another embodiment, the invention provides a method of classifying a subject's pancreatic cancer (e.g. pancreas adenocarcinoma) as being either responsive or non-responsive to chemotherapy and/or radiation, the method comprising:
(a) determining the expression level of DNA-PK-dependent NHEJ proteins Ku70 and DNA ligase IV in a pancreas adenocarcinoma sample obtained from the subject; and (b) comparing the expression level to a reference expression pattern profile;

wherein a determination that the sample's expression level of DNA-PK-dependent NHEJ proteins Ku70 and DNA ligase IV is less than its corresponding expression reference value indicates that the subject's pancreatic cancer (e.g. pancreas adenocarcinoma) is not responsive to chemotherapy and/or radiation.

In still another embodiment, the invention provides a nucleic acid array for expression-based classification of a pancreatic cancer (e.g. pancreas adenocarcinoma) as being either responsive or non-responsive to chemotherapy and/or radiation, the array comprising at least about 10 and up to about 250 or more probes immobilized on a solid support, each of the probes:

(a) having a length of between about 25 to about 50 or more (up to about 250 or more) nucleotides; and (b) being derived from sequences corresponding to, or complementary to, transcripts or partial transcripts of each member of one or more prognostic gene sets comprised of genes encoding PARP1 or DNA ligase IIIα.

In still another embodiment, the invention provides a nucleic acid array for expression-based classification of a pancreatic cancer (e.g. pancreas adenocarcinoma) as being either responsive or non-responsive to chemotherapy and/or radiation, the array comprising at least about 20 and up to about 250 or more probes immobilized on a solid support, each of the probes:

(a) having a length of between about 25 to about 50 or more (up to about 250 or more) nucleotides; and (b) being derived from sequences corresponding to, or complementary to, transcripts or partial transcripts of each member of one or more prognostic gene sets comprised of genes encoding PARP1, PARP2, PARP3, DNA ligase IIIα, XRCC1, Ku70, Ku80, XRCC4 and DNA ligase IV In the nucleic acid arrays described above, the probe sequences can hybridize under stringent or non-stringent conditions to mRNA corresponding to each member of one or more of the prognostic gene sets.

In still another embodiment, the invention provides a method of determining whether a subject's pancreatic cancer (e.g. pancreas adenocarcinoma) is responsive or non-responsive to chemotherapy and/or radiation, the method comprising:

(a) assaying a sample obtained from the subject to determine the expression level of transcripts or partial transcripts of each member of one or more prognostic gene sets comprised of genes encoding PARP1, DNA ligase IIIα, Ku70 and DNA ligase IV, thereby deriving an expression pattern profile; and (b) comparing the expression pattern profile to a reference expression pattern profile.

wherein a comparison of the expression pattern profile to a reference expression pattern profile which shows an increased level of expression of the transcripts or partial transcripts of each member of one or more prognostic gene sets indicates that the subject's pancreatic cancer (e.g. pancreas adenocarcinoma) is non-responsive to chemotherapy and/or radiation.

In the method described above, assaying of the sample can comprise gene expression by an array, or assaying of the sample can comprise preparing mRNA from the sample and amplifying the mRNA by quantitative PCR or reverse transcription PCR (RT-PCR) to produce cDNA. Optionally, at least one step of the method is performed in silica.

In still another embodiment, the invention provides a kit for characterizing the expression level of transcripts or partial transcripts of each member of one or more of the prognostic gene sets comprised of genes encoding PARP1, DNA ligase IIIα, Ku70 and DNA ligase IV, the kit comprising:

(a) each member of one or more of the prognostic gene sets or a complement thereto; and/or (b) mRNA forms of each member of one or more of the prognostic gene sets or a complement thereto; and/or (c) polypeptides encoded by each member of one or more of the prognostic gene sets or a complement thereto; and optionally (d) instructions for correlating the expression level of (i) each member of one or more of the prognostic gene sets or a complement thereto, and/or (ii) mRNA forms of each member of one or more of the prognostic gene sets or a complement thereto, and/or (iii) polypeptides encoded by each member of one or more of the prognostic gene sets or a complement thereto with the effectiveness of chemotherapy and/or radiation in treating a pancreatic cancer (e.g. pancreas adenocarcinoma).

In still another embodiment, the invention provides a device for determining whether a pancreatic cancer (e.g. pancreas adenocarcinoma) is responsive to chemotherapy and/or radiation, the device comprising:

(a) means for measuring the expression level of transcripts or partial transcripts of each member of one or more of the prognostic gene sets comprised of genes encoding PARP1, DNA ligase IIIα, Ku70 and DNA ligase IV;

(b) means for correlating the expression level with a classification of pancreas adenocarcinoma status; and (c) means for outputting the pancreatic cancer (e.g. pancreas adenocarcinoma) status;

wherein the device optionally utilizes an algorithm to characterize the expression level.

In the device described above, a reference expression pattern profile can be determined by application of an algorithm to control sample expression level values of transcripts or partial transcripts of each member of one or more of the prognostic gene sets.

In still another embodiment, the invention provides a computer-readable medium comprising one or more digitally-encoded expression pattern profiles representative of the level of expression of transcripts or partial transcripts of each member of one or more prognostic gene sets comprised of genes encoding PARP1, DNA ligase IIIα, Ku70 and DNA ligase IV, wherein each of the one or more expression pattern profiles is associated with a value that is correlated with a reference expression pattern profile to yield a predictor of whether a pancreatic cancer (e.g. pancreas adenocarcinoma) is responsive or non-responsive to chemotherapy and/or radiation.

In still another embodiment, the invention provides a pharmaceutical dosage form comprising therapeutically amounts of at least one PARP1 inhibitor and at least one DNA ligase IIIα inhibitor and, optionally, one or more excipients, wherein therapeutically amounts of the at least one PARP1 inhibitor and the at least one DNA ligase IIIα inhibitor are defined by dosages of those inhibitors that are necessary to ameliorate symptoms of a breast cancer or pancreatic cancer (e.g. pancreas adenocarcinoma).

These and other aspects of the invention are described further in the Detailed Description of the Invention.

BRIEF DESCRIPTION OF THE FIGURES

FIG. 8. Sequencing of DSB repair junction in A, MCF10A, B, MCF7 and C, TAM1 treated with L67+ABT888 (Right panel) compared to CRTL (Left panel). Sequences (0 to −30 bp to the left and 1 to +30 bp to the right of the junction) are indicated in the top line of each Figure in the substrate and in black in the repair products. Repair products are shown with base pair positions numbered and represent large deletions that occur outside the substrate depicted in the top line of each Figure. The base pair positions where each large deletion begins are calculated from the break point in the substrate.

DETAILED DESCRIPTION OF THE INVENTION

Figure 1:
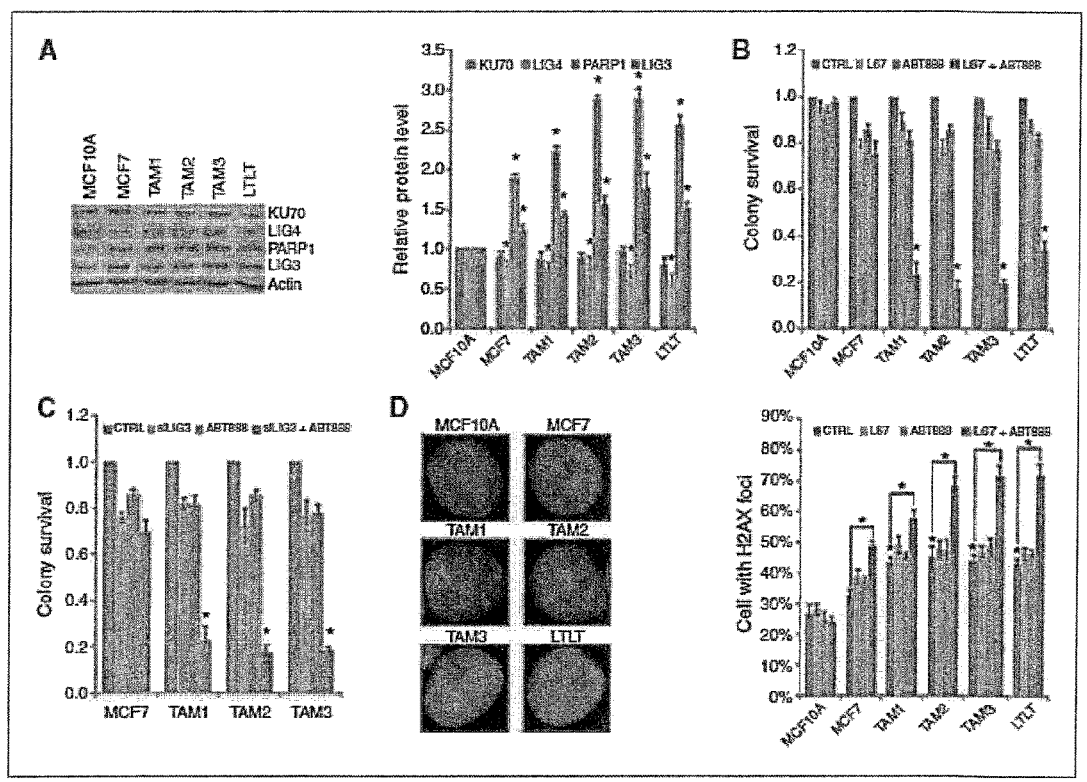
FIG. 1. A, left: representative Western blot and, right, relative steady-state levels of Ku70, DNA ligase IV, PARP1, and DNA ligase IIIα proteins in cell extracts from nontumorigenic breast epithelial MCF10A cells, MCF7 breast cancer cells and, tamoxifen (TAM1, TAM2, and TAM3) and LTLT-resistant derivatives of MCF7. B, colony survival of MCF10A, MCF7, TAM1, TAM2, TAM3, and LTLT cells after a 10-day growth in the presence of L67 (0.5 µmol/L) and/or ABT888 (0.125 µmol/L). C, colony survival of MCF7, TAM1, TAM2, and TAM3 following siRNA knockdown of DNA ligase IIIα alone and in combination with ABT888 (0.125 µmol/L). D, left: representative nuclei from MCF10A, MCF7, TAM1, TAM2, TAM3, and LTLT cells immunostained for H2AX foci (red) in the presence of L67 and/or ABT888. Nuclei counterstained with DAPI (blue). D, right: the percentage of cells with endogenous foci. Results are representative of the mean of 3 independent experiment±SEM; *, P<0.05 by t test.

The following terms are used throughout the specification to describe the present invention. Where a term is not given a specific definition herein, that term is to be given the same meaning as understood by those of ordinary skill in the art. The definitions given to the disease states or conditions which may be treated using one or more of the compounds according to the present invention are those which are generally known in the art.

The singular forms "a," "an," and "the," include plural referents unless expressly and unequivocally limited to one referent. Thus, for example, reference to "an inhibitor" can include two or more different compounds. As used herein, the term "include" and its grammatical variants are intended to be non-limiting, such that recitation of items in a list is not to the exclusion of other like items that can be substituted or other items that can be added to the listed items.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

In accordance with the present invention there may be employed conventional molecular biology, microbiology, and recombinant DNA techniques within the skill of the art. Such techniques are explained fully in the literature. See, e.g., Sambrook et al, 2001, "Molecular Cloning: A Laboratory Manual"; Ausubel, ed., 1994, "Current Protocols in Molecular Biology" Volumes I-III; Celis, ed., 1994, "Cell Biology: A Laboratory Handbook" Volumes I-III; Coligan, ed., 1994, "Current Protocols in Immunology" Volumes I-III; Gait ed., 1984, "Oligonucleotide Synthesis"; Hames & Higgins eds., 1985, "Nucleic Acid Hybridization"; Hames & Higgins, eds., 1984, "Transcription And Translation"; Freshney, ed., 1986, "Animal Cell Culture"; IRL Press, 1986, "Immobilized Cells And Enzymes"; Perbal, 1984, "A Practical Guide To Molecular Cloning."

As used herein, the term "polynucleotide" refers to a polymeric form of nucleotides of any length, either ribonucleotides or deoxynucleotides, and includes both double- and single-stranded DNA and RNA. A polynucleotide may include nucleotide sequences having different functions, such as coding regions, and non-coding regions such as regulatory sequences (e.g., promoters or transcriptional terminators). A polynucleotide can be obtained directly from a natural source, or can be prepared with the aid of recombinant, enzymatic, or chemical techniques. A polynucleotide can be linear or circular in topology. A polynucleotide can be, for example, a portion of a vector, such as an expression or cloning vector, or a fragment.

As used herein, the term "polypeptide" refers broadly to a polymer of two or more amino acids joined together by peptide bonds. The term "polypeptide" also includes molecules which contain more than one polypeptide joined by a disulfide bond, or complexes of polypeptides that are joined together, covalently or noncovalently, as multimers (e g., dimers, tetramers). Thus, the terms peptide, oligopeptide, and protein are all included within the definition of polypeptide and these terms are used interchangeably. It should be understood that these terms do not connote a specific length of a polymer of amino acids, nor are they intended to imply or distinguish whether the polypeptide is produced using recombinant techniques, chemical or enzymatic synthesis, or is naturally occurring.

The term "patient" or "subject" is used throughout the specification to describe an animal, preferably a human, to whom treatment, including prophylactic treatment, with the compositions according to the present invention is provided. For treatment of those infections, conditions or disease states which are specific for a specific animal such as a human patient, the term patient refers to that specific animal.

Purely by way of example, a comparison of the expression pattern profile to a reference expression pattern profile which shows differences in the level of expression of the transcripts or partial transcripts of each member of one or more prognostic gene sets can reflect expression level differences of about between about 5-10%, or about 10-15%, or about 15-20%, or about 20-25%, or about 25-30%, or about 30-35%, or about 35-40%, or about 40-45%, or about 45-50%, or about 50-55%, or about 55-60%, or about 60-65%, or about 65-70%, or about 70-75%, or about 75-80%, or about 80-85%, or about 85-90%, or about 90-95%, or about 95-100%, or about 100-110%, or about 110-120%, or about 120-130%, or about 130-140%, or about 140-150%, or about 150-160%, or about 160-170%, or about 170-180%, or about 180-190%, or 190-200%, or 200-210%, or 210-220%, or 220-230%, or 230-240%, or 240-250%, or 250-260%, or about 260-270%, or about 270-280%, or about 280-290%, or about 290-300%, or differences in the level of expression of the transcripts or partial transcripts of each member of one or more prognostic gene sets can reflect expression level differences of about between about ±50% to about ±0.5%, or about ±45% to about ±1%, or about ±40% to about ±1.5%, or about ±35% to about ±2.0%, or about ±30% to about ±2.5%, or about ±25% to about ±3.0%, or about ±20% to about ±3.5%, or about ±15% to about ±4.0%, or about ±10% to about ±5.0%, or about ±9% to about ±1.0%, or about ±8% to about ±2%, or about ±7% to about ±3%, or about ±6% to about ±5%, or about ±5%, or about ±4.5%, or about ±4.0%, or about ±3.5%, or about ±3.0%, or about ±2.5%, or about ±2.0%, or about ±1.5%, or about ±1.0%.

The terms "arrays", "microarrays", and "DNA chips" are used herein interchangeably to refer to an array of distinct polynucleotides affixed to a substrate, such as glass, plastic, paper, nylon or other type of membrane, filter, chip, or any other suitable solid support. The polynucleotides can be synthesized directly on the substrate, or synthesized separate from the substrate and then affixed to the substrate. In one embodiment, the microarray is prepared and used according to the methods described in U.S. Pat. No. 5,837,832, Chee et al., PCT application WO95/11995 (Chee et al.), Lockhart, D. J. et al. (1996; Nat. Biotech. 14: 1675-1680) and Schena, M. et al. (1996; Proc. Natl. Acad. Sci. 93: 10614-10619), all of which are incorporated herein in their entirety by reference. In other embodiments, such arrays are produced by the methods described by Brown et al., U.S. Pat. No. 5,807,522.

Nucleic acid arrays are reviewed in the following references: Zammatteo et al., "New chips for molecular biology and diagnostics", Biotechnol Annu Rev. 2002; 8:85-101; Sosnowski et al., "Active microelectronic array system for DNA hybridization, genotyping and pharmacogenomic applications", Psychiatr Genet. 2002 December; 12(4):181-92; Heller, "DNA microarray technology: devices, systems, and applications", Annu Rev Biomed Eng. 2002; 4: 129-53. Epub 2002 Mar. 22; Kolchinsky et al., "Analysis of SNPs and other genomic variations using gel-based chips", Hum Mutat. 2002 April; 19(4):343-60; and McGall et al., "High-density genechip oligonucleotide probe arrays", Adv Biochem Eng Biotechnol. 2002; 77:21-42.

Any number of probes, such as allele-specific probes, may be implemented in an array, and each probe or pair of probes can hybridize to a different SNP position. In the case of polynucleotide probes, they can be synthesized at designated areas (or synthesized separately and then affixed to designated areas) on a substrate using a light-directed chemical process. Each DNA chip can contain, for example, thousands to millions of individual synthetic polynucleotide probes arranged in a grid-like pattern and miniaturized (e.g., to the size of a dime). Preferably, probes are attached to a solid support in an ordered, addressable array.

A microarray can be composed of a large number of unique, single-stranded polynucleotides, usually either synthetic antisense polynucleotides or fragments of cDNAs, fixed to a solid support. Typical polynucleotides are preferably about 25 to about 50 nucleotides in length, often about 25 to about 40 nucleotides in length, more preferably about 25 nucleotides in length, and most preferably about 40 nucleotides in length. For certain types of microarrays or other detection kits/systems, it may be preferable to use oligonucleotides that are only about 25-30 nucleotides in length.

In other types of arrays, such as arrays used in conjunction with chemiluminescent detection technology, preferred probe lengths can be, for example, about 25-50 nucleotides in length, preferably about 25-40 nucleotides in length, more preferably about 25-35 nucleotides in length, and most preferably about 30 nucleotides in length. The microarray or detection kit can contain polynucleotides that cover the known 5' or 3' sequence of a gene/transcript or target, sequential polynucleotides that cover the full-length sequence of a gene/transcript; or unique polynucleotides selected from particular areas along the length of a target gene/transcript sequence. Polynucleotides used in the microarray or detection kit can be specific to a gene/transcript or target of interest.

Hybridization assays based on polynucleotide arrays rely on the differences in hybridization stability of the probes to perfectly matched and mismatched target sequence variants. It is generally preferable that stringency conditions used in hybridization assays are high enough such that nucleic acid molecules that differ from one another at as little as a single gene/transcript or target position can be differentiated. Representative high stringency conditions are described herein and well known to those skilled in the art and can be found in, for example, Current Protocols in Molecular Biology, John Wiley & Sons, N.Y. (1989), 6.3.1-6.3.6.

In other embodiments, the arrays are used in conjunction with chemiluminescent detection technology. The following patents and patent applications, which are all hereby incorporated by reference, provide additional information pertaining to chemiluminescent detection: U.S. patent application Ser. Nos. 10/620,332 and 10/620,333 describe chemiluminescent approaches for microarray detection; U.S. Pat. Nos. 6,124,478, 6,107,024, 5,994,073, 5,981,768, 5,871,938, 5,843,681, 5,800,999, and 5,773,628 describe methods and compositions of dioxetane for performing chemiluminescent detection; and U.S. published application US2002/0110828 discloses methods and compositions for microarray controls.

In one embodiment of the invention, a nucleic acid array can comprise an array of probes of about 25-50 nucleotides in length or more (up to about 250 or more). In further embodiments, a nucleic acid array can comprise any number of probes, in which at least one probe is capable of detecting one or more sequences described herein, or a fragment of such sequences comprising at least about 25 consecutive nucleotides to upwards of 250 nucleotides, preferably about 25 to about 50 consecutive nucleotides, preferably about 25 to about 40 consecutive nucleotides, or 26, 27, 28, 29, 30, 31, 32, 33, 34, 35, 36, 37, 38, 39 or 40, up to about 50 more preferably about 25, 26, 27, 28, 29 or 30 or more up to about 250 or more consecutive nucleotides (or any other number in-between).

A polynucleotide probe can be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 25, 30, 40, 45, 50 or more polynucleotides, or any other number which lends itself to the efficient use of commercially available instrumentation.

As indicated above, reference expression pattern profiles are preferably determined by application of an algorithm to control sample expression level values of transcripts or partial transcripts of each member of one or more of the first, second, third or fourth prognostic gene sets. In non-limiting examples, such algorithms can be derived as shown in the examples herein and may be optimization algorithms such as a mean variance algorithm, and/or may be heuristic, and or may be a repeatability based meta-analysis classification algorithm, and/or may be a classifier algorithm.

In certain embodiments, illustrative algorithms include but are not limited to methods that reduce the number of variables such as principal component analysis algorithms, partial least squares methods, and independent component analysis algorithms. Illustrative algorithms further include but are not limited to methods that handle large numbers of variables directly such as statistical methods and methods based on machine learning techniques. Statistical methods include penalized logistic regression, prediction analysis of microarrays (PAM), methods based on shrunken centroids, support vector machine analysis, and regularized linear discriminant analysis. Machine learning techniques include bagging procedures, boosting procedures, random forest algorithms, and combinations thereof. In some embodiments of the present invention a support vector machine (SVM) algorithm, a random forest algorithm, or a combination thereof is used for classification of microarray data. In some embodiments, identified markers that distinguish samples or subtypes are selected based on statistical significance. In some cases, the statistical significance selection is performed after applying a Benjamini Hochberg correction for false discovery rate (FDR).

Those of ordinary skill in the art know how to apply the aforementioned and other algorithmic techniques to the members of the one or more of the first, second, third or fourth prognostic gene sets to derive useful algorithms.

In some cases, the classifier algorithm may be supplemented with a meta-analysis approach such as that described by Fishel and Kaufman et al. 2007 Bioinformatics 23(13): 1599-606. Also, the classifier algorithm may be supplemented with a meta-analysis approach such as a repeatability analysis. In some cases, the repeatability analysis selects markers that appear in at least one predictive expression product marker set.

The practice of the present invention may also employ conventional biology methods, software and systems. For example, means for measuring the expression level of transcripts or partial transcripts of each member of one or more prognostic gene sets; means for correlating the expression level with a classification of breast cancer or pancreatic cancer status; and means for outputting the breast cancer or pancreatic cancer status may employ conventional biology methods, software and systems as described herein or as otherwise known to those of ordinary skill in the art.

Computer software products of the invention typically include computer readable medium having computer-executable instructions for performing the logic steps of the method of the invention. Suitable computer readable medium include floppy disk, CD-ROM/DVD/DVD-ROM, hard-disk drive, flash memory, ROM/RAM, magnetic tapes and etc. The computer executable instructions may be written in a suitable computer language or combination of several languages. Basic computational biology methods are described in, for example Setubal and Meidanis et al., Introduction to Computational Biology Methods (PWS Publishing Company, Boston, 1997); Salzberg, Searles, Kasif, (Ed.), Computational Methods in Molecular Biology, (Elsevier, Amsterdam, 1998); Rashidi and Buehler, Bioinformatics Basics: Application in Biological Science and Medicine (CRC Press, London, 2000) and Ouelette and Bzevanis Bioinformatics: A Practical Guide for Analysis of Gene and Proteins (Wiley & Sons, Inc., 2.sup.nd ed., 2001). See U.S. Pat. No. 6,420,108.

The present invention may also make use of various computer program products and software for a variety of purposes, such as probe design, management of data, analysis, and instrument operation. See, e.g. U.S. Pat. Nos. 5,593,839, 5,795,716, 5,733,729, 5,974,164, 6,066,454, 6,090,555, 6,185,561, 6,188,783, 6,223,127, 6,229,911 and 6,308,170.

Additionally, the present invention relates to embodiments that include methods for providing information over networks such as the Internet. For example, the components of the system may be interconnected via any suitable means including over a network, e.g. the ELISA plate reader to the processor or computing device. The processor may take the form of a portable processing device that may be carried by an individual user e.g. lap top, and data can be transmitted to or received from any device, such as for example, server, laptop, desktop, PDA, cell phone capable of receiving data, BLACK-BERRY®, and the like. In some embodiments of the invention, the system and the processor may be integrated into a single unit. In another example, a wireless device can be used to receive information and forward it to another processor over a telecommunications network, for example, a text or multi-media message.

The functions of the processor need not be carried out on a single processing device. They may, instead be distributed among a plurality of processors, which may be interconnected over a network. Further, the information can be encoded using encryption methods, e.g. SSL, prior to transmitting over a network or remote user. The information required for decoding the captured encoded images taken from test objects may be stored in databases that are accessible to various users over the same or a different network.

In some embodiments, the data is saved to a data storage device and can be accessed through a web site. Authorized users can log onto the web site, upload scanned images, and immediately receive results on their browser. Results can also be stored in a database for future reviews.

In some embodiments, a web-based service may be implemented using standards for interface and data representation, such as SOAP and XML, to enable third parties to connect their information services and software to the data. This approach would enable seamless data request/response flow among diverse platforms and software applications.

The terms "compound" or inhibitor used herein to refer to any specific chemical compound, antibody or complex disclosed herein or otherwise known to those of ordinary skill in the art. When the term refers to a single small molecule it includes stereoisomers and/or optical isomers (including racemic mixtures) of that molecule, as well as active metabolites and/or pharmaceutically active salts thereof.

The term "inhibitor" is used herein to refer to any compound which inhibits an ALT NHEJ factor by any mechanism, direct or indirect, e.g. by inhibition of the interaction of PARP1 or DNA ligase IIIα transporter proteins with their intended receptor or other target or by inhibition of the expression of PARP1 or DNA ligase IIIα transporter proteins. "Poly [ADP-Ribose] Polymerase 1 (PARP1) inhibitors" include, but are not limited to, nicotinamide; NU1025; 3-aminobenzamide; 4-amino-1,8-naphthalimide; 1,5-isoquinolinediol; 6(5H)-phenanthriddinone; 1,3,4,5,-tetrahydrobenzo (c)(1,6)- and (c)(1,7)-naphthyridin-6 ones; adenosine substituted 2,3-dihydro-1H-isoindol-1-ones; AG14361; AG014699; 2-(4-chlorophenyl)-5-quinoxalinecarboxamide; 5-chloro-2-[3-(4-phenyl-3,6-dihydro-1(2H)-pyridinyl)propyl]-4(3H)-quinazolinone; isoindolinone derivative INO-1001; 4-hydroxyquinazoline; 2-[3-[4-(4-chlorophenyl) 1-piperazinyl]propyl]-4-3(4)-quinazolinone; 1,5-dihydroxy-isoquinoline (DHIQ); 3,4-dihydro-5 [4-(1-piperidinyl)(butoxy)-1(2H)-isoquinolone; CEP-6800; GB-15427; PJ34; DPQ; BS-201; AZD2281 (Olaparib); BS401; CHP101; CHP102; INH2BP; BSI201; BSI401; TIQ-A; an imidazobenzodiazepine; 8-hydroxy-2-methylquinazolinone (NU1025), CEP 9722, MK 4827, LT-673; 3-aminobenzamide; Olaparib (AZD2281; ABT-888 (Veliparib); BSI-201 (Iniparib); Rucaparib (AG-014699); INO-1001; A-966492; PJ-34; and PARP1 inhibitors described in U.S. patent application Ser. No. 12/576,410.

"DNA ligase IIIα inhibitors" include, but are not limited to, the DNA ligase III inhibitors L67, L-67-5 and L67-6 of Table 9 of U.S. Patent Application Document No. 20100099683, and the DNA ligase IIIα inhibitors identified in Xi, et al., Rational Design of Human DNA Ligase Inhibitors that Target Cellular DNA Replication and Repair Cancer Res 2008; 68(9):3169-77 and GEG54, another derivative of L67.

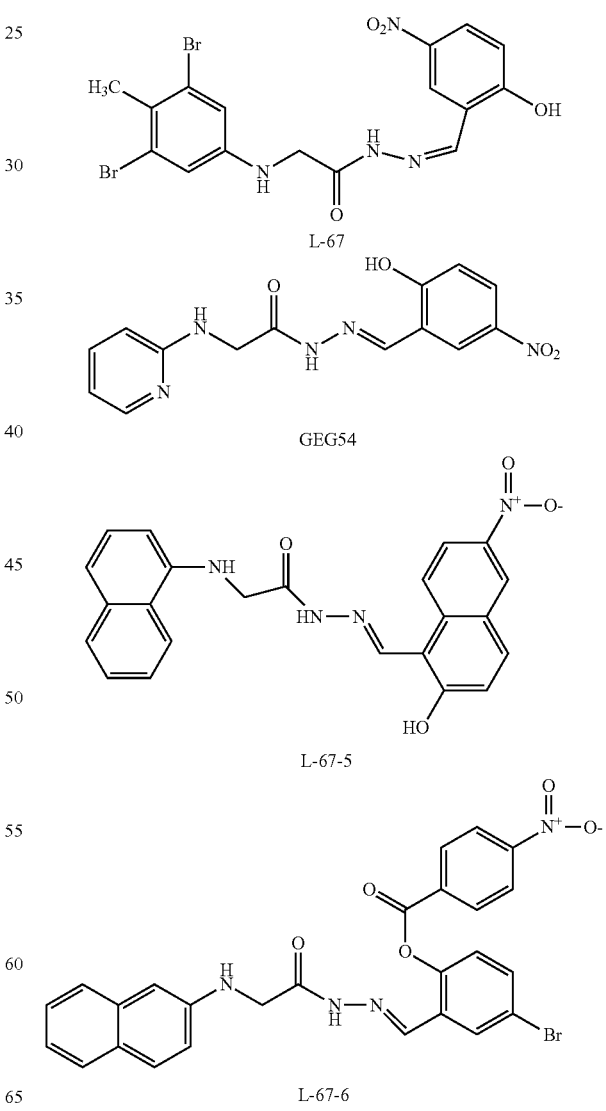

The terms "effective amount" or "pharmaceutically effective amount" are used throughout the specification to describe concentrations or amounts of compounds or other components which are used in amounts, within the context of their use, to produce an intended effect according to the present invention. The compound or component may be used to produce a favorable change in a disease or condition treated, whether that change is a remission, a favorable physiological result, a reversal or attenuation of a disease state or condition treated, the prevention or the reduction in the likelihood of a condition or disease-state occurring, depending upon the disease or condition treated. Where compounds are used in combination, each of the compounds is used in an effective amount, wherein an effective amount may include a synergistic amount. In many instances, the term effective amount refers to that amount which inhibits expression of PARP1 or DNA ligase IIIα transporter proteins, or improves the status of a breast cancer or pancreatic cancer (e.g. pancreas adenocarcinoma) and consequently, results in a diminution of resistance to a therapeutic approach, e.g. to symptoms or results in an improvement of symptoms associated with a breast cancer tumor which is non-responsive or intrinsically resistant to anti-estrogen therapy or to symptoms of a pancreatic cancer in a subject who is unable to tolerate a chemotherapy regimen.

The amount of PARP1 or DNA ligase IIIα inhibitor used in the present invention may vary according to the nature of the inhibitor, the age and weight of the patient and numerous other factors which may influence the bioavailability and pharmacokinetics of the inhibitor. The amount of inhibitor which is administered to a patient generally ranges from about 0.001 mg/kg to about 50 mg/kg or more, about 0.5 mg/kg to about 25 mg/kg, about 0.1 to about 15 mg/kg, about 1 mg to about 10 mg/kg per day and otherwise described herein. The person of ordinary skill may easily recognize variations in dosage schedules or amounts to be made during the course of therapy.

The term "neoplasia" or "neoplasm" is used throughout the specification to refer to the pathological process that results in the formation and growth of a cancerous or malignant neoplasm, i.e., abnormal tissue that grows by cellular proliferation, often more rapidly than normal and continues to grow after the stimuli that initiated the new growth cease. Malignant neoplasms show partial or complete lack of structural organization and functional coordination with the normal tissue and may invade surrounding tissues. As used herein, the term neoplasia/neoplasm is used to describe all pathological process associated with breast cancer and pancreatic cancer and their metastasis.

The term "prophylactic" is used to describe the use of a compound described herein which reduces the likelihood of an occurrence of a condition or disease state in a patient or subject. The term "reducing the likelihood" refers to the fact that in a given population of patients, the present invention may be used to reduce the likelihood of an occurrence, recurrence or metastasis of disease in one or more patients within that population of all patients, rather than prevent, in all patients, the occurrence, recurrence or metastasis of a disease state.

The term "pharmaceutically acceptable" refers to a salt form or other derivative (such as an active metabolite or prodrug form) of a PARP1 or DNA ligase IIIα inhibitor or a carrier, additive or excipient which is not unacceptably toxic to the subject to which it is administered.

The term "cancer" is used throughout the specification to refer to the pathological process that results in the formation and growth of a cancerous or malignant neoplasm, i.e., abnormal tissue that grows by cellular proliferation, often more rapidly than normal and continues to grow after the stimuli that initiated the new growth cease. Malignant neoplasms show partial or complete lack of structural organization and functional coordination with the normal tissue and most invade surrounding tissues, metastasize to several sites, and are likely to recur after attempted removal and to cause the death of the patient unless adequately treated. As used herein, the term neoplasia is used to describe all cancerous disease states associated with breast cancer and pancreatic cancer and embraces or encompasses the pathological process associated with malignant hematogenous, ascetic and solid tumors.

"Breast cancer" includes ductal carcinoma in situ (DCIS), invasive breast cancer and metastatic. Breast cancers can occur in milk ducts, milk-producing lobules and connective tissues. "Breast cancer" as defined herein includes estrogen receptor (ER) negative and hormone receptor (HR) negative, and also can be categorized as Group 3 (HER-2 positive) or Group 4 (basal-like).

"Pancreatic cancer" includes endocrine and non-endocrine pancreatic cancers, and encompasses pancreatic adenocarcinoma, islet cell carcinoma, and neuroendocrine tumors. A "non-endocrine pancreatic cancer" generally refers to cancers arising from the exocrine pancreatic glands. Pancreatic cancers include pancreatic insulinomas and includes pancreatic carcinoma, pancreatic adenocarcinoma, adenosquamous carcinoma, squamous cell carcinoma and giant cell carcinoma and precursor lesions such as pancreatic intra-epithelial neoplasia (PanIN), mucinous cyst neoplasms (MCN) and intrapancreatic mucinous neoplasms (IPMN), which are neoplastic but not yet malignant.

PARP1 or DNA ligase IIIα inhibitors may be administered in oral, topical, parenteral, intramuscular, intravenous, subcutaneous, transdermal (which may include a penetration enhancement agent), buccal, sublingual and suppository administration, among other routes of administration. Enteric coated oral tablets may also be used to enhance bioavailability of the compounds from an oral route of administration. The most effective dosage form will depend upon the pharmacokinetics of the particular agent chosen as well as the severity of disease in the patient. Administration of compounds according to the present invention as sprays, mists, or aerosols for intra-nasal, intra-tracheal or pulmonary administration may also be used. PARP1 or DNA ligase IIIα inhibitors may be administered in immediate release, intermediate release or sustained or controlled release forms. Sustained or controlled release forms are preferably administered orally, but can also be administered through a variety of other forms. Intramuscular injections in liposomal form may also be used to control or sustain the release of a compound at an injection site.

The invention is illustrated in further in the following non-limiting examples.

EXAMPLES

Materials and Methods

Cell Culture

MCF10A, a nontumorigenic epithelial cell line, was cultured in mammary epithelial cell growth medium (Lonza) Q4 supplemented with the MEGM SingleQuot Kit (BPE, human epidermal growth factor, insulin, and hydrocortione; Lonza, and cholera toxin (100 ng/mL; Sigma). The ER/PR+ breast cancer cell line MCF7 and tamoxifen-resistant derivatives TAM1, TAM2, and TAM3 (kindly provided by Dr. Ben Park, JHU) were cultured in phenol red-free Dulbecco's Modified Eagle's Medium (DMEM)/F12 (1:1) with L-glutamine (Gibco), 5% fetal bovine serum (FBS; Sigma), and 1% penicillin-streptomycin (Invitrogen).

TAM1, TAM2, and TAM3 were grown in the presence of tamoxifen (1 µmol/L; Sigma). Letrozole (LTLT), an aromatase inhibitor-resistant derivative of MCF7 isolated from long-term letrozole-treated xenograft tumors (16), was cultured in phenol red-free IMEM (Gibco) supplemented with 5% dextran-coated charcoal-treated serum (Thermo 115 Scientific), 1% penicillin-streptomycin (Invitrogen), 750 mg/mL G418 (American Bioanalytical), and 1 µmol/L letrozole (kindly provided by Dr. Dean Evans, Novartis Pharma, Basel Switzerland). The metastatic ER/PR/HER2− breast cancer cell line, MDA-MB-231, was cultured in high-glucose DMEM (Gibco) with 1% penicillin-streptomycin (Invitrogen) whereas the ER/PR_ and HER2+ breast cancer cell line, SK-BR-3, was grown in McCoy's 5A modified medium (Stemcell Technologies) with 1% penicillin-streptomycin (Invitrogen). Cells were incubated at 37° C. in 5% CO2.

Validation of Cell Lines

Cell line identification and validation of their clonality was carried out with Promega's Power-Plex 16 Short Tandem Repeat assay system. Samples were amplified by the recommended protocol and run on an Applied Biosystems 3100-Avant Genetic Analyzer with Power-Plex 16 Allelic Ladder mix and internal lane standards, ILS-600. Results were analyzed by GeneMapper ID3.2.

Chemical Synthesis of DNA Ligase I/III Inhibitor L67

The DNA ligase inhibitor L67 (10) was synthesized by incubation of ethyl chloroacetate with 3,5-dibromo-4-methylaniline in the presence of lithium carbonate in N-methyl-2-pyrrolidinone as the solvent at 100° C. for 16 hours to produce N-(3,5-dibromo-4-methylphenyl)glycine ethyl ester in 33% yield after recrystallization from ethanol.

This compound was reacted with hydrazine hydrate in refluxing 1-propanol for 64 hours. The N-(3,5-dibromo-4-methylphenyl)glycine hydrazide produced (48% yield) was loaded onto a silica gel column and eluted with 10% ethanol in ethyl acetate. Condensation of the hydrazide with 5-nitrosalicylaldehyde in ethanol produced L67 in 76% yield. The chemical structure of L67 was confirmed by IH Q5 nuclear magnetic resonance.

Immunofluorescence Staining

Cells were grown on glass chamber slides (Lab-Tek II) and treated with the DNA ligase I/III inhibitor L67 (0.5 µmol/L) 152 and/or the PARP inhibitor ABT888 (0.125 µmol/L; Abbott) for 24 hours. After treatment, cells were washed with PBS and fixed in 1% formaldehyde (P-6148; Sigma) for 10 minutes at room temperature. The cells were permeabilized by incubation in 70% EtOH for 10 minutes at room temperature and then incubated in a humidified chamber at 37° C. for 1 hour in a solution of 10% FBS in TBS-Tween 20 (0.2%). After washing, slides were incubated for 1 hour with antiphosphohistone H2AX antibody (1:100; Upstate) at 37° C. in a humidified chamber and then with DyLight 594 anti-mouse (1:200; KPL) secondary antibody for 1 hour. Slides were washed and dried prior to counterstaining with DAPI (Vector Laboratories).

Western Blotting

Protein extractions were carried out without the use of a detergent using the CelLytic NuClear Extraction Kit (Sigma) protocol. The proteins were separated by SDS-PAGE with either 4% to 7% or 4% to 10% polyacrylamide gels and then transferred to a polyvinylidene difluoride membrane. After blocking, membranes were sequentially incubated with a primary antibody and secondary antibodies as indicated below. Antigen-antibody complexes were detected with enhanced chemiluminescence (100 µmol/L, Tris-HCl, pH 8.5; luminal, coumaric acid, and hydrogen peroxide).

The following antibodies were used in the study: polyclonal anti-DNA ligase III (Sigma) produced in rabbit, 1:1,000; monoclonal anti-PARP1 (eBioscience) produced in mouse, 1:1,000; monoclonal anti-DNA ligase IV (Santa Cruz) produced in rabbit, 1:1,000; monoclonal anti-Ku70 (Santa Cruz) produced in mouse, 1:1,000; polyclonal anti-ERα (Santa Cruz) produced in rabbit, 1:1,000; monoclonal anti-β-actin (Abcam) produced in mouse, 1:5,000; horseradish peroxidase (HRP) goat anti-rabbit (Santa Cruz), 1:2,000; and HRP goat anti-mouse (Santa Cruz), 1:5,000.

In Vivo NHEJ Repair Assay

EcoR1-linearized pUC18 plasmids (Fermentas) were transfected into cells with Amaxa Nucleofector Kit V. Plasmid DNA was extracted (QIAGEN Plasmid Mini Kit) and used to transform E. coli DH5a cells (Invitrogen), which were plated onto agar plates containing X-gal and isopropyl-1-thio-B-[scap]d[r]-galactopyranoside. Colonies were analyzed by counting the total number of white (misrepaired) and blue (correctly repaired) colonies. Plasmids from white colonies were characterized by PCR amplification of the breakpoint region with primers

5'-CGGCATCAGAGCAGATTGTA-3' and

5'-TGGATAACCGTATTACCGCC-3.

Microhomologies are defined by 2 or more identical nucleotides at the breakpoint junctions. For each experiment, plasmids from 10 white colonies were analyzed. Results are representative of 3 independent experiments+SEM.

Comparative Genomic Hybridization Array

Genomic DNA was isolated from frozen cell pellets with DNeasy tissue mini kit (QIAGEN) following the manufacturer's protocol. Sample labeling was carried out following Agilent's recommendation for 1M array comparative genomic hybridization (CGH). Agilent Human High-Resolution Discovery 1×1MCGH microarrays containing probes representing 963,000+ human genomic sequences were used. Hybridization mixtures were first denatured at 95° C. for 3 minutes and then immediately transferred to 37° C. for 30 minutes. After hybridization to microarrays for 40 hours at 65° C. in a rotating oven, the microarrays were washed and dried according to the manufacturer's protocols, and then imaged with dan Agilent G2565BA microarray scanner. Data were extracted with Feature Extraction Software (v9.5.3.1; Agilent Technologies) and analyzed by Agilent's Genomic Workbench v 5.0. Noise was estimated for each sample array by calculating the spread of the log ratio differences between consecutive probes (DLRsd) along all chromosomes and dividing by square root (1) to counteract the effect of noise averaging. Aberrant regions (gains or losses) were then identified based on hidden Markov model algorithm provided in the software (17).

MTT Cell Proliferation Assays

Cells were grown in 96-well plates with DNA ligase I/III inhibitor L67 (up to 60 µmol/L) and/or the PARP inhibitor ABT888 (up to 80 µmol/L) for 72 hours. Approximately 20 hours prior to evaluation, MTT labeling reagent (MTT in PBS; Roche) was added to each well. After incubating for 4 hours with the MTT labeling reagent, solubilization solution (10% SDS in 0.01 mol/L HCl; Roche) was added to solubilize the formazan salt crystals. The results were spectrophotometrically quantified by a VersaMax Microplate Reader at a wavelength of 550 nm and a reference wavelength of 650 nm. The effect of combining the DNA repair inhibitors was analyzed by determining the combination index (CI) described by Chou and Talalay (18, 19) with Calcusyn software (version 2.0; Biosoft). This calculation takes into account of both potency (median dose, Dm or IC50) and the shape of the dose-effect curve (the m value) to calculate the CI. L67 and ABT888 were combined at fixed ratios of doses that corresponded to 0.0001, 0.001, 0.005, 0.01, 0.05, 0.1, 0.5, 1, and 10 times the individual IC50 values. Synergy, additivity, and antagonism are defined as CI<1, CI ¼ 1, and CI>1, respectively.

Colony Survival Assays

Cells were seeded at a density of 1,000 cells per well in methylcellulose-based medium in the presence of DNA ligase I/III inhibitor, L67 (0.5 µmol/L; ref. 10); PARP inhibitor, ABT888 (0.125 µmol/L); or L67 (0.5 µmol/L) and ABT888 (0.125 µmol/L) for approximately 10 days. Colonies were stained with 2-(4-iodophenyl)-3-(4-nitrophenyl)-5-phenlytetrazolium chloride (1 mg/mL) for 16 to 24 hours before evaluation. Vital colonies were counted with an automated image analysis system (Omincon FAS IV, BIOSYS GmbH). Experiments were conducted at least 3 times, and results are representative of the mean of 3 independent experiment+SEM.

siRNA

Target plus SMART pool siRNA oligonucleotides for G22P1, DNA ligase III, and Ku70 mRNAs were purchased from Dharmacon RNA Technologies. The oligonucleotides were transiently transfected into cells with Amaxa Nucleofector Kit V (VCA-1003) in Nucleofector II Amaxa Biosystems. For transfection, 2 mL of 20 µmol/L siRNA was used per 2×106 cells. Colony survival assays were setup in combination with ABT888 (0.125 µmol/L) following siRNA ligase III or Ku70 and L67 (0.5 µmol/L) and/or ABT888 (0.125 µmol/L). Cells were harvested for Western blotting 72 hours after transfection. siRNA nontargeting pool (Dharmacon RNA Technologies) was used as a control.

Patient Samples and Immunohistochemistry

All patient breast cancer and normal reduction mamoplasty samples were collected under the Umbrella Protocol at the University of Maryland Greenebaum Cancer Center. Immunohistochemical staining was carried out on 5-µm thick, formalin-fixed, paraffin-embedded tissue sections. Tissue slides were deparaffinized 3 times in xylene and rehydrated in graded series of ethanol. Sections were pretreated with heat-induced epitope retrieval with a pressure cooker and Target Retrieval Solution (pH 6.1; Dako TRS, S1699/1700), followed by endogenous peroxidase blocking for 5 minutes with 0.3% hydrogen peroxide. All sections were incubated with the primary antibody, PARP1 (1:200; C2-10, eBioscience) or Ku70 (1:100; C-19; Santa Cruz Biotechnology) overnight at 4° C. in a hydration chamber. Primary antibody was visualized by the EnVision Dual Link system (Dako) for 30 minutes at room temperature. Slides were developed for 5 minutes using diaminobenzidine as the chromagen (Dako) and were counterstained with hematoxylin. Staining was carried out on a Dako automatic stainer.

Example 1

Altered Expression of DNA Repair Proteins in Breast Cancer Cell Lines with Acquired Resistance to Anti-Estrogen Therapeutics Although DSB repair defects in inherited breast cancers caused by mutations in either BRCA1 or BRCA2 have been extensively studied, DNA repair abnormalities in sporadic breast cancers are less well defined (4, 5). It was shown previously that the ER/PR+MCF7 cell line established from a sporadic breast cancer had a lower steady-state level of DNA ligase IV, a component of the major DNA-PK-dependent NHEJ pathway, and a higher steady-state level of DNA ligase IIIα, a component of ALT NHEJ, than the non-tumorigenic MCF10A cell line established from normal breast epithelium (10). Here, we find that MCF7 also has increased levels of PARP1, another component of ALT NHEJ, compared with MCF10A (FIG. 1A). Tamoxifen (TAM1, TAM2, and TAM3) and LTLT-resistant derivatives of MCF7 also exhibit significantly increased steady-state levels of the ALT NHEJ proteins PARP1 and DNA ligase IIIα and significantly decreased levels of DNA ligase IV compared with MCF10A (FIG. 1A).

Breast cancer cell lines with acquired resistance to anti-estrogen therapeutics are hypersensitive to a combination of DNA ligase and PARP inhibitors. Because chronic myeloid leukemia cells with increased DNA ligase IIIα-dependent ALT NHEJ activity have abnormal DSB repair (11), we determined whether the breast cancer cell lines exhibited increased sensitivity to inhibitors of the over-expressed ALT NHEJ proteins. In the absence of a DNA ligase III-specific inhibitor, we initially examined the effects of the cytotoxic DNA ligase inhibitor L67 that specifically inhibits both DNA ligase I and IIIα 36 (10). As single agents, both L67 and the PARP inhibitor ABT888 reduced the growth and viability of all the breast cancer cell lines with IC50s of about 6 and 8 µmol/L, respectively, whereas L67 and ABT888 reduced growth of MCF10A with IC50s of about 6 and 10 µmol/L, respectively (FIG. 6A-6E). At lower concentrations of L67 (0.5 µmol/L) and BT888 (0.125 µmol/L), both inhibitors alone caused small reductions in the colony survival of the tumorigenic cell lines compared with the MCF10A cell line (FIG. 1B). More strikingly, the combination of the inhibitors significantly reduced the survival of the therapy-resistant derivatives of MCF7 compared with both parental MCF7 cells and nontumorigenic MCF10A cells (FIG. 1B).

Figure 6:
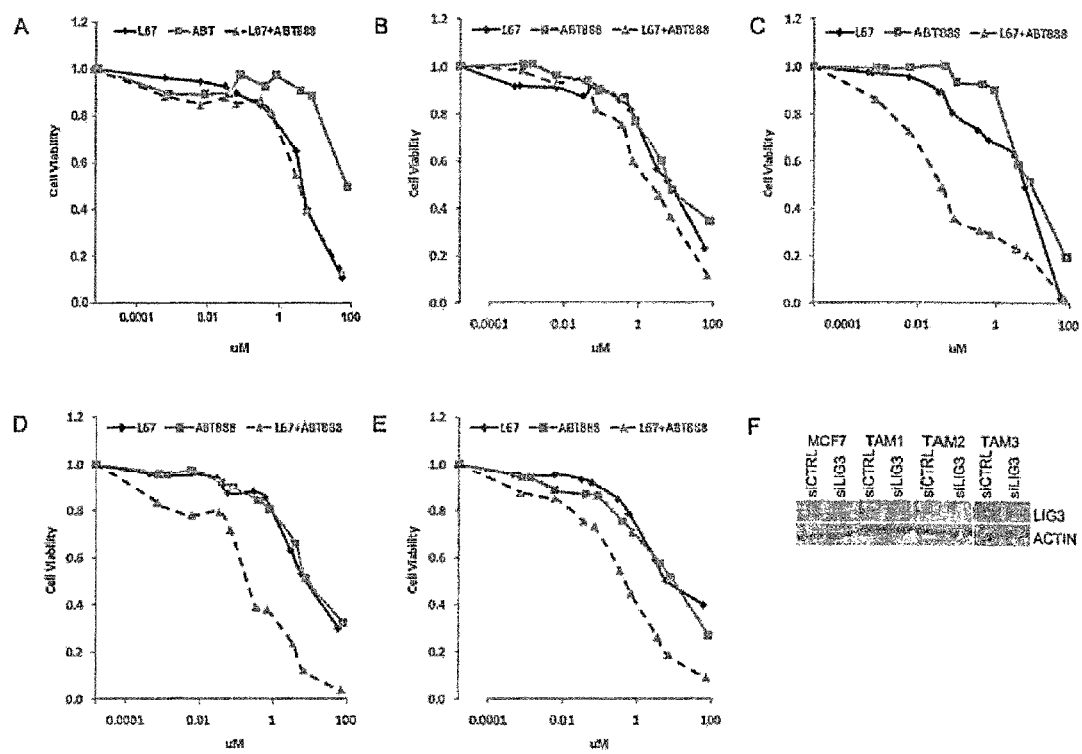
FIG. 6. A-E, Cell viability of MCF1 OA (A), MCF7 (B), tamoxifen resistant TAM1 (C), letrozole resistant LTLT (D), and MDA-MB-231 (E) following a 72-hour growth in the presence of the DNA ligase 1, III inhibitor L67 (up to 80 µM) and/or the PARP inhibitor ABT888 (up to 80 µM). The combination of L67 and ABT888 acts synergistically on breast cancer cell line and resistant derivatives. F, Representative western blot of DNA ligase IIIα levels following siRNA knockdown of DNA ligase IIIα in MCF7, TAM1, TAM2, and TAM3.

To determine whether the effects of the 2 repair inhibitors are additive or synergistic, we used the dose effect (ED) analyzer program CalcuSyn that uses the median effect method to quantify the effects of drug combinations. The CI of L67 and ABT888 for all fractional effect levels in TAM1 and LTLT was less than 1 (Table 1) indicating that the DNA repair inhibitors are acting synergistically (FIG. 6B-6D).

TABLE 1

Summary of combination studies involving concurrent administration of L67 and ABT888

| Cell lines | ED50 | ED75 | ED90 |
| --- | --- | --- | --- |
| TAM1 | 0.04463 | 0.09622 | 0.20768 |
| LTLT | 0.01526 | 0.00871 | 0.00497 |
| MDA-MB-231 | 0.10205 | 0.07717 | 0.05850 |

In contrast to PARP inhibitors (20), the DNA ligase inhibitor L67, which inhibits DNA ligases I and IIIα, has been less extensively characterized. To determine whether the activity of the DNA ligase inhibitor L67 can be specifically attributed to its effects on DNA ligase IIIα, colony survival assays were conducted following siRNA knockdown of DNA ligase IIIα alone and in combination with ABT888. Similar to L67, siRNA knockdown alone (FIG. 6F) had little effect on colony survival of MCF7 and its tamoxifen-resistant derivatives, but in combination with ABT888 significantly decreased colony survival of the tamoxifen-resistant MCF7 derivatives (FIG. 1C). Because L67 or siRNA knockdown of DNA ligase IIIα cotreatment with ABT888 produced the same decrease in colony survival, the activity of L67 is believed due to its inhibition of DNA ligase IIIα although we cannot definitively exclude off target effects of L67.

Example 2

Hormone Therapy-Resistant Breast Cancer Cell Lines are More Dependent on the ALT NHEJ Pathway for the Repair of DSBs Because both PARP1 and DNA ligase IIIα participate in the repair of DNA SSB (11, 15, 21), we predicted that the combination of repair inhibitors would lead to an accumulation of DSBs, most likely as a consequence of inhibition of SSB repair as described by others (6, 8). Interestingly, prior to treatment, the therapy-resistant derivatives of MCF7 cells had significantly higher percentage of cells with spontaneous gH2AX foci, an established marker for DSBs (22), than parental MCF7 cells and nontumorigenic MCF10A cells (FIG. 1D) but there were no differences between the cell lines in the levels of DNA SSBs, as measured by XRCC1 foci (data not shown; ref. 23). To determine whether elevated levels of ROS may contribute to the elevated levels of DSB, we measured the levels of ROS (24) but found no differences between the cell lines (data not shown). Treatment with the DNA repair inhibitor combination resulted in a significant increase in the number of DSBs in the tumorigenic MCF7 cell line and its derivatives but not in the nontumorigenic MCF10A cells (FIG. 1D). Under the same conditions, we did not observe any increase in SSBs in the cancer cell lines compared with the nontumorigenic MCF10A cells. Our results show that the repair of DSBs is abnormal in tumorigenic cells, in particular the therapy-resistant cell lines. These cell lines are more dependent upon the ALT NHEJ pathway than the nontumorigenic cells and the increased sensitivity of the therapy-resistant tumorigenic cell lines to the repair inhibitor combination is due, at least in part, to inhibition of ALT NHEJ.

Figure 2:
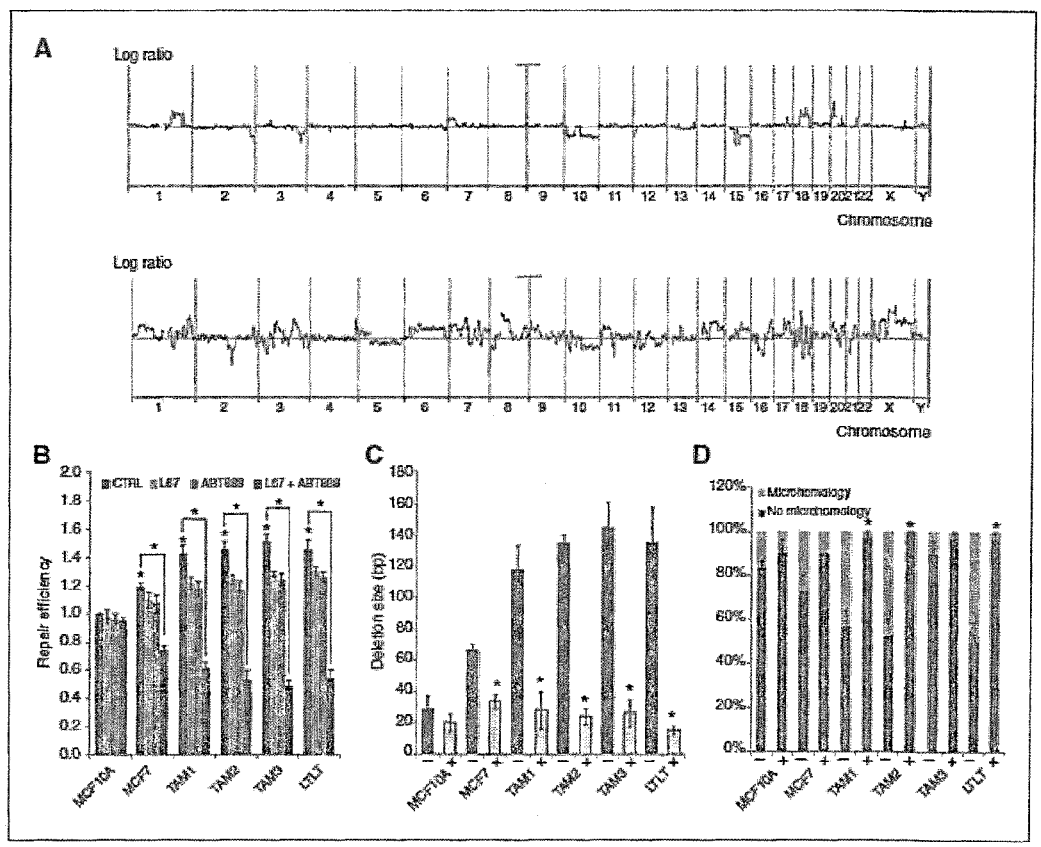
FIG. 2. A, genome view of DNA copy number variation on Agilent 1M array CGH. Top, log 2 ratio of TAM3(Cy5) versus MCF7(Cy3) and, bottom, log 2 ratio of LTLT(Cy5) versus MCF7(Cy3). The numbers labeled on the horizontal axis is for different chromosomes. Log 2 ratios of signal intensities are plotted with horizontal central line equal to zero. Alterations above the line indicate amplifications and below the line indicate deletions. The copy number variations are shown as trend lines with 2 MB base pair moving average. The log 2 ratio on the vertical axis ranges from +4 (top) to −4 (bottom). B-D, NHEJ repair assays measuring the repair of a single DSB within the LacZ gene of pUC18 plasmids in MCF10A, MCF7, tamoxifen-resistant TAM1, TAM2, TAM3, and letrozoleresistant LTLT cells following a 24-hour treatment with L67 (0.5 µmol/L) and/or ABT888 (0.125 won). B, the efficiency of repair as measured by the total number of colonies. C, bar graph showing the size of DNA deletions within the DSB region of repaired plasmids. D, DNA sequence microhomologies (>2 bp) within repaired plasmids. Bar graph showing proportion of repaired DSBs with sequence microhomologies versus no microhomologies at the repair junctions. Results are representative of the mean of 3 independent experiment+SEM; *, P<0.05 by t test.

Because the repair of DSBs by ALT NHEJ is error prone, resulting in large deletions and chromosomal translocations, we predicted that there should be increased genomic instability in the anti-estrogen therapy-resistant derivatives of MCF7 compared with parental MCF7 cells. Therefore, we examined the frequency of genomic deletions and insertions in MCF7 cells and the therapy-resistant TAM3 and LTLT derivatives with High-Resolution Discovery 1M CGH microarrays (Agilent) containing probes representing 963,000 human genomic sequences. As expected, the therapy-resistant derivatives showed an increased incidence of genomic deletions and insertions, compared with the parental MCF7 cells (FIG. 2A).

Figure 7:
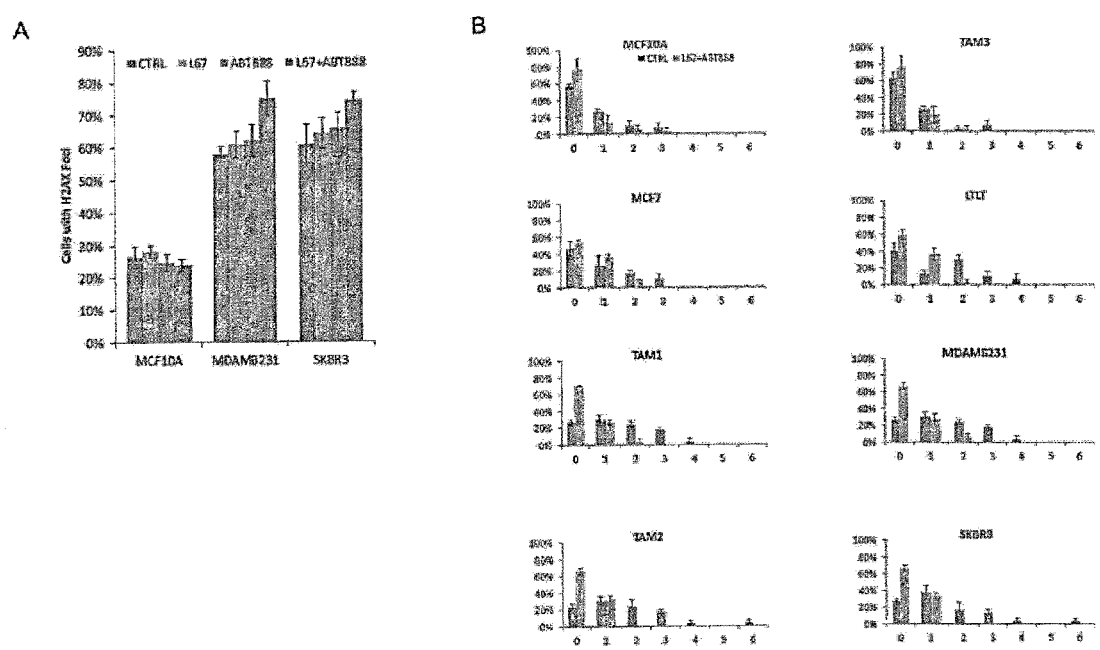
FIG. 7. A, Percentage of MCF10A, MDAMB231, and SKBR3 cells with γH2AX foci in control or co-treatment with L67 (0.5 uM) and ABT888 (0.125 uM) for 24 hours. B, Microhomology distribution for all the cell lines before and after treatment with L67+ABT888.

To measure the repair of DSBs by NHEJ, we used a plasmid-based assay in which a linearized plasmid is transfected into the tumor cell lines and then recovered for analysis after transformation into *E coli* (25). The NHEJ repair efficiency was higher in the tumorigenic cell lines, in particular the therapy-resistant derivatives, than in the nontumorigenic MCF10A cells (FIG. 2B). Treatment with the DNA repair inhibitor combination reduced the repair efficiency of the tumorigenic but not the nontumorigenic cells. To provide evidence that the increased NHEJ in the plasmid-based assay is due to the ALT NHEJ pathway, we measured the size of deletions and the occurrence of DNA sequence microhomologies at the break sites in the repaired plasmids because deletions of more than a few nucleotides and microhomology-mediated joins distinguish ALT NHEJ from DNA-PK-dependent NHEJ (11). The size of DNA deletions and frequency of microhomologies at DSB repair junctions was higher in plasmids recovered from the MCF7 cells than the nontumorigenic MCF10A cells, and these differences were even greater in the therapy-resistant derivatives of MCF7 (FIGS. 2C and D, FIGS. 7B and 8).

As expected, treatment with the DNA repair inhibitor combination significantly reduced the average size of deletions (FIG. 2C, FIG. 8) and frequency of microhomologies (FIG. 2D, FIG. 7B) so that repair was similar to that of nontumorigenic MCF10A cells. On the basis of these results, we conclude that ALT NHEJ makes a greater contribution to DSB repair in the tumorigenic cells, in particular in the therapy-resistant derivatives and is specifically inhibited by the combination of PARP and DNA ligase inhibitors.

Example 3

Figure 3:
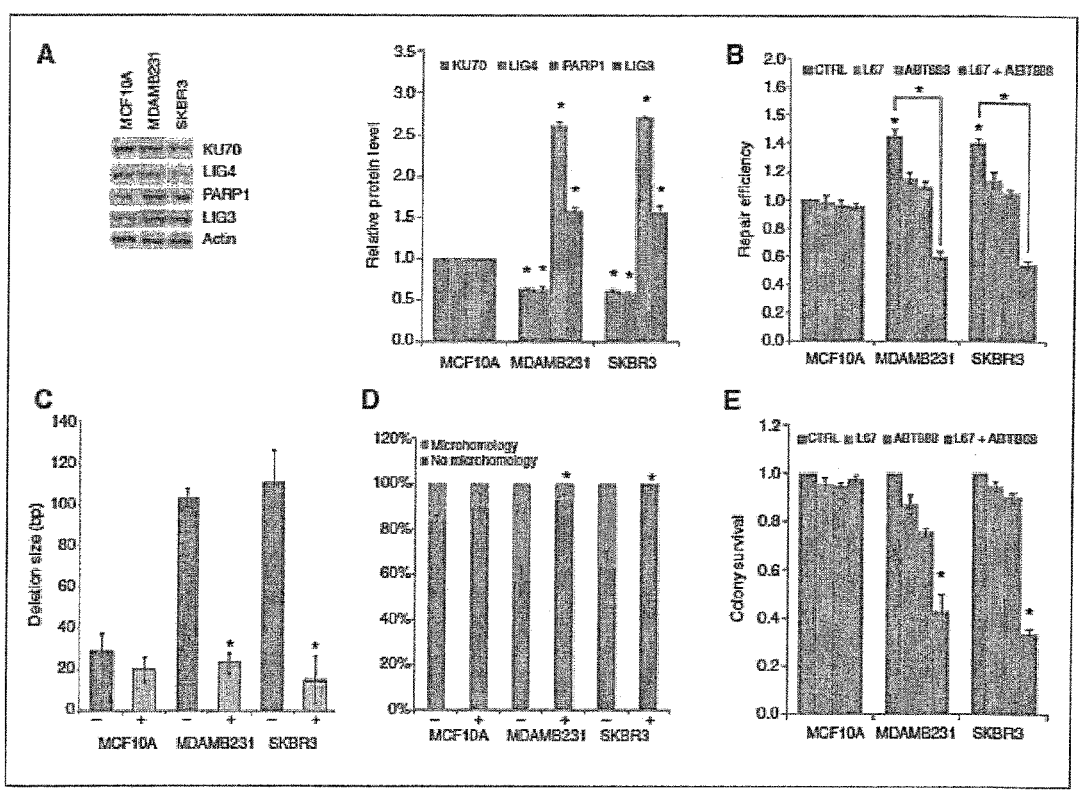
FIG. 3. A, left, representative Western blot and, right, relative steady-state levels of Ku70, DNA ligase IV, PARP1, and DNA ligase IIIα proteins in extracts from MCF10A normal breast epithelial cells and ER−/PR− breast cancer cells MDA-MB-231 and SK-BR-3. B-D, NHEJ repair assays measuring the repair of a single DSB within the LacZ gene of pUC18 plasmids in MCF10A, MDA-MB-231, and SK-BR-3 cells following a 24-hour treatment with L67 (0.5 µmol/L) and/or ABT888 (0.125 µmol/L). B, the efficiency of repair as measured by the total number of colonies. C, bar graph showing size of DNA deletions within the DSB region of repaired plasmids. D, DNA sequence microhomologies (>2 bp) within repaired plasmids. Bar graph showing proportion of repaired DSBs with sequence microhomologies versus no microhomologies at the repair junctions. E, colony survival of MCF10A, MDA-MB-231, and SK-BR-3 after a 10-day growth in the presence of L67 (0.5 µmol/L) and/or ABT888 (0.125 µmol/L). Results are representative of the mean of 3 independent experiment+SEM; *, P<0.05 by t test.
Figure 4:
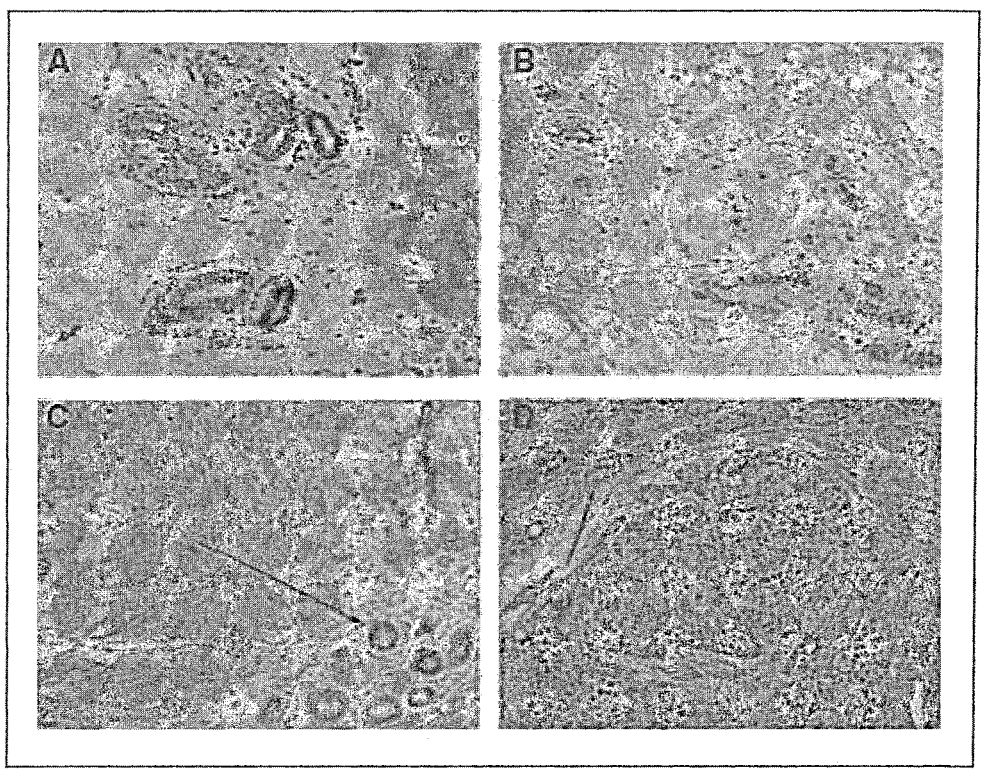
FIG. 4. Immunostaining for PARP1 and Ku70 in breast biopsies. A, strong Ku70 expression in benign breast lobules, reduction mammoplasty specimen. B, weak PARP expression in benign lobules (reduction mammoplasty specimen). C, lack of Ku70 expression in invasive ductal carcinoma. Note positive immunostaining in a benign lobule adjacent to the tumor (arrow). D, strong PARP expression in invasive ductal carcinoma. Note weak expression in entrapped benign breast epithelial profile (arrow).

ER/PR− Breast Cancer Cell Lines have Increased Expression of DNA Ligase IIIα and PARP1 and are Hypersensitive to Inhibition of ALT NHEJ Because breast cancer cell lines with acquired resistance to anti-estrogen therapeutics have abnormalities in the repair of DSBs by NHEJ, we examined the steady-state levels of NHEJ proteins in the intrinsically resistant, ER/PR− breast cancer cell lines, MDA-MB-231 and SK-BR-3. As was observed in the breast cancer cell lines with acquired resistance to anti-estrogen therapeutics, the steady-state levels of the ALT NHEJ proteins DNA ligase IIIα and PARP1 were significantly increased, whereas the steady-state levels of the DNA-PK-dependent NHEJ proteins, Ku70 and DNA ligase IV, were significantly decreased in both the ER/PR-cell lines, relative to nontumorigenic MCF10A cells (FIG. 3A). Similar to the breast cancer cell lines with acquired resistance to anti-estrogen therapies, the ER/PR-cell lines have elevated levels of endogenous DSBs (FIG. 7A) and increased error-prone repair of DSBs by ALT NHEJ (FIG. 3B-D, FIG. 7B). Treatment of the ER/PR-cell lines with a combination of PARP and DNA ligase inhibitors significantly reduced both the repair of DSBs by ALT NHEJ (FIG. 3B-D, FIG. 7B) and cell survival (FIG. 3E). The effect of the repair inhibitors was determined to be synergistic with the ED analyzer program CalcuSyn (Table 1, FIG. 6E).

Expression of PARP1 and Ku70 in ER−/PR− Breast Tumor Biopsies

Together our results show that increased dependence upon ALT NHEJ to repair DSBs is a common feature of breast cancer cell lines with either intrinsic or acquired resistance to anti-estrogen therapeutics. Because biopsies are not usually taken from patients with breast cancer that has acquired resistance to anti-estrogen therapeutics, we determined whether similar changes in the levels of NHEJ proteins can be detected in ER−/PR− breast cancer biopsies (3 triple negative HER2− and 2 ER/PR−/HER2+ samples) by immunochemistry. In accord with our data in breast cancer cell lines, the majority of the breast cancer specimens had increased PARP1 and reduced Ku70 expression compared with normal breast tissue (FIG. 4A-D, Table 2).

TABLE 2

Immunohistochemcal staining for Ku70 and PARP1 in breast biopsies

| Patient # | Tissue type | Tumor grade | ER (%) | PR (%) | HER2 | Ki-67 (%) | Ku70 | PARP1 |
|---|---|---|---|---|---|---|---|---|
| 1 | IDC | 3 | 0 | 0 | 3.4/P | 36 | +1 | +3 |
| 2 | IDC | 3 | 0 | 0 | 1.6/N | 25 | +2 | +1 |
| 3 | IOC | 3 | 0 | 0 | 0.4/N | 47 | +1 | +3 |
| 4 | IDC/brain metastasis | 3 | 0 | 0 | 4.9/P | NA | 0 | +3 |
| 5 | IDC | 3 | 0 | 0 | 0/N | 49 | +1 | +3 |
| 6 | Normal | n/a | n/a | n/a | n/a | n/a | +3 | 1-2 |
| 7 | Normal | n/a | n/a | nta | n/a | n/a | +3 | 1-2 |
| 8 | Normal | n/a | n/a | n/a | n/a | n/a | +3 | 1-2 |

NOTE:
Normal-normal breast tissue from reduction mammoplasty.
Abbreviations IDC, invasive ductal carcinoma; P, positive; N, negative; NA, not available; n/a, not applicable.

Figure 5:
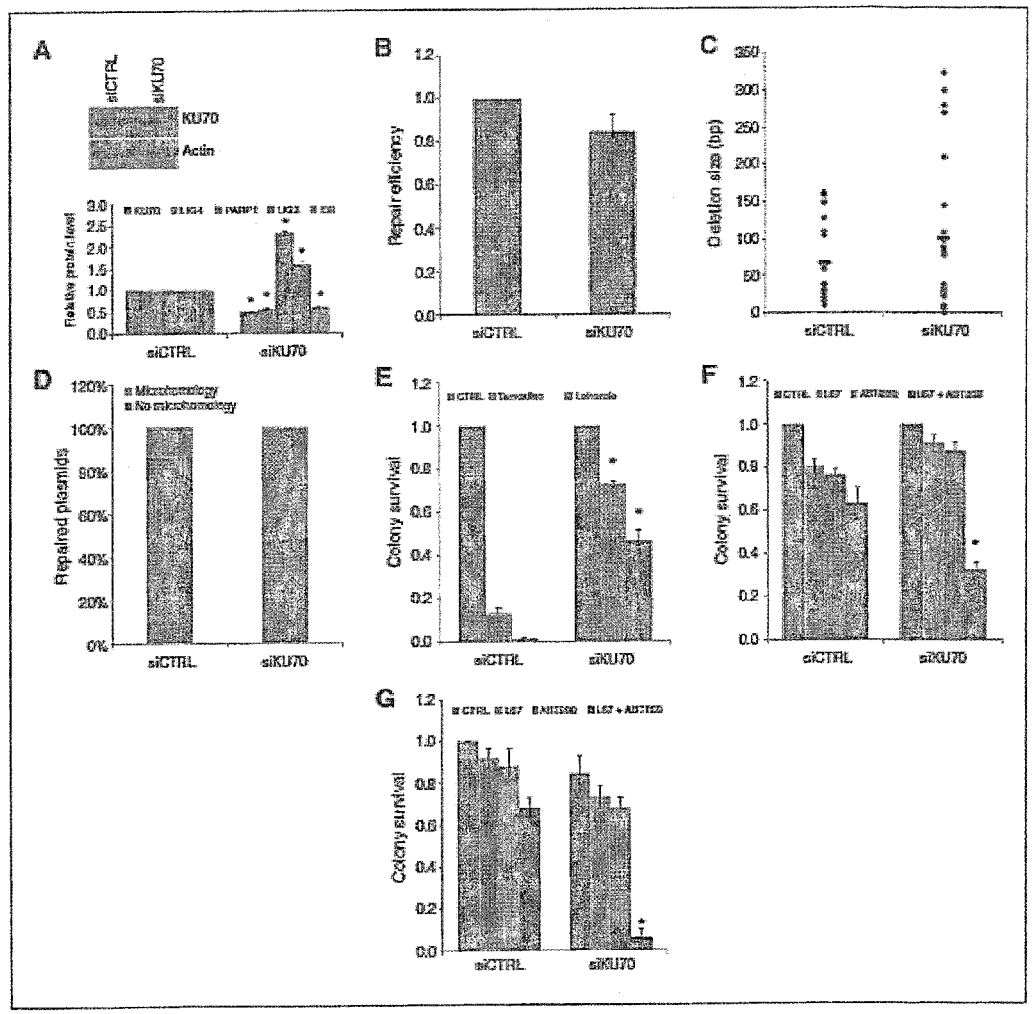
FIG. 5. A, top, representative Western blot for Ku70 in MCF7 cell extracts following siRNA knockdown of Ku70, compared with siRNA control. Actin was used as a loading control. Bottom, relative protein levels of Ku70, DNA ligase IV, PARP1, DNA ligase IIIα, and ERα in Ku70 knocked down MCF7 cells and controls. B-D, NHEJ repair assays measuring the repair of a single DSB within the LacZ gene of pUC18 plasmids following siRNA knockdown of Ku70 and a 24-hour treatment with L67 (0.5 µmol/L) and ABT888 (0.125 µmol/L) in MCF7. B, the relative efficiency of NHEJ repair. C, scatter diagram showing size of DNA deletions within the DSB region of repaired plasmids. Individual repaired DSBs are represented by diamond symbols and the mean size of deletions is indicated by horizontal bars. D, DNA sequence microhomologies (>2 bp) within repaired plasmids. Bar graph showing proportion of repaired DSBs with sequence microhomologies versus no microhomologies at the repair junctions. E and F, colony survival of MCF7 cells following siRNA knockdown of Ku70 and a 10-day growth in the presence of (E) tamoxifen (1 µmol/L) or letrozole (1 µmol/L) and (F) L67 (0.5 µmol/L) and/or ABT888 (0.125 µmol/L). NHEJ repair efficiency following a 24-hour treatment with L67 (0.5 µmol/L) and/or ABT888 (0.125 µmol/L). Results are representative of the mean of 3 independent experiment+SEM; *, P<0.05 by t test.

Down-regulation of Ku70 results in increased expression of ALT NHEJ proteins and increased sensitivity to the combination of DNA ligase and PARP inhibitors. An intriguing feature that is particularly evident in ER/PR− breast cancer lines and primary biopsies is the reciprocal changes in the steady-state levels of key factors involved in DNA-PK-dependent and ALT NHEJ. To determine whether expression levels of ALT NHEJ and DNA-PK-dependent NHEJ factors are related, we used siRNA knockdown to modulate the levels of Ku70. A 50% reduction of Ku70 levels in ER/PR+MCF7 cells resulted in increased steady-state levels of both PARP1 and DNA ligase IIIα (FIG. 5A) with a concomitant increase in both the repair of DSBs by ALT NHEJ (FIG. 5B-D). Interestingly, reducing Ku70 by siRNA also resulted in a significant decrease in the expression of both DNA ligase IV and ERα (FIG. 5A) with the decreased ERα expression resulting in a decreased sensitivity to both tamoxifen and letrozole (FIG. 5E). However, the increased dependence upon ALT NHEJ sensitizes the MCF7 cells to the combination of L67 and ABT888, resulting in a significant decrease in colony survival (FIG. 5F) and NHEJ repair efficiency (FIG. 5G).

DISCUSSION

Although the majority of breast cancers are estrogen-dependent and effective anti-estrogen therapies have been developed, there is an urgent need to develop new and improved therapeutic strategies for patients whose disease is refractory to anti-estrogen therapies. Alterations in the network of pathways that respond to DNA damage and maintain genome stability are presumed to underlie the genomic instability and increased sensitivity of cancer cells to cytotoxic DNA damaging agents used in cancer treatment (26). These abnormalities are potential targets for the development of therapeutics that either alone or in combination with cytotoxic DNA damaging agents will specifically enhance killing of cancer cells. In this study, we show that an ALT NHEJ pathway is upregulated in breast cancer cell lines that are either intrinsically resistant or have acquired resistance to anti-estrogen therapies and that these cell lines are hypersensitive to DNA repair inhibitors that target the ALT NHEJ pathway.

In contrast to the major DNA-PK-dependent NHEJ repair pathway, the ALT NHEJ pathway frequently generates large chromosomal rearrangements, including large deletions and translocations during the repair of DSBs (9). Notably, the breast cancer cell lines with acquired resistance to anti-estrogen therapies have more endogenous DSBs compared with MCF10A and MCF7. This is consistent with a published study showing that MCF7 cells have decreased levels of anti-oxidants and increased levels of oxidative DNA damage (27). Furthermore, the therapy-resistant derivatives showed higher incidence of large deletions compared with their parental MCF7 cells. This shows that a combination of higher endogenous DNA damage, in particular complex clustered oxidative lesions (25) and increased activity of the error-prone ALT NHEJ pathway contribute to the increased genomic instability in these cell lines. Although it is likely that the genomic instability drives disease progression and acquired resistance to cancer therapeutics, the DNA repair abnormality allows the design of a novel therapeutic strategy that selectively targets the therapy-resistant breast cancer cells.

Here, we have shown that therapy-resistant derivatives of estrogen-dependent MCF7 cells with increased ALT NHEJ activity are preferentially killed by a combination of DNA repair inhibitors that target 2 ALT NHEJ components, PARP1 and DNA ligase IIIα. The synergistic effect of combining the inhibitors is not consistent with them partially and/or completely inhibiting 2 components of the same pathway, showing that inhibition of other repair pathways contributes to cell killing. In addition to ALT NHEJ, both PARP1 and DNA ligase IIIα participate in the same SSB repair pathway (28, 29). Thus, although inhibition of the PARP1-dependent SSB repair results in replication-associated DSBs (7, 8), it cannot account for the observed synergy. In fact under conditions in which the inhibitors caused an increase in DSBs, we did not observe an increase in SSBs (data not shown). DNA ligase IIIα could participates in the repair of replication-associated DSBs by homologous recombination, and/or the inhibition of DNA ligase IIIα-dependent base excision repair of spontaneous DNA damage adds to the number of unrepaired SSBs that are then converted into DSBs as a consequence of DNA replication. ALT NHEJ acts as a backup pathway for recombinational repair of replication-associated DSBs and so increasing the number of replication-associated DSBs combined with inhibition of ALT NHEJ and/or homologous recombination results in the accumulation of DSBs and cell death. The efficacy of the repair inhibitor combination can also or alternatively be due to the targeting of other cellular pathways in addition to ALT NHEJ and SSB repair. For example, the PARP inhibitor can target cellular function involving other members of the PARP family (30) in addition to PARP1, whereas base excision repair and mitochondrial DNA are also impacted by inhibition of DNA ligase IIIα (31, 32).

The higher steady-state levels of PARP1 and DNA ligase IIIα correlate with the increased activity of the ALT NHEJ pathway and increased sensitivity to the combination of PARP and DNA ligase inhibitors. In addition, reduced levels of the canonical NHEJ components, Ku and DNA ligase IV, were also frequently observed in cells with upregulated ALT NHEJ, showing that these DSB repair pathways are linked. In fact, recent studies have shown that Ku-dependent NHEJ suppresses the repair of DSBs by ALT NHEJ, providing an explanation as to why ALT NHEJ is more evident in cells that are deficient in the Ku-dependent NHEJ pathway (33-36). Here, we have shown that knockdown of Ku70 results in a significant increase in levels of PARP1 and DNA ligase IIIα. Increased levels of DSBs resulting from reduced Ku levels can increase expression of ALT NHEJ factors via DNA damage response signaling pathways (37). In addition, or alternatively, Ku can transcriptionally regulate genes encoding ALT NHEJ proteins (38-40).

Our results in cell lines show that dysregulation of NHEJ, resulting from abnormal expression of factors involved in DNA-PK-dependent NHEJ proteins and ALT NHEJ, is a common characteristic of breast cancers with intrinsic or acquired resistance to hormone therapy. Notably, we observed similar changes in expression of Ku70 and PARP1 in biopsies from ER-PR- breast tumors, indicating that the repair abnormality likely occurs in primary tumors, and that these expression patterns can be used to identify tumors with this DNA repair abnormality. Characterization of breast cancer subtypes will lead to the delineation of additional groups of patients who are candidates for therapy with this combination of DNA repair inhibitors when conventional frontline therapies have failed (41).

In summary, we have shown that breast cancers that are resistant to anti-estrogen therapies have a DNA repair abnormality, increased dependence upon an ALT NHEJ, which can be selectively targeted by the combined action of PARP and DNA ligase inhibitors. Tumors that are likely to respond to the repair inhibitor combination are identified based on the expression levels of the ALT NHEJ factors and the DNA-PK-dependent NHEJ factors. Our studies identify ALT NHEJ as a therapeutic target in forms of breast cancer for which there is a compelling need for more effective treatment options.

REFERENCES

1. Jordan V C, Brodie A M. Development and evolution of therapies targeted to the estrogen receptor for the treatment and prevention of breast cancer. Steroids 2007; 72:7-25.
2. Brodie A, Njar V, Macedo L F, Vasaitis T S, Sabnis G. The Coffey Lecture: steroidogenic enzyme inhibitors and hormone dependent cancer. Urol Oncol 2009; 27:53-63.
3. Macedo L F, Sabnis G, Brodie A. Aromatase inhibitors and breast cancer. Ann N Y Acad Sci 2009; 1155:162-73.
4. Venkitaraman A R. Cancer susceptibility and the functions of BRCA1 and BRCA2. Cell 2002; 108:171-82.
5. Marshall M, Solomon S. Hereditary breast-ovarian cancer: clinical findings and medical management. Plast Surg Nurs 2007; 27:124-7.
6. McCabe N, Turner N C, Lord C J, Kluzek K, Bialkowska A, Swift S, et al. Deficiency in the repair of DNA damage by homologous recombination and sensitivity to poly(ADP-ribose) polymerase inhibition. Cancer Res 2006; 66:8109-15.
7. Bryant H E, Schultz N, Thomas H D, Parker K M, Flower D, Lopez E, et al. Specific killing of BRCA2-deficient tumours with inhibitors of poly(ADP-ribose) polymerase. Nature 2005; 434:913-7.
8. Farmer H, McCabe N, Lord C J, Tutt A N, Johnson D A, Richardson T B, et al. Targeting the DNA repair defect in BRCA mutant cells as a therapeutic strategy. Nature 2005; 434:917-21.
9. Nussenzweig A, Nussenzweig M C. A backup DNA repair pathway moves to the forefront. Cell 2007; 131:223-5.
10. Chen X, Zhong S, Zhu X, Dziegielewska B, Ellenberger T, Wilson G M, et al. Rational design of human DNA ligase inhibitors that target cellular DNA replication and repair. Cancer Res 2008; 68:3169-77.
11. Sallmyr A, Tomkinson A E, Rassool F V. Up-regulation of WRN and DNA ligase III alpha in chronic myeloid leukemia: consequences for the repair of DNA double-strand breaks. Blood 2008; 112:1413-23.
12. Fan J, Li L, Small D, Rassool F. Cells expressing FLT3/ITD mutations exhibit elevated repair errors generated through alternative NHEJ pathways: implications for genomic instability and therapy. Blood 2010; 116:5298-305.
13. Wang H, Rosidi B, Perrault R, Wang M, Zhang L, Windhofer F, et al. DNA ligase III as a candidate component of backup pathways of nonhomologous end joining. Cancer research 2005; 65:4020-30.
14. Wang H, Perrault A R, Takeda Y, Qin W, Iliakis G. Biochemical evidence for Ku-independent backup pathways of NHEJ. Nucleic Acids Res 2003; 31:5377-88.
15. Audebert M, Salles B, Calsou P. Involvement of poly (ADP-ribose) polymerase-1 and XRCC1/DNA ligase III in an alternative route for DNA double-strand breaks rejoining. J Biol Chem 2004; 279: 55117-26.
16. Long B J, Jelovac D, Handratta V, Thiantanawat A, MacPherson N, Ragaz J, et al. Therapeutic strategies using the aromatase inhibitor letrozole and tamoxifen in a breast cancer model. J Natl Cancer Inst 2004; 96:456-65.
17. de Smith A J, Tsalenko A, Sampas N, Scheffer A, Yamada N A, Tsang P, et al. Array CGH analysis of copy number variation identifies 1284 new genes variant in healthy white males: implications for association studies of complex diseases. Hum Mol Genet 2007; 16:2783-94.
18. Chou T C, Talalay P. Quantitative analysis of dose-effect relationships: the combined effects of multiple drugs or enzyme inhibitors. Adv Enzyme Regul 1984; 22:27-55.
19. Chou T C. The median effect principle and the combination index for quantitation of synergism and antagonism. San Diego: Academic Press; 1991.
20. Lord C J, Ashworth A. Targeted therapy for cancer using PARP inhibitors. Curr Opin Pharmacol 2008; 8:363-9.
21. Wang H, Rosidi B, Perrault R, Wang M, Zhang L, Windhofer F, et al. DNA ligase III as a candidate component of backup pathways of nonhomologous end joining. Cancer Res 2005; 65:4020-30. 742
22. Lobrich M, Shibata A, Beucher A, Fisher A, Ensminger M, Goodarzi A A, et al. gammaH2AX foci analysis for monitoring DNA double-strand break repair: strengths, limitations and optimization. Cell Cycle 2010; 9:662-9.
23. Kunz C, Focke F, Saito Y, Schuermann D, Lettieri T, Selfridge J, et al. Base excision by thymine DNA glycosylase mediates DNA-directed cytotoxicity of 5-fluorouracil. PLoS Biol 2009; 7:e91.
24. Rassool F V, Gaymes T J, Omidvar N, Brady N, Beurlet S, Pla M, et al. Reactive oxygen species, DNA damage, and error-prone repair: a model for genomic instability with progression in myeloid leukemia? Cancer Res 2007; 67:8762-71.
25. Gaymes T J, Mufti G J, Rassool F V. Myeloid leukemias have increased activity of the nonhomologous end joining pathway and concomitant DNA misrepair that is dependent on the Ku70/86 heterodimer. Cancer Res 2002; 62:2791-7.
26. Rassool F V, Tomkinson A E. Targeting abnormal DNA double strand break repair in cancer. Cell Mol Life Sci 2010; 67:3699-710.

27. Francisco D C, Peddi P, Hair J M, Flood B A, Cecil A M, Kalogerinis P T, et al. Induction and processing of complex DNA damage in human breast cancer cells MCF-7 and nonmalignant MCF-10A cells. Free Radic Biol Med 2008; 44:558-69.
28. Okano S, Lan L, Caldecott K W, Mori T, Yasui A. Spatial and temporal cellular responses to single-strand breaks in human cells. Mol Cell Biol 2003; 23:3974-81.
29. Okano S, Lan L, Tomkinson A E, Yasui A. Translocation of XRCC1 and DNA ligase III alpha from centrosomes to chromosomes in response to DNA damage in mitotic human cells. Nucleic Acids Res 2005; 33:422-9.
30. Krishnakumar R, Kraus W L. The PARP side of the nucleus: molecular actions, physiological outcomes, and clinical targets. Mol Cell 2010; 39:8-24.
31. Simsek D, Furda A, Gao Y, Artus J, Brunet E, Hadjantonakis A K, et al. Crucial role for DNA ligase III in mitochondria but not in Xrcc1-dependent repair. Nature 2011; 471:245-8.
32. Gao Y, Katyal S, Lee Y, Zhao J, Rehg J E, Russell H R, et al. DNA ligase III is critical for mtDNA integrity but not Xrcc1-mediated nuclear DNA repair. Nature 2011; 471: 240-4.
33. Corneo B, Wendland R L, Deriano L, Cui X, Klein I A, Wong S Y, et al. Rag mutations reveal robust alternative end joining. Nature 2007; 449: 483-6.
34. Yan C T, Boboila C, Souza E K, Franco S, Hickernell T R, Murphy M, et al. IgH class switching and translocations use a robust non-classical end joining pathway. Nature 2007; 449:478-82.
35. Fattah F, Lee E H, Weisensel N, Wang Y, Lichter N, Hendrickson E A. Ku regulates the non-homologous end joining pathway choice of DNA double-strand break repair in human somatic cells. PLoS Genet 2010; 6:e1000855.
36. Simsek D, Jasin M. Alternative end joining is suppressed by the canonical NHEJ component Xrcc4-ligase IV during chromosomal translocation formation. Nat Struct Mol Biol 2010; 17:410-6.
37. Sekiguchi J, Ferguson D O, Chen H T, Yang E M, Earle J, Frank K, et al. Genetic interactions between ATM and the nonhomologous end joining factors in genomic stability and development. Proc Natl Acad Sci USA 2001; 98:3243-8.
38. Medunjanin S, Weinert S, Schmeisser A, Mayer D, Braun-Dullaeus R C. Interaction of the double-strand break repair kinase DNA-PK and estrogen receptor-alpha. Mol Biol Cell 2010; 21:1620-8.
39. Medunjanin S, Weinert S, Poitz D, Schmeisser A, Strasser R H, Braun-Dullaeus R C. Transcriptional activation of DNA-dependent protein kinase catalytic subunit gene expression by oestrogen receptor-alpha. EMBO Rep 2010; 11:208-13.
40. Nolens G, Pignon J C, Koopmansch B, Elmoualij B, Zorzi W, DePauw E, et al. Ku proteins interact with activator protein-2 transcription factors and contribute to ERBB2 overexpression in breast cancer cell lines. Breast Cancer Res 2009; 11:R83.
41. Cheang M C, Chia S K, Voduc D, Gao D, Leung S, Snider J, et al. Ki67 index, HER2 status, and prognosis of patients with luminal B breast cancer. J Natl Cancer Inst 2009; 101:736-50.

---

The invention claimed is:

1. A method of treating a breast cancer tumor which is non-responsive or intrinsically resistant to anti-estrogen therapy in a patient in need comprising administering to said patient a therapeutically effective amount of an inhibitor of an alternative (ALT) non-homologous end joining (NHEJ) factor.

2. The method of claim 1, wherein the inhibitor of alternative (ALT) non-homologous end joining (NHEJ) factor is a Poly [ADP-Ribose] Polymerase 1 (PARP1) inhibitor or a DNA ligase IIIα inhibitor.

3. The method of claim 1, wherein said patient is treated with a combination of a PARP1 inhibitor and a DNA ligase IIIα inhibitor.

4. The method of claim 1, wherein said patient's breast cancer tumor also under-expresses one or more DNA-PK-dependent NHEJ factors.

5. The method of claim 4, wherein said patient's breast cancer tumor under-expresses Ku70 and DNA Ligase IV.

6. The method of claim 1, wherein said patient's breast cancer tumor is also resistant to anti-HER2 therapies.

7. The method of claim 1, wherein the PARP inhibitor ABT888 and at least one DNA ligase IIIα inhibitor selected from the group consisting of L67, L-67-5, L67-6 and GEG54 are co-administered to said patient.

8. The method of claim 3, wherein the PARP1 inhibitor and a DNA ligase IIIα inhibitor are co-administered to said patient.

9. The method of claim 1, wherein the PARP1 inhibitor is selected from the group consisting of nicotinamide; NU1025;

3-aminobenzamide; 4-amino-1,8-naphthalimide; 1,5-isoquinolinediol; 6(5H)-phenanthriddinone; 1,3,4,5,-tetrahydrobenzo(c)(1,6)- and (c)(1,7)-naphthyridin-6 ones; adenosine substituted 2,3-dihydro-1H-isoindol-1-ones; AG14361; AG014699; 2-(4-chlorophenyl)-5-quinoxalinecarboxamide; 5-chloro-2-[3-(4-phenyl-3,6-dihydro-1(2H)-pyridinyl)propyl]-4(3H)-quinazolinone; isoindolinone derivative INO-1001; 4-hydroxyquinazoline; 2-[3-[4-(4-chlorophenyl)1-piperazinyl]propyl]-4-3(4)-quinazolinone; 1,5-dihydroxyisoquinoline (DHIQ); 3,4-dihydro-5 [4-(1-piperidinyl)(butoxy)-1(2H)-isoquinolone; CEP-6800; GB-15427; PJ34; DPQ; BS-201; AZD2281 (Olaparib); BS401; CHP101; CHP102; INH2BP; BSI201; BSI401; TIQ-A; an imidazobenzodiazepine; 8-hydroxy-2-methylquinazolinone (NU1025), CEP 9722, MK 4827, LT-673; 3-aminobenzamide; Olaparib (AZD2281; ABT-888 (Veliparib); BSI-201 (Iniparib); Rucaparib (AG-014699); INO-1001; A-966492; PJ-34; and PARP1 inhibitors described in U.S. Patent Application Document No 20100099683 (Ser. No. 12/576,410), entitled "Compounds that Inhibit Human DNA Ligases and Methods of Treating Cancer".

10. The method of claim 3, wherein ABT888 and at least one DNA ligase IIIα inhibitor selected from the group consisting of L67, L-67-5, L67-6 and GEG54 are administered to said patient.

11. A method of treating an anti-estrogen-naive breast cancer tumor whose cells over-express one or more ALT NHEJ factors in a patient in need comprising co-administering to said patient a therapeutically effective amount of a PARP1 inhibitor and a DNA ligase IIIα inhibitor.

12. The method of claim 11, wherein the ALT NHEJ factors are PARP1 and DNA ligase IIIα.

13. A method of treating an anti-estrogen-naive breast cancer tumor whose cells over-express one or more ALT NHEJ factors and under-express one or more DNA-PK-dependent NHEJ factors in a patient in need comprising co-administering a therapeutically effective amount of a PARP1 inhibitor and a DNA ligase IIIα inhibitor to said patient.

14. The method of claim 13, wherein the ALT NHEJ factors are PARP1 and DNA ligase IIIα and the DNA-PK-dependent NHEJ factors are Ku70 and DNA Ligase IV.

15. A method of treating an anti-estrogen-naive breast cancer tumor whose cells, based on an evaluation of clinical factors selected from the group consisting of mammogram evaluation, breast MRI evaluation, ultrasound evaluation, age, fractures, bone mineral density screening, Chronic Disease Scores, and co-morbidities, are considered likely to over-express one or more ALT NHEJ factors in a patient in need comprising co-administering a therapeutically effective amount of PARP1 inhibitor and a DNA ligase IIIα inhibitor to said patient.

16. The method of claim 15, wherein the ALT NHEJ factors are PARP1 and DNA ligase IIIα.

17. A method of treating an anti-estrogen-naive breast cancer tumor whose cells, based on an evaluation of clinical factors selected from the group consisting of mammogram evaluation, breast MRI evaluation, ultrasound evaluation, age, fractures, bone mineral density screening, Chronic Disease Scores, and co-morbidities, are considered likely to over-express one or more ALT NHEJ factors and to under-express one or more DNA-PK-dependent NHEJ factors in a patient in need comprising co-administering a therapeutically effective amount of PARP1 inhibitor and a DNA ligase IIIα inhibitor to said patient.

18. The method of claim 17, wherein the ALT NHEJ factors are PARP1 and DNA ligase III and the DNA-PK-dependent NHEJ factors are Ku70 and DNA Ligase IV.

19. A method of treating a treatment-naive breast cancer tumor whose cells over-express one or more ALT NHEJ factors in a patient in need comprising co-administering to said patient a therapeutically effective amount of PARP1 inhibitor and a DNA ligase IIIα inhibitor.

20. The method of claim 19, wherein the ALT NHEJ factors are PARP1 and DNA ligase IIIα.

21. A method of treating a treatment-naive breast cancer tumor whose cells over-express one or more ALT NHEJ factors and under-express one or more DNA-PK-dependent NHEJ factors in a patient in need comprising co-administering a therapeutically effective amount of PARP1 inhibitor and a DNA ligase IIIα inhibitor to said patient.

22. The method of claim 21, wherein the ALT NHEJ factors are PARP1 and DNA ligase III and the DNA-PK-dependent NHEJ factors are Ku70 and DNA Ligase IV.

23. A nucleic acid array for expression-based classification of a breast cancer tumor as being either responsive or non-responsive to anti-estrogen mono or co-therapy, the array comprising at least 10 probes immobilized on a solid support, each of the probes:
  (a) having a length of between about 25 to about 50 or more nucleotides; and
  (b) being derived from sequences corresponding to, or complementary to, transcripts or partial transcripts of each member of one or more prognostic gene sets comprised of genes encoding PARP1, DNA ligase IIIα, Ku70 or DNA ligase IV.

24. A method of treating a pancreatic cancer which is non-responsive to chemotherapy and/or radiation in a patient in need comprising co-administering a therapeutically effective amount of PARP1 inhibitor and a DNA ligase IIIα inhibitor to said patient.

25. The method of claim 24, wherein the PARP1 inhibitor and a DNA ligase IIIα inhibitor are co-administered to said patient and said patient cannot tolerate either chemotherapy or radiation.

26. The method of claim 25, wherein the PARP inhibitor ABT888 and at least one DNA ligase IIIα inhibitor selected from the group consisting of L67, L-67-5, L67-6 and GEG54 are co-administered to said patient.

27. The method of claim 24, wherein the PARP1 inhibitor is selected from the group consisting of nicotinamide; NU1025; 3-aminobenzamide; 4-amino-1,8-naphthalimide; 1,5-isoquinolinediol; 6(5H)-phenanthriddinone; 1,3,4,5,-tetrahydrobenzo(c)(1,6)- and (c)(1,7)-naphthyridin-6 ones; adenosine substituted 2,3-dihydro-1H-isoindol-1-ones; AG14361; AG014699; 2-(4-chlorophenyl)-5-quinoxalinecarboxamide; 5-chloro-2-[3-(4-phenyl-3,6-dihydro-1(2H)-pyridinyl)propyl]-4(3H)-quinazolinone; isoindolinone derivative INO-1001; 4-hydroxyquinazoline; 2-[3-[4-(4-chlorophenyl) 1-piperazinyl]propyl]-4-3(4)-quinazolinone; 1,5-dihydroxyisoquinoline (DHIQ); 3,4-dihydro-5 [4-(1-piperidinyl)(butoxy)-1(2H)-isoquinolone; CEP-6800; GB-15427; PJ34; DPQ; BS-201; AZD2281 (Olaparib); BS401; CHP101; CHP102; INH2BP; BSI201; BSI401; TIQ-A; an imidazobenzodiazepine; 8-hydroxy-2-methylquinazolinone (NU1025), CEP 9722, MK 4827, LT-673; 3-aminobenzamide; Olaparib (AZD2281; ABT-888 (Veliparib); BSI-201 (Iniparib); Rucaparib (AG-014699); INO-1001; A-966492 PJ-34 and mixtures thereof.

28. A method of treating a chemotherapy and/or radiation-naive pancreatic cancer in a patient in need comprising co-administering a therapeutically effective amount of PARP1 inhibitor and a DNA ligase IIIα inhibitor to said patient, wherein the pancreatic cancer cells, based on an evaluation of clinical factors selected from the group consisting of age, tumor size, abdominal pain, weight loss, jaundice, insulin and/or lipid imbalances and co-morbidities, are considered likely to over-express one or more ALT NHEJ factors.

* * * * *